US011427783B2

(12) United States Patent
O'Leary et al.

(10) Patent No.: US 11,427,783 B2
(45) Date of Patent: Aug. 30, 2022

(54) PERFUMING COMPOSITIONS

(71) Applicant: Firmenich SA, Geneva (CH)

(72) Inventors: Nicholas O'Leary, Plainsboro, NJ (US); Addi Fadel, Plainsboro, NJ (US); Jeffrey Dundale, Plainsboro, NJ (US); Christelle Porcherot Lassallette, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/307,929

(22) PCT Filed: Jun. 30, 2017

(86) PCT No.: PCT/EP2017/066264
§ 371 (c)(1),
(2) Date: Dec. 6, 2018

(87) PCT Pub. No.: WO2018/002298
PCT Pub. Date: Jan. 4, 2018

(65) Prior Publication Data
US 2019/0264133 A1  Aug. 29, 2019

Related U.S. Application Data

(60) Provisional application No. 62/357,317, filed on Jun. 30, 2016.

(30) Foreign Application Priority Data

Dec. 12, 2016 (EP) .................................. 16203542

(51) Int. Cl.
| | |
|---|---|
| *C11B 9/00* | (2006.01) |
| *C11B 9/02* | (2006.01) |
| *A61K 8/00* | (2006.01) |
| *A61Q 13/00* | (2006.01) |
| *A61L 9/01* | (2006.01) |
| *A61L 9/12* | (2006.01) |
| *A61L 9/03* | (2006.01) |
| *C11D 3/50* | (2006.01) |
| *A61Q 15/00* | (2006.01) |

(52) U.S. Cl.
CPC .............. *C11B 9/0076* (2013.01); *A61L 9/01* (2013.01); *A61Q 13/00* (2013.01); *C11B 9/003* (2013.01); *C11B 9/0015* (2013.01); *C11B 9/0019* (2013.01); *C11B 9/0038* (2013.01); *C11B 9/0053* (2013.01); *C11B 9/0061* (2013.01); *A61L 9/035* (2013.01); *A61L 9/125* (2013.01); *A61Q 15/00* (2013.01); *C11D 3/50* (2013.01)

(58) Field of Classification Search
CPC ... C11B 9/0076; C11B 9/0038; C11B 9/0019; C11B 9/003; C11B 9/0061; C11B 9/0053; C11B 9/0015; A61L 9/01; A61L 9/035; A61L 9/125; A61Q 13/00; A61Q 15/00
USPC ......................................... 512/5, 1
See application file for complete search history.

(56) References Cited

U.S. PATENT DOCUMENTS

| | | | |
|---|---|---|---|
| 9,540,589 B2 * | 1/2017 | Angel | ....................... A61L 9/01 |
| 2002/0159916 A1 * | 10/2002 | Whitby | ................... A61L 9/035 |
| | | | 422/4 |
| 2015/0016464 A1 | 1/2015 | Chan et al. | |
| 2015/0164764 A1 | 6/2015 | Bonnet et al. | |

FOREIGN PATENT DOCUMENTS

| | | |
|---|---|---|
| EP | 2810663 A1 | 12/2014 |
| EP | 3103523 A1 | 12/2016 |
| JP | 2003190264 A | 7/2003 |

OTHER PUBLICATIONS

Morata, Red Wine Technology, 2018, p. 133 (Year: 2018).*
International Search Report and Written Opinion, for International Application No. PCT/EP2017/066264, dated Oct. 19, 2017.

* cited by examiner

*Primary Examiner* — Jessica Whiteley

(57) ABSTRACT

The aspects presented herein provide fragrance compositions having an olfacive profile that changes with time, wherein the fragrance compositions comprise at least two contrasting perfume accords that provide an olfactory modulating effect, wherein the perfume formulation delivers a desirable scent with increased perceived intensity and improved longevity of perception.

15 Claims, 11 Drawing Sheets

PERFUMING COMPOSITIONS

CROSS-REFERENCE

This application is a 371 filing of International Patent Application PCT/EP2017/066264 filed 30 Jun. 2017, which claims the benefit of U.S. provisional patent application 62/357,317, filed 30 Jun. 2016, and EP application no. 16203542.2, filed 12 Dec. 2016, the contents of which are hereby incorporated by reference in their entirety.

FIELD OF THE INVENTION

The present invention relates to the field of perfumery. In particular, fragrance compositions having an olfactive profile that changes with time, wherein the fragrance compositions comprise at least two contrasting perfume accords that provide an olfactory modulating effect, wherein the perfume formulation delivers a desirable scent with increased perceived intensity and improved longevity of perception.

BACKGROUND

Consumers are looking for different sensory experiences, and the perfume industry is constantly seeking for solutions to answer that demand and in particular for ways to prolong the perfume experience over time. The industry is also keen on finding solutions to phenomenon referred to as perfume habituation and perfume adaptation resulting in a decrease of perceived intensity over time.

SUMMARY

One aspect presented herein provides a perfume composition comprising at least two perfuming accords,
 wherein a first perfume accord of the at least two perfuming accords comprises perfuming compounds dominated by a first olfactive note,
 wherein a second perfume accord of the at least two perfuming accords comprises perfuming compounds dominated by a second olfactive note,
 wherein the first and second olfactive notes are contrasting notes,
 wherein the first perfume accord is present in the perfume composition in an amount sufficient for the first olfactive note to be perceived by a subject at a first time,
 wherein the second perfume accord is present in the perfume composition in an amount sufficient for the second olfactive note to be perceived by a subject at a second time, and
 wherein the perception of the first olfactive note and the second olfactive note is at a level sufficient to reduce, prevent, or suppress a reduced perception of the perfume composition by the subject over time.

In one aspect, the second time is after the first time.

In one aspect, the first perfume accord comprises perfuming compounds having a volatility ranging from 70,000 to 100 µg/l in air.

In one aspect, the second perfume accord comprises perfuming compounds having a volatility ranging from 99 to 50 µg/l in air.

In one aspect, the sufficient amount of the first perfume accord is from 30% to 70% by weight of the perfume composition.

In one aspect, the sufficient amount of the second perfume accord is from 30% to 70% by weight of the perfume composition.

In one aspect, the first perfume accord and the second perfume accord are present in the perfume composition in a weight ratio ranging from 3:1 to 1:3.

In one aspect, the first perfume accord and the second perfume accord are present in the perfume composition at a weight ratio of 1:1.

In one aspect, the perception of the second olfactive note after the first olfactive note is at a level sufficient to reduce, prevent, or suppress a reduced perception of the perfume composition by the subject over time.

In one aspect, the perfume composition further comprises a third perfume accord comprising perfuming compounds dominated by a third olfactive note, wherein the third perfume accord is present in the perfume composition in an amount sufficient for the third olfactive note to be perceived by a subject at a third time.

In one aspect, the sufficient amount of the third perfume accord is from 30% to 70% by weight of the perfume composition.

In one aspect, the first perfume accord the second perfume accord, and the third perfume accord are present in the perfume composition at a weight ratio of 1:1:1.

In one aspect, the third olfactive note and the second olfactive note are contrasting notes.

In one aspect, the third olfactive note and the first olfactive note are contrasting notes.

In one aspect, the third time is after the second time.

In one aspect, the third perfume accord comprises perfuming compounds having a volatility ranging from 49 to 0.1 µg/l in air.

In one aspect, the first time is less than one hour after exposure of the subject to the perfuming composition.

In one aspect, the second time is from one to six hours after exposure of the subject to the perfuming composition.

In one aspect, the second time is from one to four hours after exposure of the subject to the perfuming composition.

In one aspect, the third time is from four to six hours after exposure of the subject to the perfuming composition.

In one aspect, the perception of the first olfactive note, the second olfactive note, and the third olfactive note is at a level sufficient to reduce, prevent, or suppress a reduced perception of the perfume composition by the subject over time.

In one aspect, the perception of the third olfactive note after the second olfactive note is at a level sufficient to reduce, prevent, or suppress a reduced perception of the perfume composition by the subject over time.

In one aspect, the first olfactive note is selected from the group consisting of floral, water, green, fruity and citrus olfactive notes.

In one aspect, the second olfactive note is selected from the group consisting of floral, fruity, citrus, sweet, oriental, woody and meringue olfactive notes.

In one aspect, the third olfactive note is selected from the group consisting of floral, fruity, citrus, sweet, oriental, woody and meringue olfactive notes.

In one aspect, the the first perfume accord is dominated by an olfactive note consisting of lemon and the second perfume accord is dominated by a second olfactive note consisting of oriental.

In one aspect, the first perfume accord is dominated by an olfactive note consisting of lemon and the second perfume accord is dominated by an olfactive note consisting of meringue.

In one aspect, the first perfume accord is dominated by an olfactive note consisting of citrus, floral, fruity and green, and the second perfume accord is dominated by an olfactive note consisting of a floral, fruity and sweet.

In one aspect, the first perfume accord is dominated by an olfactive note consisting of citrus and green, the second perfume accord is dominated by an olfactive note consisting of a floral, and fruity, and the third perfume accord is dominated by an olfactive note consisting of floral, fruity, citrus and sweet.

In one aspect, the perfume composition is a pre-formulated perfume composition, and the first perfume accord is added to the pre-formulated perfume composition in an amount sufficient for the first olfactive note to be perceived by the subject at the first time.

In one aspect, the perfume composition is a pre-formulated perfume composition, and the second perfume accord is added to the pre-formulated perfume composition in an amount sufficient for the second olfactive note to be perceived by the subject at the second time.

In one aspect, the perfume composition is a pre-formulated perfume composition, and the third perfume accord is added to the pre-formulated perfume composition in an amount sufficient for the third olfactive note to be perceived by the subject at the third time.

One aspect presented herein provides a manufactured product comprising the perfume composition according to an aspect presented herein.

In one aspect, the manufactured product is selected from the group consisting of a perfume, eau de toilette, home care product and a personal care product.

One aspect presented herein provides a method to reduce, prevent, or suppress a reduced perception of the perfume composition by a subject over time, comprising exposing the subject to a perfume composition according an aspect presented herein.

One aspect presented herein provides a method to reduce, prevent, or suppress a reduced perception of the perfume composition by a subject over time, comprising dispensing sequentially at least partly in the air, the first perfume accord dominated by a first olfactive note followed by the second perfume comprising perfuming compounds forming a second perfume accord dominated by a second olfactive note.

In one aspect, the sequential dispensing is performed using a device.

In one aspect, the first accord and the second accord are physically separated within the device.

DETAILED DESCRIPTION

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Consumers are looking for different sensory experiences, and the perfume industry is constantly seeking for solutions to answer that demand and in particular for ways to prolong the perfume experience over time. The industry is also keen on finding solutions to phenomenon referred to as perfume habituation and perfume adaptation resulting in a decrease of perceived intensity over time. The present disclosure provides a solution to the above-mention problems in particular to the decrease of perfume perception over time and offers a novel solution to improve fragrance longevity and satisfy the consumer needs for new sensory experience.

Odor descriptors are well known and widely use to describe the odor character of a fragrance. Several procedures for describing odor characters are known and have been the object of many publications, and sensory maps for odor descriptors (olfactive note) are largely known and used by the perfumery industry. In 2009 an approach to reach a standard sensory map of perfumery odor perception has been described by M. Zarzo and David Stanton in *Attention, Perception and Psychophysicy,* 2009, 71(2) 225-247. Therefore, in some aspects, a perfume accord can be defined with a number of descriptors.

As used herein, the term "contrasting accords", "contrasting notes" or "contrasting pairs" is meant to designate accords for which the respective dominant olfactive notes are belonging to odor families that are distant from one another. Tools such as the fragrance wheel for instance can be used to define those fragrance families. An exemplar fragrance wheel is shown in FIG. 1.

Figure 1:
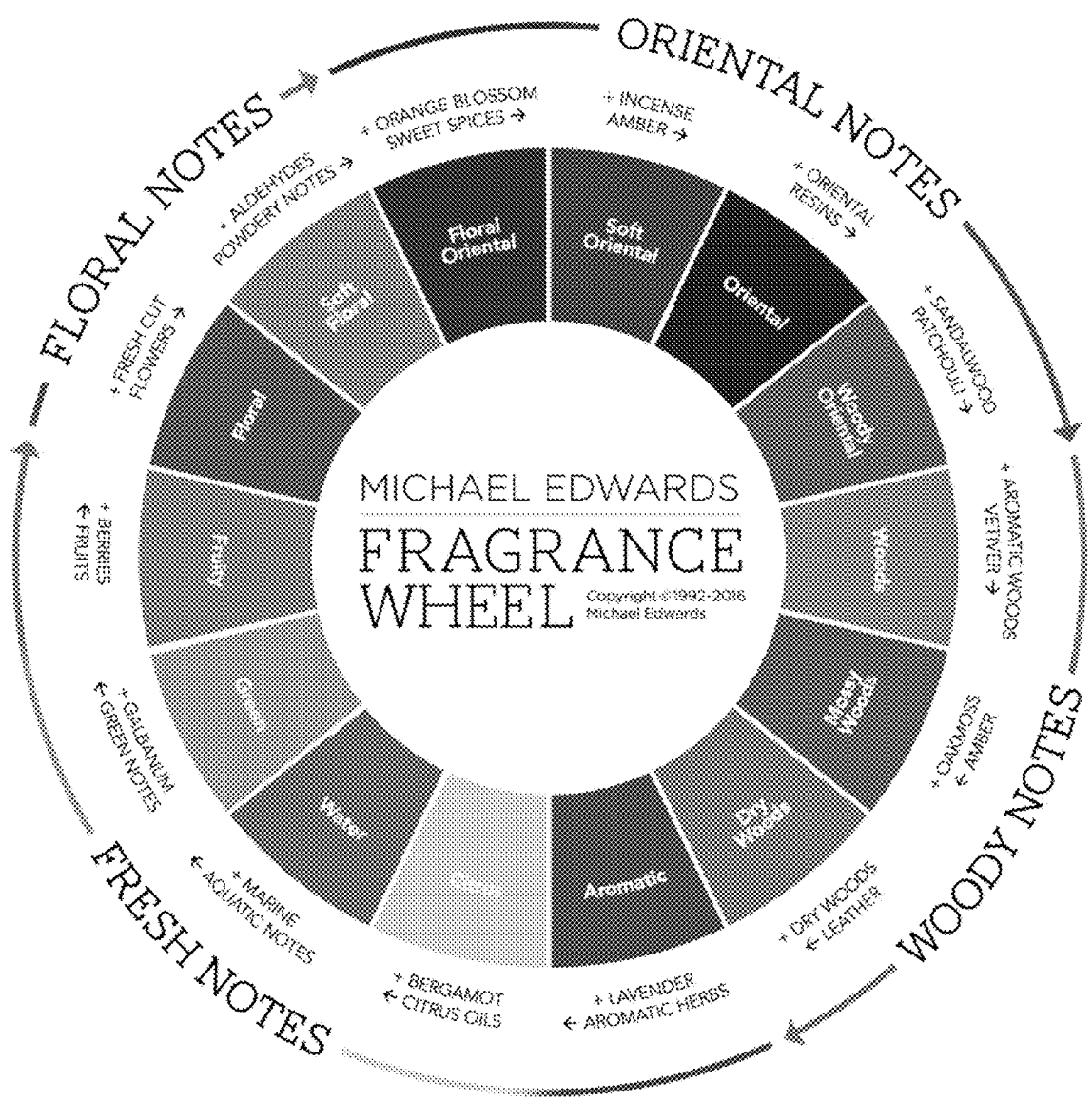
FIG. 1 shows a fragrance wheel showing the inferred relationships among olfactory groups based upon similarities and differences in their odor according to some aspects presented herein.

Referring to the classification shown in FIG. 1, olfactive notes adjacent to each other on the fragrance wheel are not considered contrasting olfactive notes. However, olfactive notes separated by at least one adjacent olfactive note are considered contrasting olfactive notes, wherein the degree of contrast is directly proportional to the degree of separation. For example, by way of illustration, a dry woods olfactive note is opposite to a soft floral olfactive note, and therefore the degree of contrast is considered to be greater than the contrast between a soft floral olfactive note and a soft oriental olfactive note.

Contrasting accords in the context of the invention can be defined as accords for which there is no more than one descriptor shared between the two accords, preferably for which there is no descriptor shared between the two accords. As an example, "sweet" and "aromatic" are strongly correlated and share more than one descriptor. Sweet is also correlated with powdery. Aromatic and powdery are not directly correlated with one another but they both share the correlation with sweet, so they are not contrasting in the context of the invention.

An alternate way to look at contrasting accords is to use the notion of cross-adaptation. Cross-adaptation is well-known in the perfumery technical field and accords for which there is no perceptual cross-adaptation between the accords constitutes contrasting accords.

Alternatively, in some aspects, olfactive notes may be classified as contrasting according to the methods disclosed in Zarzo, J. Sensory Studies, 23 (2008), pg 354-376.

Alternatively, in some aspects, olfactive notes may be classified as contrasting according to the methods disclosed in Zarzo, J. Chemical Senses (2015), pg 305-313.

Alternatively, in some aspects, olfactive notes may be classified as contrasting according to the methods disclosed in Zarzo, J. Chemical Senses 31 (2006), pg 713-724.

Alternatively, in some aspects, olfactive notes may be classified as contrasting according to the methods disclosed in Abe et al, Analytica Chimica 239 (1990), pg 73-85.

Alternatively, in some aspects, olfactive notes may be classified as contrasting according to the methods disclosed in Chastrette et al, Chemical Senses 16 (1991), pg 81-93.

Compositions According to Some Aspects Presented Herein:

Subjects' perceptions of perfume compositions may decline over time. The compositions described herein address the subjects' decline in perception of fragrance in several ways.

Compositions Comprising Contrasting Perfuming Accords:

It has been now surprisingly found that combining contrasting fragrance accords into a single composition may accentuate the differences in the pairing. In particular, the inventors found that the perceived intensity of the resulting mixture of such dissimilar fragrance accords was significantly higher than predicted, based on the intensities of the individual accords; and, that attention to the odor of a mixture of contrasting accords was enhanced and prolonged versus the accords alone.

Accordingly, some aspects described herein provide a perfume composition comprising perfuming compounds forming a first perfume accord dominated by a first olfactive note; and perfuming compounds forming a second perfume accord dominated by a second olfactive note, wherein the first and second olfactive notes are contrasting notes. Additionally, some aspects provide a method to improve perfume intensity perceived by a subject over time, which method comprises, exposing said subject to a composition as defined herein.

A perfume accord is meant to designate a mixture of perfuming ingredients. As used herein, the term "perfuming ingredient" it is meant a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present disclosure, perfume accord also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. In some embodiments, the solvent is not an alcohol. Examples of such solvents are diethyl phthalate, isopropyl myristate, Abalyn® (rosin resins, available from Eastman), benzyl benzoate, ethyl citrate, limonene or other terpenes, or isoparaffins. In some aspects, the solvent is very hydrophobic and highly sterically hindered, like for example Abalyn® or benzyl benzoate.

In some aspects, the perfume comprises less than 30% of solvent. In some aspects, the perfume comprises less than 20%, alternatively less than 10% of solvent, all these percentages being defined by weight relative to the total weight of the perfume. In some aspects, the perfume is essentially free of solvent.

In some aspects, the first perfume comprising perfuming compounds forming a first perfume accord dominated by a first olfactive note, when dispersed into a surrounding space has a given profile. In some aspects, the given profile does not change over time. Similarly, in some aspects the second perfume comprising perfuming compounds forming a second perfume accord dominated by a second olfactive note has a given profile. In some aspects, the given profile does not change over time.

Referring to Examples 1 to 3, the compositions according to the present disclosure advantageously proved to increase the perceived intensity of a perfume, when comparing with the perceived intensity of the individual accords as shown in the examples below. Contrary to what would be expected, namely an intensity for the composition comprising the two accords between the respective intensities of the accord evaluated individually, the composition according to the invention shows increased intensity. Therefore another object of the invention consists of a method to improve perfume intensity perceived by a subject over time, which method comprises exposing said subject to a first perfume accord dominated by a first olfactive note followed by exposure to a second perfume accord dominated by a second olfactive note wherein the first and second olfactive note are contrasting notes.

Moreover, the compositions described herein have also shown to impact noticeability of a perfume when the consumer is exposed to the contrasting accords sequentially. Therefore, a method to improve noticeability of a perfume which comprises dispensing sequentially at least partly in the air, a first perfume comprising perfuming compounds forming a first perfume accord dominated by a first olfactive note followed by a second perfume comprising perfuming compounds forming a second perfume accord dominated by a second olfactive note, wherein the first olfactive and second olfactive notes are contrasting notes, is also an object of the present invention.

In some aspects, the first perfume accord is dominated by an olfactive note selected from the group consisting of floral, water, green, fruity and citrus and the second perfume accord is dominated by an olfactive note selected from the group consisting of oriental, woody and meringue. In an alternate aspect, the first perfume accord is dominated by an olfactive note consisting of lemon and the second perfume accord is dominated by a second olfactive note consisting of an oriental note. In an alternate aspect, the first perfume accord is dominated by an olfactive note consisting of lemon and the second perfume accord is dominated by an olfactive note consisting of a meringue note.

In some aspects, the perfume composition comprises a third contrasting accord. This accord, if used, must contrast with the other two accords in the composition. There must be no perceptual cross-adaptation (reciprocal or non-reciprocal) between either pair of accords in the composition; at least one pair of accords must show either reciprocal or non-reciprocal perceptual enhancement; and, the three accords must be used in the fragrance composition at approximately the same intensity as one another.

In some aspects, the perfume composition further comprises additional ingredients.

Compositions Comprising Contrasting Perfuming Accords Having Different Temporal Release Profiles:

Without intending to be limited to any particular theory, in some aspects, the likelihood of a subject's decreased perception of a fragrance (also referred to herein as habituation) may be greater if the olfactive profile (i.e. the olfactive notes of the perfume composition) does not change, or changes only slightly with time.

By way of illustration, Example 4 describes a perfume composition having an olfactive profile that was consistently reported to be floral, musk and woody for up to 6 hours following application to a surface. It was found that subjects adapted to the perfume composition, in that the perception of the perfume composition decline over time.

In contrast, again referring to Example 4, less adaptation was observed to perfume compositions having an olfactive profile that changes over time.

Accordingly, some aspects provide a perfume composition comprising at least two perfuming accords,
wherein a first perfume accord of the at least two perfuming accords comprises perfuming compounds dominated by a first olfactive note,
wherein a second perfume accord of the at least two perfuming accords comprises perfuming compounds dominated by a second olfactive note,
wherein the first and second olfactive notes are contrasting notes,
wherein the first perfume accord is present in the perfume composition in an amount sufficient for the first olfactive note to be perceived by a subject at a first time,
wherein the second perfume accord is present in the perfume composition in an amount sufficient for the second olfactive note to be perceived by a subject at a second time, and
wherein the perception of the first olfactive note and the second olfactive note is at a level sufficient to reduce, prevent, or suppress a reduced perception of the perfume composition by the subject over time.

In some aspects, the second time is after the first time.

In some aspects, the perfume composition further comprises a third perfume accord comprising perfuming compounds dominated by a third olfactive note, wherein the third perfume accord is present in the perfume composition in an amount sufficient for the third olfactive note to be perceived by a subject at a third time.

In some aspects, the third time is after the second time.

In some embodiments, the perfume composition is the perfume composition described in Table 2.

In some embodiments, the perfume composition is the perfume composition described in Table 3.

In some aspects, the perfume composition further comprises additional ingredients.

In some aspects, the perfume composition is a pre-formulated perfume composition, and the first perfume accord is added to the pre-formulated perfume composition in an amount sufficient for the first olfactive note to be perceived by the subject at the first time.

In some aspects, the perfume composition is a pre-formulated perfume composition, and the second perfume accord is added to the pre-formulated perfume composition in an amount sufficient for the second olfactive note to be perceived by the subject at the second time.

In some aspects, the perfume composition is a pre-formulated perfume composition, and the third perfume accord is added to the pre-formulated perfume composition in an amount sufficient for the third olfactive note to be perceived by the subject at the third time.

In some aspects, the third olfactive note and the second olfactive note are contrasting notes.

In some aspects, the third olfactive note and the first olfactive note are contrasting notes.

In some aspects, there are no perceptual cross-adaptation (reciprocal or non-reciprocal) between either pair of accords in the composition (either between the first and second, or the second and third)

In some embodiments, at least one pair of accords show either reciprocal or non-reciprocal perceptual enhancement.

In some aspects, the first olfactive note is selected from the group consisting of floral, water, green, fruity and citrus olfactive notes.

In some aspects, the second olfactive note is selected from the group consisting of floral, fruity, citrus, sweet, oriental, woody and meringue olfactive notes.

In some aspects, the third olfactive note is selected from the group consisting of floral, fruity, citrus, sweet, oriental, woody and meringue olfactive notes.

In some aspects, the first perfume accord is dominated by an olfactive note consisting of lemon and the second perfume accord is dominated by a second olfactive note consisting of oriental.

In some aspects, the first perfume accord is dominated by an olfactive note consisting of lemon and the second perfume accord is dominated by an olfactive note consisting of meringue.

In some aspects, the first perfume accord is dominated by an olfactive note consisting of citrus, floral, fruity and green, and the second perfume accord is dominated by an olfactive note consisting of a floral, fruity and sweet.

In some aspects, the first perfume accord is dominated by an olfactive note consisting of citrus and green, the second perfume accord is dominated by an olfactive note consisting of a floral, and fruity, and the third perfume accord is dominated by an olfactive note consisting of floral, fruity, citrus and sweet.

In some aspects, the sufficient amount of the first perfume accord is from 30% to 70% by weight of the perfume composition. In some aspects, the sufficient amount of the first perfume accord is from 40% to 70% by weight of the perfume composition. In some aspects, the sufficient amount of the first perfume accord is from 50% to 70% by weight of the perfume composition. In some aspects, the sufficient amount of the first perfume accord is from 60% to 70% by weight of the perfume composition. In some aspects, the sufficient amount of the first perfume accord is from 30% to 60% by weight of the perfume composition. In some aspects, the sufficient amount of the first perfume accord is from 30% to 50% by weight of the perfume composition. In some aspects, the sufficient amount of the first perfume accord is from 30% to 40% by weight of the perfume composition.

In some aspects, the sufficient amount of the first perfume accord is 30%, or 40%, or 50%, or 60%, or 70% by weight of the perfume composition.

In some aspects, the sufficient amount of the second perfume accord is from 30% to 70% by weight of the perfume composition. In some aspects, the sufficient amount of the second perfume accord is from 40% to 70% by weight of the perfume composition. In some aspects, the sufficient amount of the second perfume accord is from 50% to 70% by weight of the perfume composition. In some aspects, the sufficient amount of the second perfume accord is from 60% to 70% by weight of the perfume composition. In some aspects, the sufficient amount of the second perfume accord is from 30% to 60% by weight of the perfume composition. In some aspects, the sufficient amount of the second perfume accord is from 30% to 50% by weight of the perfume composition. In some aspects, the sufficient amount of the second perfume accord is from 30% to 40% by weight of the perfume composition.

In some aspects, the sufficient amount of the second perfume accord is 30%, or 40%, or 50%, or 60%, or 70% by weight of the perfume composition.

In some aspects, the first perfume accord and the second perfume accord are present in the perfume composition in a weight ratio ranging from 3:1 to 1:3. In some aspects, the first perfume accord and the second perfume accord are present in the perfume composition at a weight ratio of 1:1.

In some aspects, the sufficient amount of the third perfume accord is from 30% to 70% by weight of the perfume composition. In some aspects, the sufficient amount of the third perfume accord is from 40% to 70% by weight of the perfume composition. In some aspects, the sufficient amount of the third perfume accord is from 50% to 70% by weight of the perfume composition. In some aspects, the sufficient amount of the third perfume accord is from 60% to 70% by weight of the perfume composition. In some aspects, the sufficient amount of the third perfume accord is from 30% to 60% by weight of the perfume composition. In some aspects, the sufficient amount of the third perfume accord is from 30% to 50% by weight of the perfume composition. In some aspects, the sufficient amount of the third perfume accord is from 30% to 40% by weight of the perfume composition.

In some aspects, the sufficient amount of the third perfume accord is 30%, or 40%, or 50%, or 60%, or 70% by weight of the perfume composition.

In some aspects, the first perfume accord the second perfume accord, and the third perfume accord are present in the perfume composition at a weight ratio of 1:1:1.

Without intending to be limited to any particular theory, the perception of a particular perfume accord depends on a number of factors, such as, for example, the particular mixture of perfuming ingredients, the volatility of the perfuming ingredients, the odor detection threshold of the perfuming ingredients, the concentration of the perfuming ingredients that a subject is exposed to, and the like.

In some embodiments, the first, second, and third perfuming accords, when perceived, are perceived at the same intensity by the subject.

In some embodiments, the time at which a given perfume accord is perceived by the user may be controlled by the relative volatility of a given perfume accord compared to the others in the perfume composition. For example, in some embodiments, the first perfuming accord comprises perfuming ingredients that are more volatile than the perfuming ingredients comprising the second, or third perfume accords. Consequently, the first perfume accord is perceived by the subject at a first time that is before the time the second perfume accord is perceived. Similarly, in some embodiments, the second perfuming accord comprises perfuming ingredients that are more volatile than the perfuming ingredients comprising the third perfume accord. Consequently, the second perfume accord is perceived by the subject at a time second time that is before the time the third perfume accord is perceived. Similarly, the third perfuming accord comprises perfuming ingredients that are less volatile than the perfuming ingredients comprising the second perfume accord. Consequently, the third perfume accord is perceived by the subject at a time second time that is after the time the second perfume accord is perceived.

In some aspects, the first perfume accord comprises perfuming compounds having a volatility ranging from 70,000 to 100 µg/l in air. In some aspects, perfuming compounds having a volatility ranging from 70,000 to 100 µg/l in air are referred to as "top notes".

In some aspects, the second perfume accord comprises perfuming compounds having a volatility ranging from 99 to 50 µg/l in air. In some aspects, perfuming compounds having a volatility ranging from 99 to 50 µg/l in air are referred to as "middle notes".

In some aspects, the third perfume accord comprises perfuming compounds having a volatility ranging from 49 to 0.1 µg/l in air. In some aspects, perfuming compounds having a volatility ranging from 49 to 0.1 µg/l in air are referred to as "bottom notes".

In some aspects, the first perfume accord comprises perfuming compounds having a vapor pressure greater than 0.1 mm Hg. In some aspects, perfuming compounds having a vapor pressure greater than 0.1 mm Hg are referred to as "top notes".

In some aspects, the second perfume accord comprises perfuming compounds having a vapor pressure between 0.1 mm Hg and 0.001 mm Hg. In some aspects, perfuming compounds having a vapor pressure between 0.1 mm Hg and 0.001 mm Hg are referred to as "middle notes".

In some aspects, the third perfume accord comprises perfuming compounds having a vapor pressure less than 0.001 mm Hg. In some aspects, perfuming compounds having a vapor pressure less than 0.001 mm Hg are referred to as "bottom notes".

Tables 4 to 10 describe top, middle and bottom note perfuming compounds for watery, green, fruity, citrus, sweet, gourmand and woody notes respectively.

In some aspects, the perception of the second olfactive note after the first olfactive note is at a level sufficient to reduce, prevent, or suppress a reduced perception of the perfume composition by the subject over time.

In some aspects, the perception of the first olfactive note, the second olfactive note, and the third olfactive note is at a level sufficient to reduce, prevent, or suppress a reduced perception of the perfume composition by the subject over time.

In some aspects, the perception of the third olfactive note after the second olfactive note is at a level sufficient to reduce, prevent, or suppress a reduced perception of the perfume composition by the subject over time.

Accordingly, some aspects provide a method to reduce, prevent, or suppress a reduced perception of the perfume composition by a subject over time, comprising exposing the subject to a perfume composition according an aspect presented herein.

In some aspects, the first time is less than one hour after exposure of the subject to the perfuming composition. In some aspects, the first time is 60, or 55, or 50, or 45, or 40, or 35, or 30, or 25, or 20, or 15 minutes after exposure of the subject to the perfuming composition.

In some aspects, the second time is from one to six hours after exposure of the subject to the perfuming composition. In some aspects, the second time is from one to five hours after exposure of the subject to the perfuming composition. In some aspects, the second time is from one to four hours after exposure of the subject to the perfuming composition. In some aspects, the second time is from one to three hours after exposure of the subject to the perfuming composition. In some aspects, the second time is from one to two hours after exposure of the subject to the perfuming composition. In some aspects, the second time is from two to six hours after exposure of the subject to the perfuming composition. In some aspects, the second time is from three to six hours after exposure of the subject to the perfuming composition. In some aspects, the second time is from four to six hours after exposure of the subject to the perfuming composition. In some aspects, the second time is from five to six hours after exposure of the subject to the perfuming composition. In some aspects, the second time is 1, or 1.5, or 2, or 2.5, or 3, or 3.5, or 4, or 4.5, or 5, or 5.5, or 6 six hours after exposure of the subject to the perfuming composition.

In some aspects, the second time is from one to four hours after exposure of the subject to the perfuming composition.

In some aspects, the third time is from four to six hours after exposure of the subject to the perfuming composition. In some aspects, the third time is from four to five hours after exposure of the subject to the perfuming composition. In some aspects, the third time is from five to six hours after exposure of the subject to the perfuming composition. In some aspects, the third time is 4, or 4.5, or 5, or 5.5, or 6 six hours after exposure of the subject to the perfuming composition.

Devices and Applications

In some aspects, the time at which a given perfume accord is perceived by the user may be controlled by dispensing the given perfume accord at a given time. For example, the first perfume accord may be dispensed at the first time, the second perfume accord may be dispensed at the second time, and so on. In some embodiments, the subject does not perceive a given perfume accord until it is dispensed.

Accordingly, some aspect presented herein provide a method to reduce, prevent, or suppress a reduced perception of the perfume composition by a subject over time, comprising dispensing sequentially at least partly in the air, the first perfume accord dominated by a first olfactive note followed by the second perfume comprising perfuming compounds forming a second perfume accord dominated by a second olfactive note.

In some aspects, the sequential dispensing is performed using a device configured to sequentially emanate separate fragrances at timed intervals from each other. Devices suitable for this include the AIRWICK® SYMPHONIA device which is configured to receive two separate bottles of fragrance and sequentially direct heat toward each bottle to accelerate the evaporation of fragrance therefrom. In such a device the fragrances contained in each bottle can be different to facilitate a consumer being able to notice the sequential nature of the fragrance emanation.

U.S. Patent Application Publication No. 2013/0156408 A1 discloses an example of a device configured to sequentially emanate separate fragrances at timed intervals from each other.

U.S. Patent Application Publication No. 2013/0156408 A1 discloses an example of methods to sequentially emanate separate fragrances at timed intervals from each other.

U.S. Patent Application Publication No. 2015/0098860 A1 discloses an example of methods to sequentially emanate separate fragrances at timed intervals from each other.

In some aspects, the device comprises dispensing means for dispersing sequentially in the air volatile compositions and a composition as defined in any of the above-described aspects. In some aspects, the device is such that the first accord and the second accord are physically separated by separating means. According to one aspect, the device is an air-freshener. By sequentially diffusing contrasting accords, the intensity of the perfume can be improved over time.

In some aspects, the first time is 60, or 55, or 50, or 45, or 40, or 35, or 30, or 25, or 20, or 15 minutes.

In some aspects, the second time is 1, or 1.5, or 2, or 2.5, or 3, or 3.5, or 4, or 4.5, or 5, or 5.5, or 6 six hours.

In some aspects, the third time is 4, or 4.5, or 5, or 5.5, or 6 six hours.

The compositions of the present disclosure can be used for different applications. According to some aspects, the perfume composition according to the invention consists of an air freshener.

One aspect presented herein provides a manufactured product comprising the perfume composition according to an aspect presented herein. In one aspect, the manufactured product is selected from the group consisting of a perfume, eau de toilette, home care product and a personal care product.

The present invention is best illustrated but is not limited to the following examples.

EXAMPLES

Example 1: Sensory Evaluation of Perceived Perfume Intensity with Sequential Exposure to Contrasting Accords Vs Non Contrasting Accords For this example, 3 perfume accords were prepared: a lemon accord (A1); a lime accord (A2); and, an oriental accord (C1). The lemon accord and lime accords are non-contrasting accords, whereas the lemon and oriental accords are contrasting accords.

Protocol:

Each accord was applied to a cellulose type air freshener and placed in an evaluation booth. A panel was then asked to rate the intensity of the odor in each booth. The test was repeated later the same day. The sample preparation and set-up was identical to the first test but there was one important difference: each assessor was asked to wear a small device for 15 minutes prior to the evaluation. The device was a small plastic holder that could be clipped onto the assessors clothing, the holder contained a cellulose pad that was impregnated with the lemon accord. In this way we were able to adapt the assessors to the lemon accord.

Figure 2:
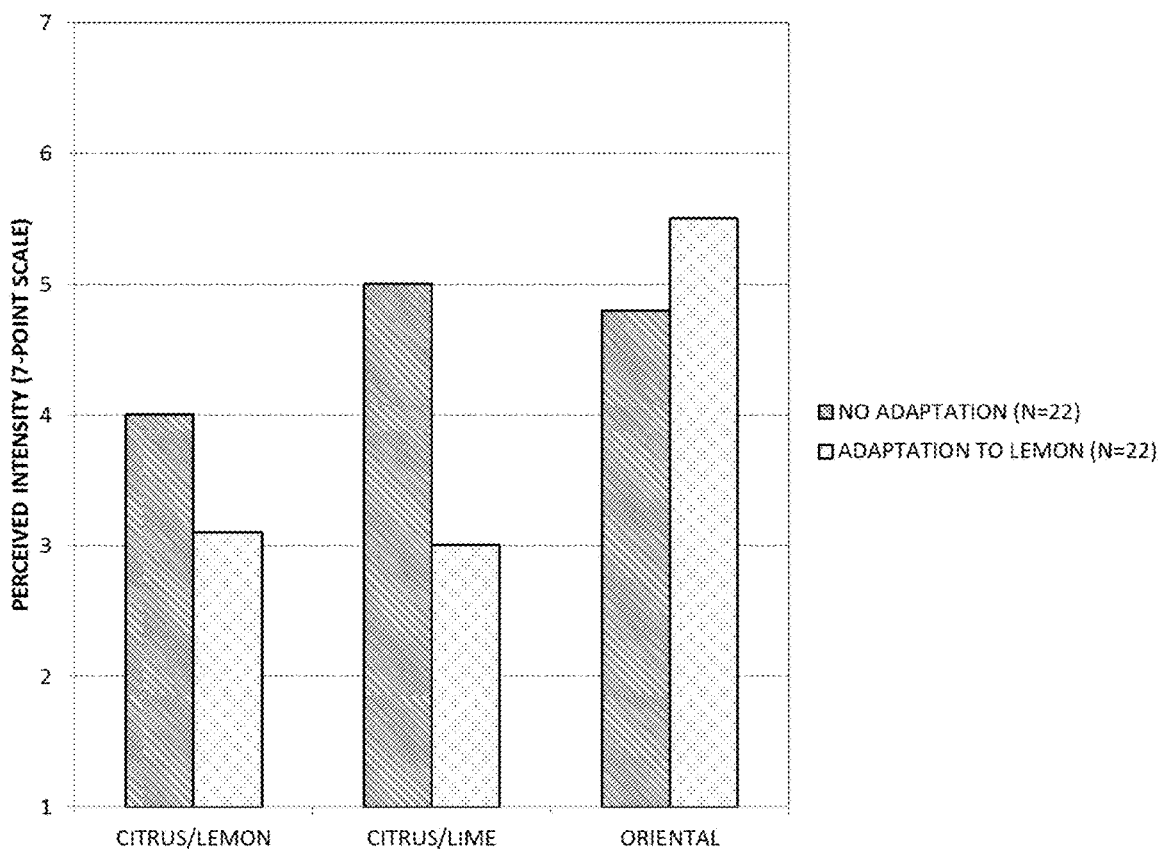
FIG. 2 shows a graph of perceived perfume intensities after sequential exposure to contrasting and non-contrasting accords, according to some aspects presented herein.

The results of the two tests are illustrated in FIG. 2 and are markedly different. The perceived intensity of the lemon accord was significantly suppressed after adaptation to the lemon accord (self-adaptation). The perceived intensity of the lime accord (non-contrasting accord if compared to lemon) was also strongly suppressed after adaptation to the lemon accord (significant cross-adaptation*). On the other hand, the perceived intensity of the oriental accord (contrasting accord compare to lemon) was increased/enhanced after adaptation to the lemon accord. The lemon accord and oriental accord would meet the definition of "contrasting fragrance accords"—there is no cross-adaptation and there is a perceptual enhancement.

Figure 3:
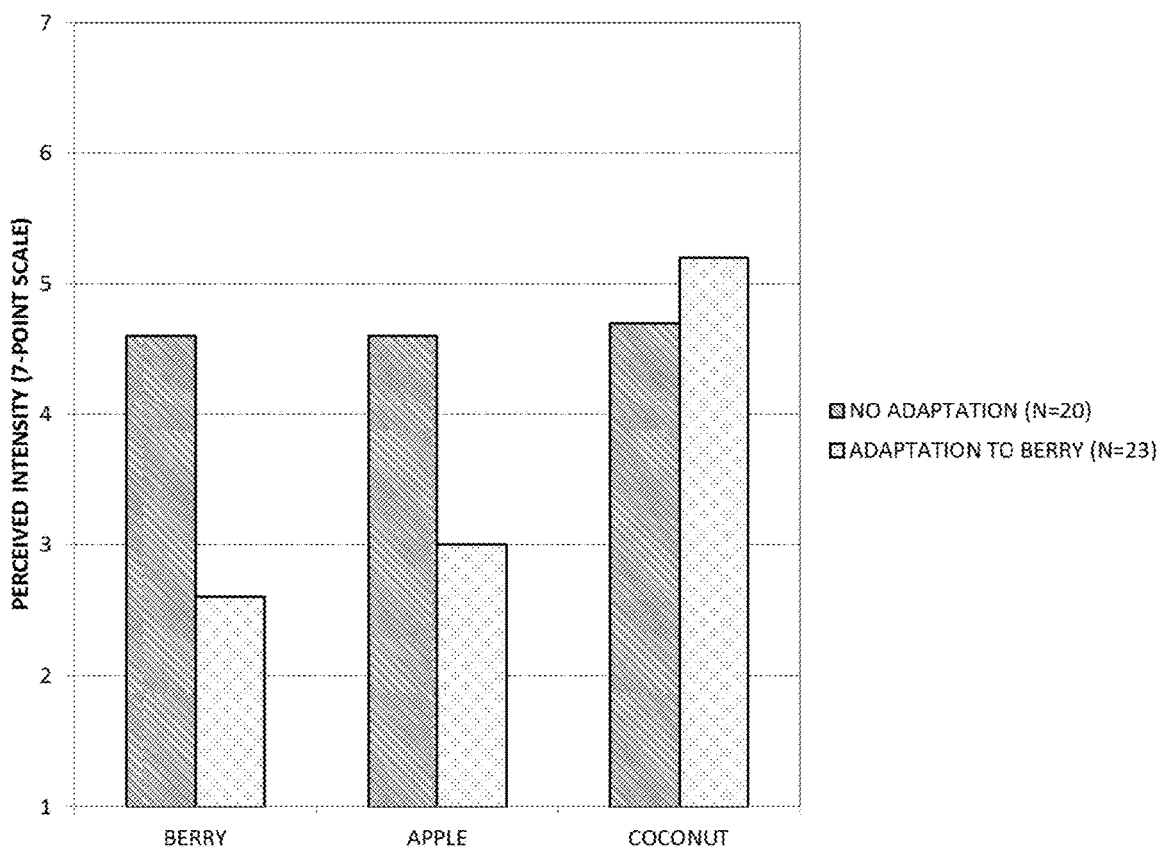
FIG. 3 shows a graph of perceived perfume intensities after sequential exposure to contrasting and non-contrasting accords, according to some aspects presented herein.
Figure 4:
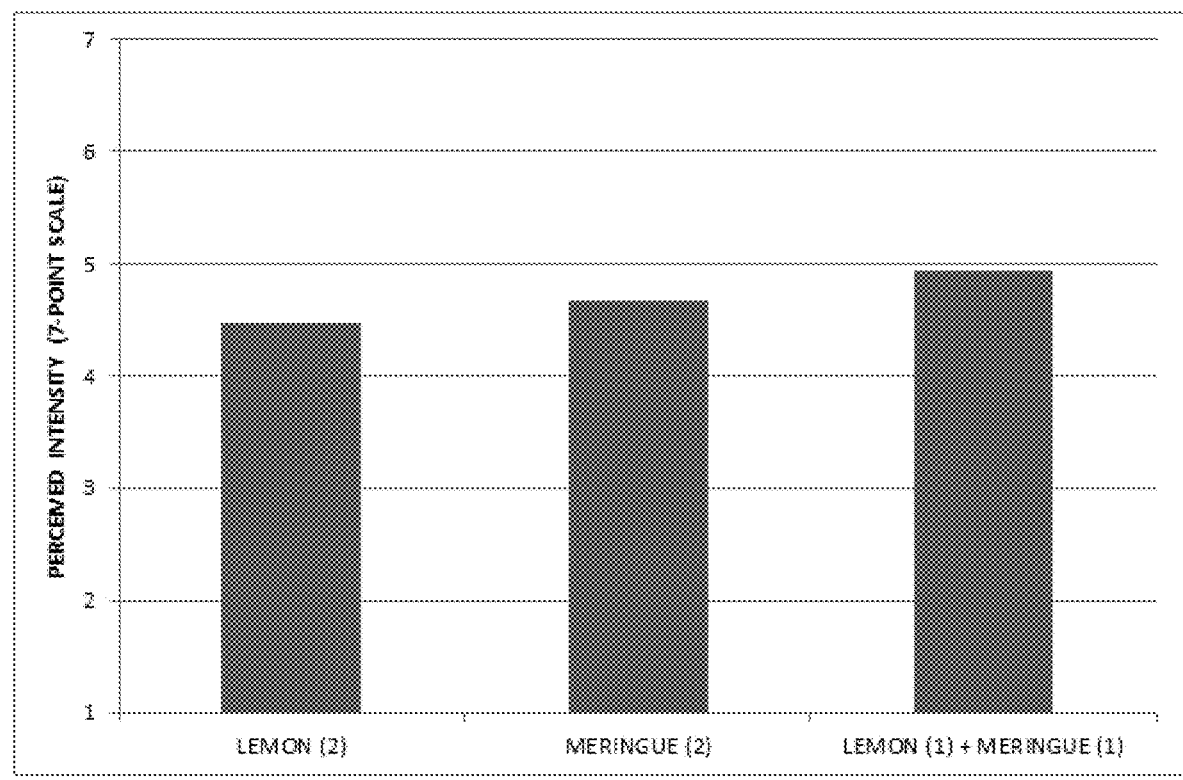
FIG. 4 shows a graph of perceived perfume intensities after sequential exposure to contrasting and non-contrasting accords, according to some aspects presented herein.

Example 2: Sensory Evaluation of Perceived Perfume Intensity with Sequential Exposure to Contrasting Accords Vs Non Contrasting Accords The protocol described in Example 1 was repeated using a larger panel and different accords. Accords used were a berry accord (A1) and a coconut accord (C1). There was also used an accord that would be "complementary" to the berry accord, that is one that is noticeably different (more different than lime from lemon) but which shares some olfactive quality—there was used an apple accord for this purpose (B1). Results are illustrated in FIG. 3. The berry accord showed a strong self-adapting effect, cross-adaptation with the apple accord and no cross-adaptation with the coconut accord. Furthermore, there was an enhancement of the coconut accord after adaptation to the berry.

Example 3: Sensory Evaluation of Perceived Perfume Intensity of a Perfume Composition According to Some Aspects Presented Herein A sensory test was conducted with 24 panelists. Two contrasting fragrance accords were used, namely "LEMON" (A1) and "MERINGUE" (C1). Three identical odor evaluation booths were set up as follows: one booth contained two 5 cm×5 cm cellulose pads, each impregnated with 2 g of the "LEMON" accord; a second booth contained two 5 cm×5 cm cellulose pads, each impregnated with 2 g of the "MERINGUE" accord; a third booth contained one 5 cm×5 cm cellulose pad impregnated with 2 g of the "LEMON" accord and one 5 cm×5 cm cellulose pad impregnated with the "MERINGUE" accord. Panelists were asked to rate the intensity of the odors in each booth. Normally, it could have been expected that the intensity of the mixture "LEMON+MERINGUE" would fall between the intensity of the LEMON only and MERINGUE only; however, surprisingly the intensity of the mixture was significantly stronger than the intensity of either single accord. Results are illustrated in FIG. 3.

Also, it was mentioned by panellist that the citrus aspects were more noticeable when paired with the "meringue" than when smelled alone. This view was echoed by several of the professional evaluators that smelled the samples.

Example 4: Sensory Evaluation of Perceived Perfume Intensity of a Fine Fragrance Perfume Composition According to Some Aspects Presented Herein A sensory test was conducted with 22 to 24 panelists in each session, comparing the three fine fragrances shown in three different sesasions, set forth in Tables 1-3 below:

TABLE 1

| Test Attention Modulation Fragrance "HAF A": | |
|---|---|
| Ingredient Name | Parts |
| Naphtho[2,1-b]furan, dodecahydro-3a,6,6,9a-tetramethyl-, [3aR-(3a.alpha.,5a.beta., 9a.alpha.,9b.beta)] @10% DIPG | 15 |
| Benzyl Acetate | 5 |
| Ethoxymethyl-cyclododecyl ether | 10 |
| 3-(4-tert-butylphenyl)propanal | 5 |
| (Z)-3-Methyl-2-(2-pentenyl)-2-cyclopenten-1-one | 1 |
| 3,7-dimethyl-2,6-octadienal @ 10% DIPG | 3 |
| 3,7-dimethyloct-6-enyl acetate | 10 |
| 1-(2,6,6-trimethyl-1-cyclohex-2-enyl)but-3-en-1-one @ 10% DIPG | 3 |
| (E)-1-(2,6,6-trimethyl-1-cyclohexa-1,3-dienyl)but-2-en-1-one @10% DIPG | 3 |
| 5-hexyloxolan-2-one | 2 |
| (6E)-3,7-dimethylnona-1,6-dien-3-ol | 35 |
| 1,4-dioxacycloheptadecane-5,17-dione | 50 |
| 1,3,4,6,7,8-hexahydro-4,6,6,7,8,8-hexamethylcyclopenta(g)-2-benzopyran MIP EXTRA | 70 |
| (Z)-3,7-Dimethyl-2,6-octadien-1-ol | 7 |
| GRAPEFRUIT OIL | 10 |
| methyl 3-oxo-2-pentylcyclopentaneacetate | 100 |
| 3-(1,3-benzodioxol-5-yl)-2-methylpropanal | 20 |
| HYDROXYCITRONELLAL SYNTH P FAB | 25 |

TABLE 1-continued

Test Attention Modulation Fragrance "HAF A":

| Ingredient Name | Parts |
|---|---|
| INDOLE @ 1% DIPG | 5 |
| 7-acetyl, 1,2,3,4,5,6,7,8-octahydro-1,1,6,7-tetramethyl naphthalene | 35 |
| JASMIN PAYS FIR ABSOLUE @ 10% DIPG | 3 |
| 6-[(E)-pent-2-enyl]oxan-2-one @10% DIPG | 14 |
| LEMON OIL SFUMA PRIMOFIORE | 10 |
| 3-(4-tert-butylphenyl)butanal | 40 |
| MANDARIN INCOL DM | 15 |
| METHYL ANTHRANILATE DIST @1% DIPG | 4 |
| methyl 2,4-dihydroxy-3,6-dimethylbenzoate @10 DIPG | 3 |
| TAGETES OIL @10% DIPG | 2 |
| 5-heptyloxolan-2-one | 5 |
| (E)-4-methyldec-3-en-5-ol | 6 |
| 2,4-dimethylcyclohex-3-ene-1-carbaldehyde @10% DIPG | 4 |
| | 500 |

TABLE 2

Test Attention Modulation Fragrance "HAF A2":

| Ingredient Name | Parts |
|---|---|
| Naphtho[2,1-b]furan, dodecahydro-3a,6,6,9a-tetramethyl-, [3aR-(3a.alpha.,5a.beta.,9a.alpha.,9b.beta)] @10% DIPG | 15 |
| Benzyl Acetate | 5 |
| Ethoxymethyl-cyclododecyl ether | 10 |
| 3-(4-tert-butylphenyl)propanal | 5 |
| (Z)-3-Methyl-2-(2-pentenyl)-2-cyclopenten-1-one | 1 |
| 3,7-dimethyl-2,6-octadienal @ 10% DIPG | 3 |
| 3,7-dimethyloct-6-enyl acetate | 10 |
| 1-(2,6,6-trimethyl-1-cyclohex-2-enyl)but-3-en-1-one @ 10% DIPG | 3 |
| (E)-1-(2,6,6-trimethyl-1-cyclohexa-1,3-dienyl)but-2-en-1-one @10% DIPG | 3 |
| 5-hexyloxolan-2-one | 2 |
| (6E)-3,7-dimethylnona-1,6-dien-3-ol | 35 |
| ETHYL PRANILE @10% DIPG | 5 |
| 1,4-dioxacycloheptadecane-5,17-dione | 50 |
| 1,3,4,6,7,8-hexahydro-4,6,6,7,8,8-hexamethylcyclopenta(g)-2-benzopyran 70 MIP EXTRA | 50 |
| (Z)-3,7-Dimethyl-2,6-octadien-1-ol | 7 |
| GRAPEFRUIT OIL | 10 |
| methyl 3-oxo-2-pentylcyclopentaneacetate | 100 |
| 3-(1,3-benzodioxol-5-yl)-2-methylpropanal | 20 |
| HYDROXYCITRONELLAL SYNTH P FAB | 38 |
| INDOLE @ 1% DIPG | 5 |
| 7-acetyl, 1,2,3,4,5,6,7,8-octahydro-1,1,6,7-tetramethyl naphthalene | 35 |
| JASMIN PAYS FIR ABSOLUE @ 10% DIPG | 3 |
| 6-[(E)-pent-2-enyl]oxan-2-one @10% DIPG | 14 |
| LEMON OIL SFUMA PRIMOFIORE | 10 |
| 3-(4-tert-butylphenyl)butanal | 40 |
| MANDARIN INCOL DM | 15 |
| METHYL ANTHRANILATE DIST @1% DIPG | 4 |
| methyl 2,4-dihydroxy-3,6-dimethylbenzoate @10 DIPG | 3 |
| TAGETES OIL @10% DIPG | 2 |
| 5-heptyloxolan-2-one | 5 |
| (E)-4-methyldec-3-en-5-ol | 6 |

TABLE 2-continued

Test Attention Modulation Fragrance "HAF A2":

| Ingredient Name | Parts |
|---|---|
| VANILLIN NAT NFB LC @10% DIPG | 2 |
| 2,4-dimethylcyclohex-3-ene-1-carbaldehyde @10% DIPG | 4 |
| | 520 |

TABLE 3

Reference Fragrance "HAF 1":

| Ingredient Name | Parts |
|---|---|
| Ambrettolide | 5 |
| 3a,6,6,9a-tetramethyl-2,4,5,5a,7,8,9,9b-octahydro-1H-benzo[e][1]benzofuran | 10 |
| Benzyl Salicylate | 40 |
| Ethoxymethyl-cyclododecyl ether | 20 |
| Dartanol | 15 |
| 1,4-dioxacycloheptadecane-5,17-dione | 77 |
| Firsantol | 10 |
| 1,3,4,6,7,8-hexahydro-4,6,6,7,8,8-hexamethylcyclopenta(g)-2-benzopyran 70 MIP EXTRA | 120 |
| methyl 3-oxo-2-pentylcyclopentaneacetate | 80 |
| Hydroxycitronellal Synth P FAB | 30 |
| Indole @ 10% DIPG | 2 |
| 7-acetyl, 1,2,3,4,5,6,7,8-octahydro-1,1,6,7-tetramethyl naphthalene | 180 |
| Jasmin Sambac Fir absolue @ 10% DIPG | 5 |
| 5-Ethyl-5-phenylhydantoin | 10 |
| Pipol Salicylate | 10 |
| (E)-3,3-dimethyl-5-(2,2,3-trimethyl-3-cyclopenten-1-yl)-4-penten-2-ol | 25 |
| 3-methyl-5-(2,2,3-trimethyl-1-cyclopent-3-enyl)pentan-2-ol | 30 |
| 1-(2,6,10-TRIMETHYL-1(2),5,9-CYCLODODECATRIEN-1-YL)-1-ETHANONE + 1-(6,10-DIMETHYL-2-METHYLENE-5,9-..)-1-E ... | 30 |
| 5-heptyloxol an-2-one | 1 |
| | 700 |

The fine fragrances were applied to glass slides, which were maintained at 32 degrees Celsius. The olfactive profile and perceived global intensity of the fragrances were evaluated at 15 min, 1 hour, 2 hours, 4 hours, and 6 hours after application to the glass surfaces, by randomly presenting the slides.

The panelists were asked to describe the olfactive profile by selecting the three most dominant descriptors (out of 7 presented: Green, Citrus, Fruity, Floral, Woody, Musk, Sweet/Gourmand). Panelists were also able to mention when they perceived nothing (i.e., were not able to describe the olfactive profile).

The panelists were asked to rate the perceived global intensity of the fragrances at 15 min, 1 hour, 2 hours, 4 hours, and 6 hours after application to the glass surfaces, by randomly presenting the slides.

Adaptation was determined by applying the fragrance to a cellulose pad, and presenting the fragrance to the panelist for two minutes before the glass slides were presented again to the panelists.

Figure 5:
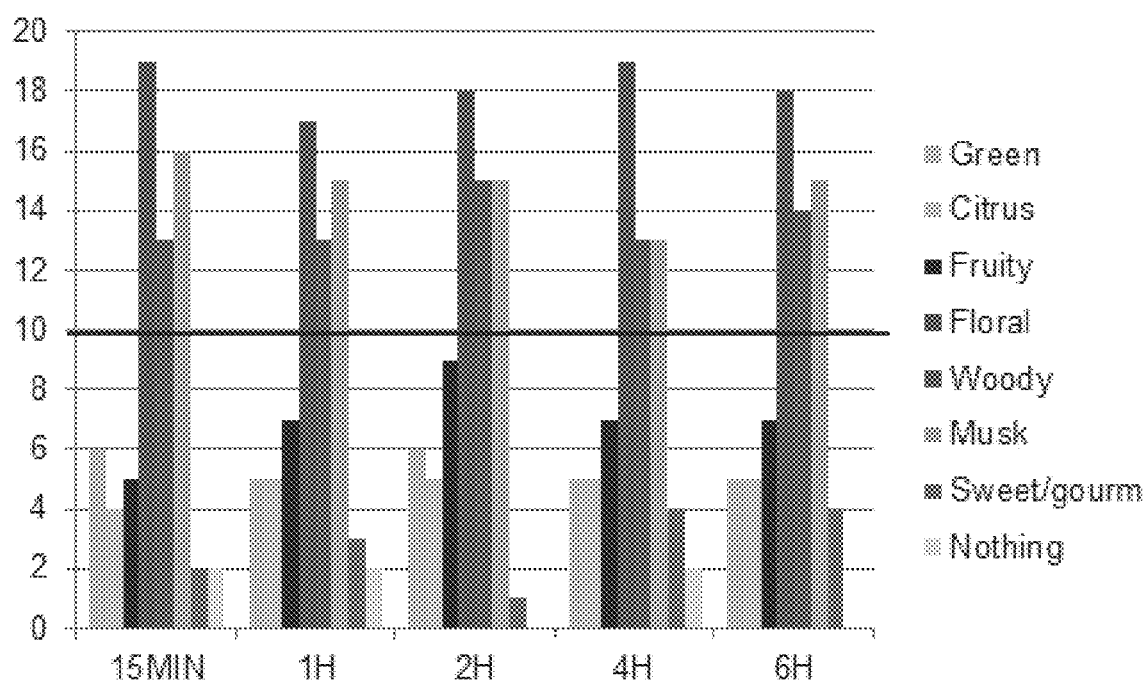
FIG. 5 shows the olfactive profile of a reference fine fragrance at the times indicated. The bars at each time point, moving from left to right, represent the number of subjects that perceived green, citrus, fruity, floral, woody, musk, or sweet/gourmand notes, or lack of any note.

The Reference Fine Fragrance:

Referring to FIG. 5, the olfactive profile did not appear to change over time, wherein the panelists reported a Floral, Musk, and Woody profile at all time points. The horizontal line depicts the limit of a random selection of the terms. 46% of the panelists reported no change in olfactive profile, whilst 46% of the panelists reported 2 to 4 changes in olfactive profile, and none of the panelists reported a maximum of 4 changes in olfactive profile.

Figure 6:
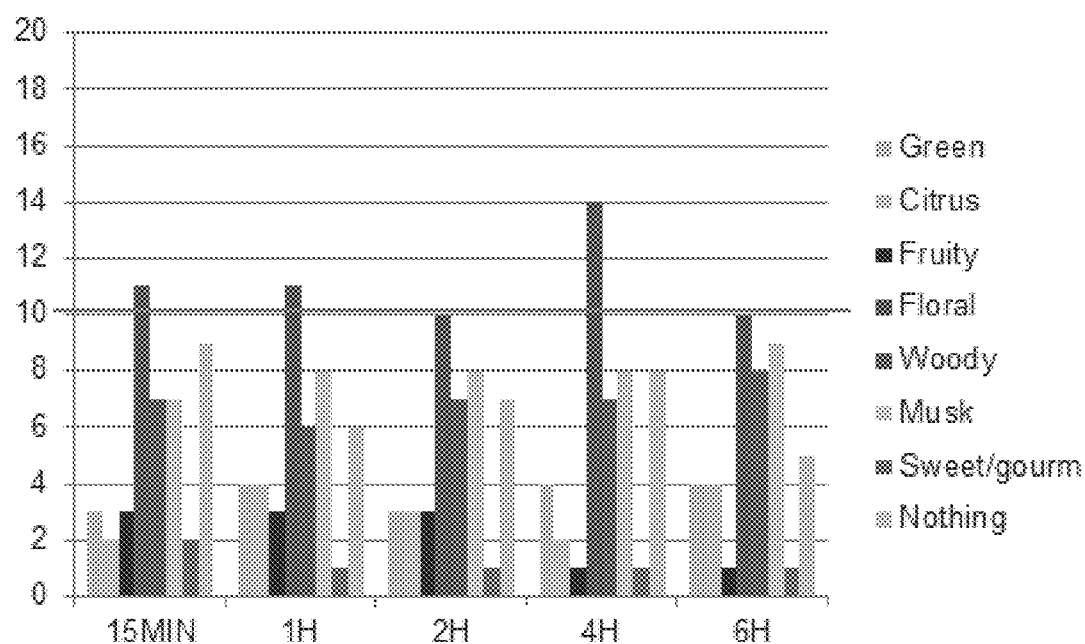
FIG. 6 shows the olfactive profile of a reference fine fragrance at the times indicated, after a subject has been exposed to the fine fragrance for two minutes. The bars at each time point, moving from left to right, represent the number of subjects that perceived green, citrus, fruity, floral, woody, musk, or sweet/gourmand notes, or lack of any note.

Referring to FIG. 6, the perception of the reference fine fragrance declined significantly following a two minute exposure to the fragrance. Before exposure, 65% of the selected terms were above chance, compared to 15% after exposure.

Figure 7:
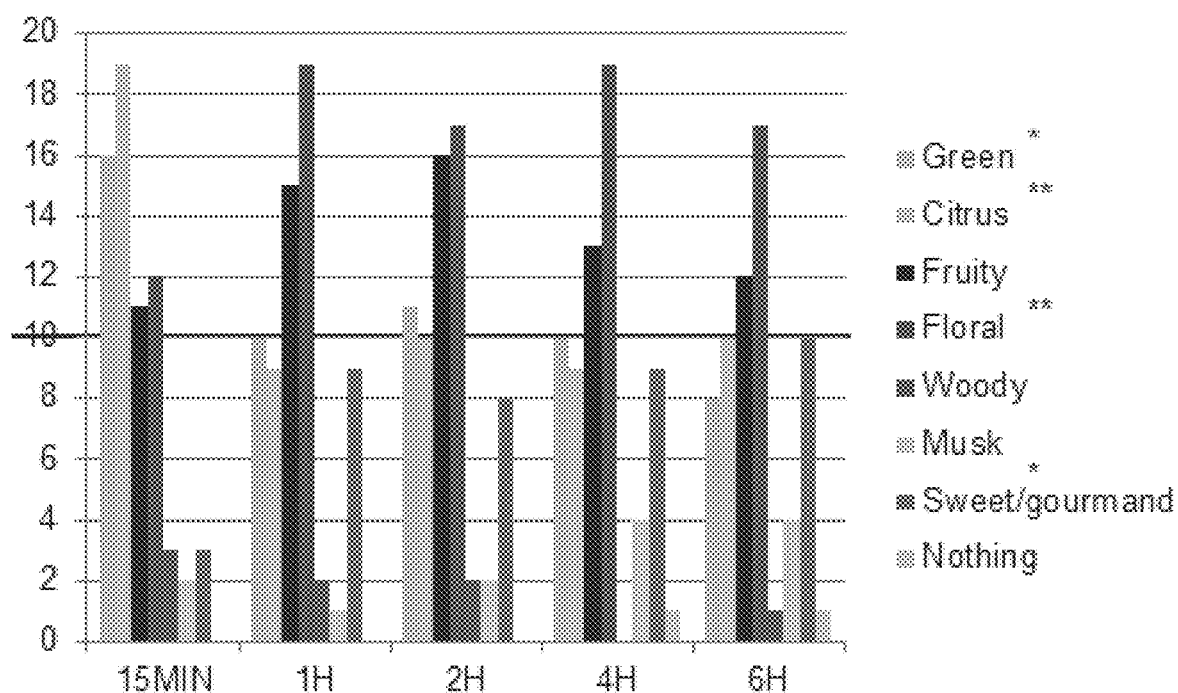
FIG. 7 shows the olfactive profile of fine fragrance according to one aspect presented herein at the times indicated. The bars at each time point, moving from left to right, represent the number of subjects that perceived green, citrus, fruity, floral, woody, musk, or sweet/gourmand notes, or lack of any note.

The Attention Modulation Fragrance "HAF A":

Referring to FIG. 7, the olfactive profile changed or switched, wherein the panelists reported a Citrus/Green profile at 15 min, a Floral/Fruity profile at 1 to 4 hours, and a Floral/Fruity/Citrus/Sweet profile at 6 hours. The horizontal line depicts the limit of a random selection of the terms. Only 18% of the panelists reported no change in olfactive profile, whilst 73% of the panelists reported 2 to 4 changes in olfactive profile, and 23% of the panelists reported a maximum of 4 changes in olfactive profile.

Figure 8:
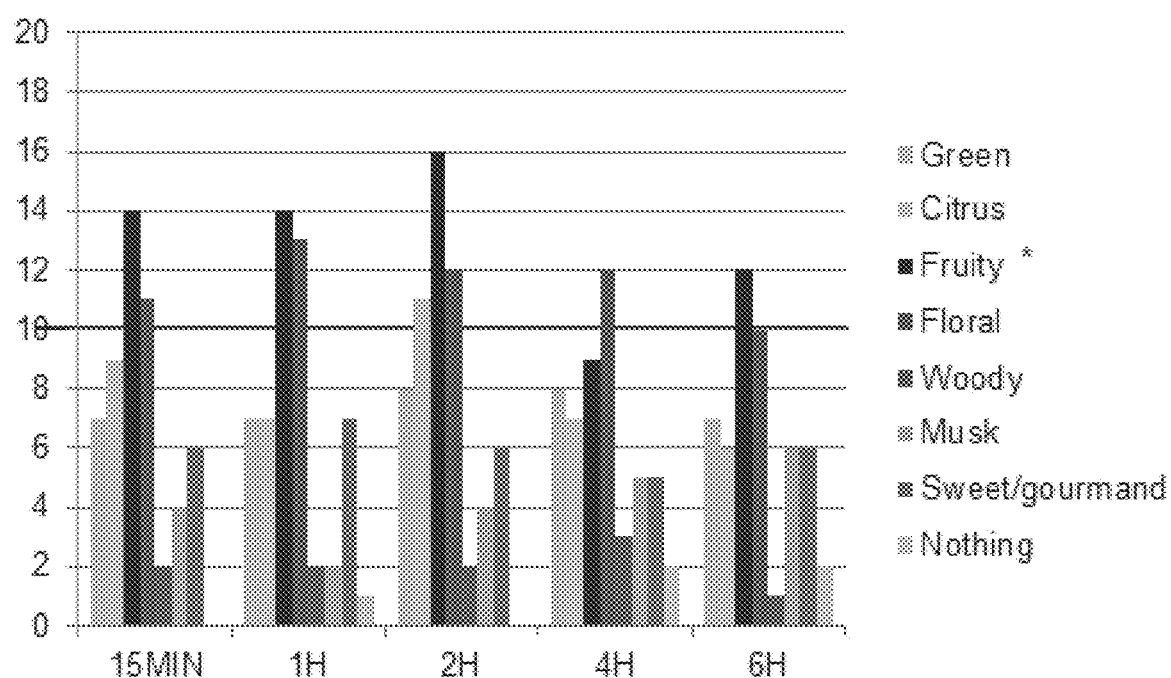
FIG. 8 shows the olfactive profile of a fine fragrance according to one aspect presented herein at the times indicated, after a subject has been exposed to the fine fragrance for two minutes. The bars at each time point, moving from left to right, represent the number of subjects that perceived green, citrus, fruity, floral, woody, musk, or sweet/gourmand notes, or lack of any note.

Referring to FIG. 8, the perception of the attention modulation fine fragrance did not decline as much, compared to the decline observed with the reference fragrance following a two minute exposure to the fragrance. After exposure, 38% of the selected terms were above chance compared to only 15% for the reference fragrance.

Figure 9:
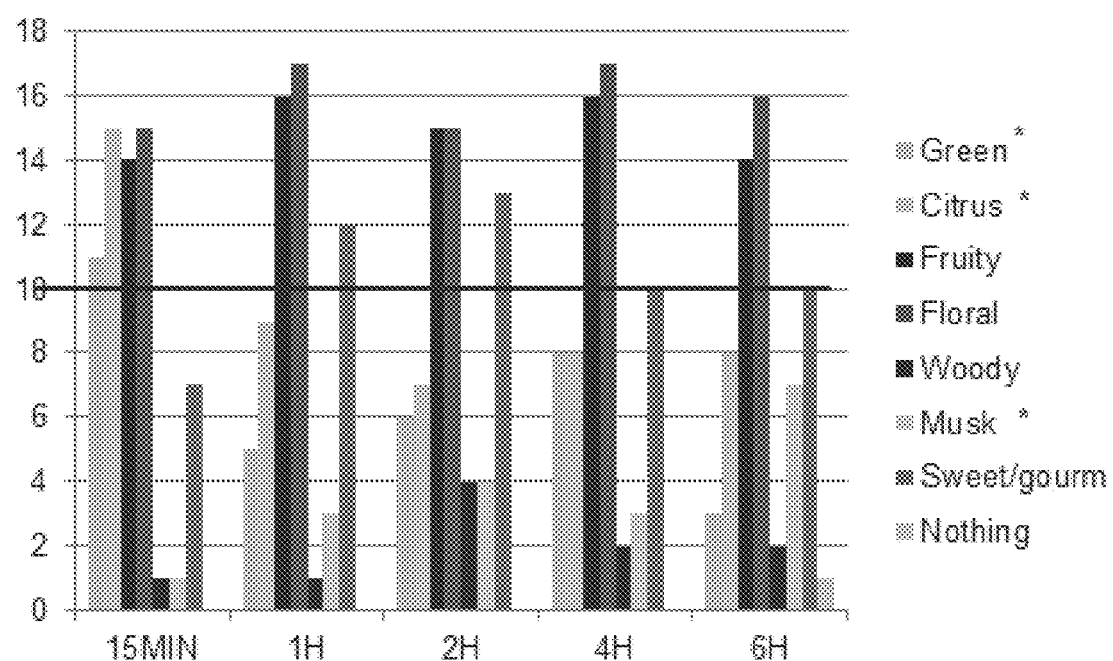
FIG. 9 shows the olfactive profile of fine fragrance according to one aspect presented herein at the times indicated. The bars at each time point, moving from left to right, represent the number of subjects that perceived green, citrus, fruity, floral, woody, musk, or sweet/gourmand notes, or lack of any note.

The Attention Modulation Fragrance "HAF A2":

Referring to FIG. 9, the olfactive profile changed or switched, wherein the panelists reported a Citrus/Floral/Fruity/Green profile at 15 min, and a Floral/Fruity/Sweet profile at 1 to 6 hours. The horizontal line depicts the limit of a random selection of the terms. Only 9% of the panelists reported no change in olfactive profile, whilst 82% of the panelists reported 2 to 4 changes in olfactive profile, and 34% of the panelists reported a maximum of 4 changes in olfactive profile.

Figure 10:
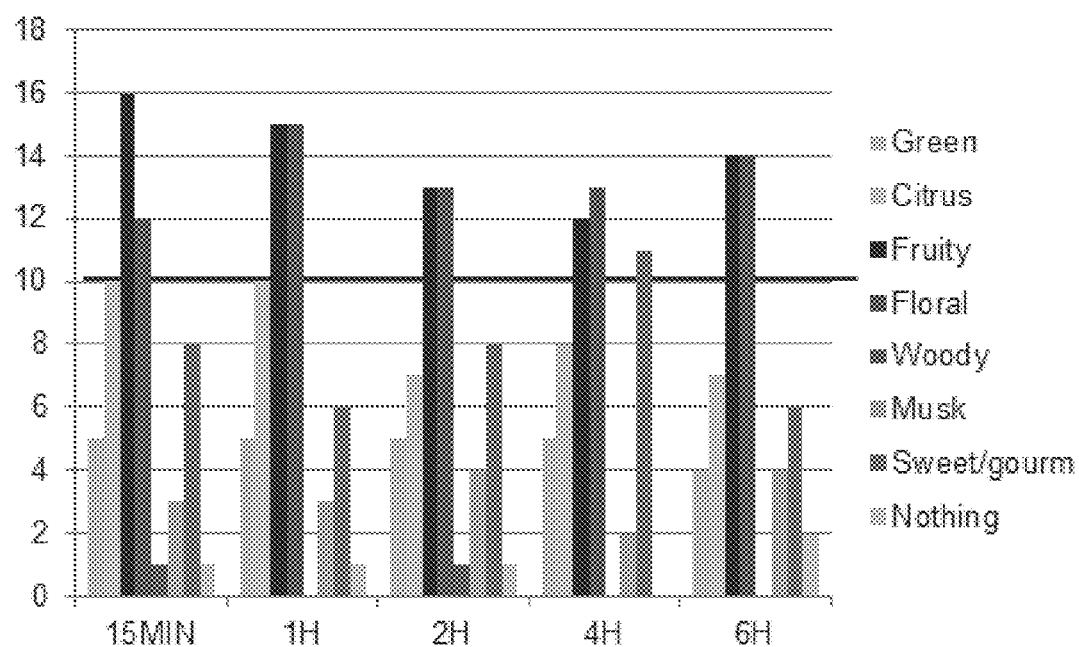
FIG. 10 shows the olfactive profile of a fine fragrance according to one aspect presented herein at the times indicated, after a subject has been exposed to the fine fragrance for two minutes. The bars at each time point, moving from left to right, represent the number of subjects that perceived green, citrus, fruity, floral, woody, musk, or sweet/gourmand notes, or lack of any note.

Referring to FIG. 10, the perception of the attention modulation fine fragrance did not decline as much, compared to the decline observed with the reference fragrance following a two minute exposure to the fragrance. After exposure, 51% of the selected terms were above chance compared to only 15% for the reference fragrance.

Figure 11:
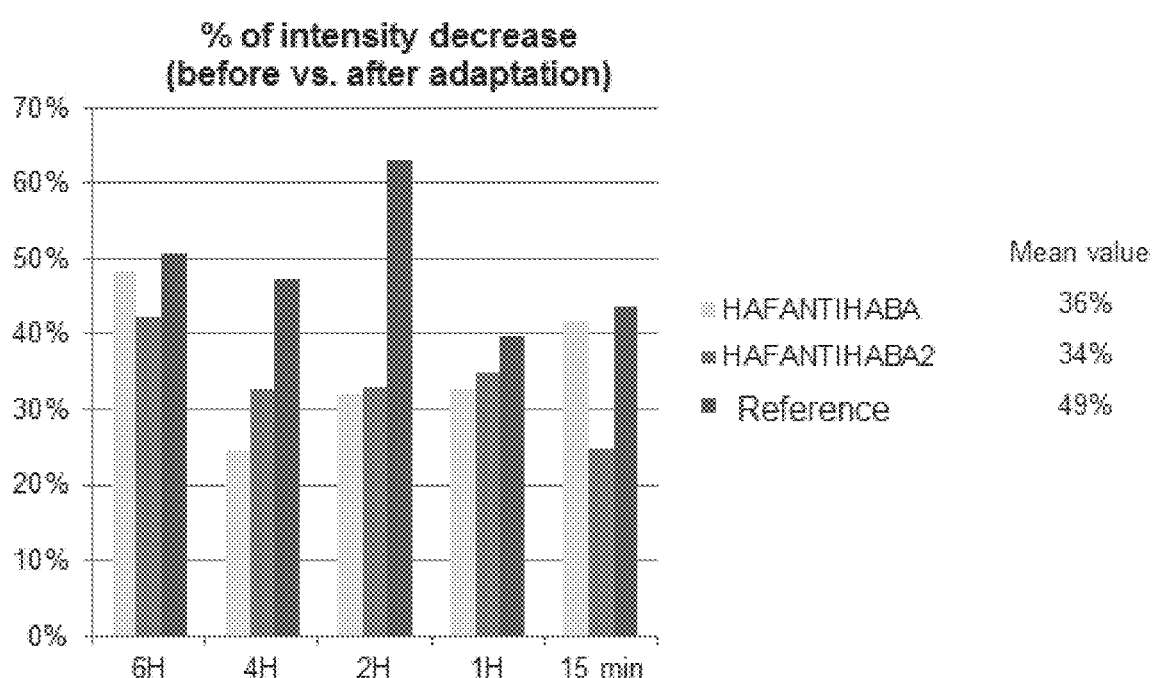
FIG. 11 shows the mean decrease in perceived intensity of the fine fragrances evaluated in Example 4.

FIG. 11 shows the effect of adaptation on the percent intensity decrease of perception following adaptation of the reference and two test fragrances. A greater decrease in intensity following adaptation was observed in the reference fragrance, particularly at 2 and 4 hours.

Taken together, these data suggest that the olfactive profiles of perfume compositions according to some aspects presented herein change more over time, compared to a reference composition. Additionally, less adaptation is observed by subjects for perfume compositions according to some aspects presented herein change more over time, compared to a reference composition. Finally, the perfume compositions according to some aspects presented herein are more long lasting than reference compositions, as evidenced by a lower decrease in perceived intensity after a 2 minute adaptation.

TABLE 4

| | Perfuming Compounds Having a Watery Note | | | | |
|---|---|---|---|---|---|
| Type | Name | Molecular Weight | Volatility (µg/l air) | Log P (n-octanol/ water) | Odor Threshold (µg/l air) | Odor Value |
| TOP | (+−)-2,6-DIMETHYL-5-HEPTENAL | 140 | 1889.68 | 3.15 | 2.11E−04 | 8.96E+06 |
| TOP | (2E,6Z)-2,6-NONADIENAL" | 138 | 632.43 | 2.56 | 1.46E−04 | 4.34E+06 |
| TOP | (2E,6Z)-2,6-NONADIENAL" | 138 | 632.43 | 2.56 | 1.46E−04 | 4.34E+06 |
| TOP | METHYL 2-OCTYNOATE" | 154 | 472.01 | 2.90 | 8.31E−04 | 5.68E+05 |
| TOP | DECANAL" | 156 | 466.56 | 3.99 | 1.92E−03 | 2.43E+05 |
| TOP | (+−)-2-methyldecanal" | 170 | 297.74 | 3.73 | 9.00E−04 | 3.31E+05 |
| TOP | undecanal | 170 | 178.29 | 4.56 | 1.65E−03 | 1.08E+05 |
| TOP | DODECANAL | 184 | 144.79 | 4.94 | 9.90E−04 | 1.46E+05 |
| TOP | 10-undecenal | 168 | 136.73 | 3.93 | 3.15E−03 | 4.34E+04 |
| TOP | 10-undecenal (A) + (9E)-9-undecenal (B) + (9Z)-9-undecenal (C) | 168 | 131.95 | 4.26 | 3.77E−05 | 3.50E+06 |
| TOP | 8-ISOPROPYL-6-METHYL-BICYCLO[2.2.2]OCT-5-ENE-2-CARBALDEHYDE | 192 | 131.02 | 3.81 | 7.11E−05 | 1.84E+06 |
| TOP | (2Z)-3,7-dimethyl-2,6-octadien-1-yl acetate | 196 | 123.21 | 3.81 | 6.02E−02 | 2.05E+03 |
| middle | (2E,6Z)-2,6-NONADIEN-1-OL | 140 | 98.76 | 2.68 | 3.22E−06 | 3.07E+07 |
| middle | METHYL 2-NONYNOATE | 168 | 91.76 | 3.51 | 1.60E−03 | 5.74E+04 |

TABLE 4-continued

Perfuming Compounds Having a Watery Note

| Type | Name | Molecular Weight | Volatility (μg/l air) | Log P (n-octanol/water) | Odor Threshold (μg/l air) | Odor Value |
|---|---|---|---|---|---|---|
| middle | 7-methyl-2H-1,5-benzodioxepin-3(4H)-one | 142 | 89.26 | 3.40 | 5.05E−04 | 1.77E+05 |
| middle | (+−)-TETRAHYDRO-2-ISOBUTYL-4-METHYL-4(2H)-PYRANOL | 172 | 79.79 | 2.22 | 1.35E−02 | 5.91E+03 |
| middle | (+−)-2-methylundecanal | 184 | 75.55 | 5.01 | 7.24E−05 | 1.04E+06 |
| middle | (2R)-2-methyl-4-[(1R)-2,2,3-trimethyl-3-cyclopenten-1-yl]-4-pentenal (A) + (2S)-2-methyl-4-[(1R)-2,2,3-trimethyl-3-cyclopenten-1-yl]-4-pentenal (B) | 206 | 63.49 | 4.25 | 2.22E−03 | 2.86E+04 |
| middle | 7-methyl-2H-1,5-benzodioxepin-3(4H)-one | 178 | 56.74 | 1.61 | 3.20E−06 | 1.77E+07 |
| middle | 7-ISOPROPYL-2H,4H-1,5-BENZODIOXEPIN-3-ONE | 178 | 56.74 | 1.61 | 3.20E−06 | 1.77E+07 |
| middle | DODECANENITRILE | 178 | 56.74 | 1.61 | 3.20E−06 | 1.77E+07 |
| bottom | 3-(4-ETHYLPHENYL)-2,2-DIMETHYLPROPANAL (A) + 3-(2-ETHYLPHENYL)-2,2-DIMETHYLPROPANAL (B) | 190 | 48.69 | 3.56 | 5.33E−03 | 9.14E+03 |
| bottom | 7-methyl-2H-1,5-benzodioxepin-3(4H)-one | 190 | 32.27 | 3.53 | 6.05E−05 | 5.33E+05 |
| bottom | (+−)-1-METHYL-4-(4-METHYL-3-PENTENYL)-3-CYCLOHEXENE-1-CARBALDEHYDE | 206 | 26.54 | 5.14 | 2.72E−02 | 9.76E+02 |
| bottom | (+−)-3-(4-isopropylphenyl)-2-methylpropanal | 190 | 24.85 | 3.59 | 3.00E−03 | 8.28E+03 |
| bottom | (+−)-3-(4-methyl-3-penten-1-yl)-3-cyclohexene-1-carbaldehyde (A) + (+−)-4-(4-methyl-3-penten-1-yl)-3-cyclohexene-1-carbaldehyde (B) | 192 | 21.54 | 4.11 | 3.68E−03 | 5.85E+03 |
| bottom | (+−)-3-(4-methoxyphenyl)-2-methylpropanal | 178 | 18.99 | 2.80 | 9.79E−03 | 1.94E+03 |
| bottom | (+−)-2,6,10-TRIMETHYL-9-UNDECENAL | 210 | 18.23 | 5.20 | 1.59E−02 | 1.15E+03 |
| bottom | 1,5,9-TRIMETHYL-4,8-DECADIENYL ACETATE | 238 | 14.74 | 5.28 | 3.28E−04 | 4.49E+04 |
| bottom | (+−)-3-(3-ISOPROPYL-1-PHENYL)BUTANAL | 194 | 14.74 | 2.01 | 7.71E−04 | 1.91E+04 |

TABLE 4-continued

| | Perfuming Compounds Having a Watery Note | | | | | |
|---|---|---|---|---|---|---|
| Type | Name | Molecular Weight | Volatility (µg/l air) | Log P (n-octanol/water) | Odor Threshold (µg/l air) | Odor Value |
| bottom | 3-(3,3-dimethyl-2,3-dihydro-1H-inden-5-yl)propanal (A) + 3-(1,1-dimethyl-2,3-dihydro-1H-inden-5-yl)propanal (B) | 206 | 13.73 | 2.58 | 1.32E−05 | 1.04E+06 |
| bottom | 3-(3,3-dimethyl-2,3-dihydro-1H-inden-5-yl)propanal (A) + 3-(1,1-dimethyl-2,3-dihydro-1H-inden-4-yl)propanal (B) + 3-(1,1-dimethyl-2,3-dihydro-1H-inden-5-yl)propanal (C) | 181 | 13.68 | 4.63 | 4.00E−03 | 3.42E+03 |
| bottom | (+−)-2-methyl-3-[4-(2-methyl-2-propanyl)phenyl]propanal | 204 | 12.86 | 3.90 | 2.39E−04 | 5.38E+04 |
| bottom | (+−)-7-hydroxy-3,7-dimethyloctanal | 172 | 12.81 | 2.00 | 6.98E−03 | 1.84E+03 |
| bottom | CYCLOSIA BASE (POLYMER) (MAIN CPD = 7-HYDROXY-3,7-DIMETHYLOCTANAL) | 172 | 10.34 | 2.00 | 6.98E−03 | 1.48E+03 |
| bottom | (Z)-6-NONEN-1-OL | 202 | 6.91 | 3.44 | 6.10E−04 | 1.13E+04 |
| bottom | (1S,4S,9S,10R,13R)-5,5,9,13-tetramethyl-14,16-dioxatetracyclo[11.2.1.0~1,10~.0~4,9~]hexadecane (A) + (1R,4S,9S,10R,13S)-5,5,9,13-tetramethyl-14,16-dioxatetracyclo[11.2.1.0~1,10~.0~4,9~]hexadecane (B) | 278 | 6.77 | 4.59 | 4.36E−04 | 1.55E+04 |
| bottom | 8(9)-METHOXY-TRICYCLO[5.2.1.0(2,6)]DECANE-3(4)-CARBALDEHYDE | 193 | 5.87 | 5.00 | 4.02E−05 | 1.46E+05 |
| bottom | (+−)-2,5-DIMETHYL-2-INDANMETHANOL | 176 | 4.86 | 3.12 | 1.28E−04 | 3.79E+04 |
| bottom | 7-PROPYL-2H,4H-1,5-BENZODIOXEPIN-3-ONE | 206 | 4.85 | 2.79 | 6.43E−05 | 7.54E+04 |
| bottom | 7-(2-methyl-2-propanyl)-2H-1,5-benzodioxepin-3(4H)-one | 220 | 4.37 | 2.97 | 1.53E−04 | 2.85E+04 |
| bottom | (+−)-3-(1,3-BENZODIOXOL-5-YL)-2-METHYLPROPANAL | 192 | 3.57 | 1.28 | 2.23E−04 | 1.60E+04 |

TABLE 4-continued

| | Perfuming Compounds Having a Watery Note | | | | | |
|---|---|---|---|---|---|---|
| Type | Name | Molecular Weight | Volatility (μg/l air) | Log P (n-octanol/water) | Odor Threshold (μg/l air) | Odor Value |
| bottom | METHYL 2,4-DIHYDROXY-3,6-DIMETHYLBENZOATE | 196 | 1.52 | 2.30 | 4.89E−06 | 3.11E+05 |
| bottom | (+−)-3-(4-hydroxy-4-methylpentyl)-3-cyclohexene-1-carbaldehyde (A) + (+−)-4-(4-hydroxy-4-methylpentyl)-3-cyclohexene-1-carbaldehyde (B) | 210 | 0.70 | 2.19 | 8.81E−05 | 7.92E+03 |

TABLE 5

| | Perfuming Compounds Having a Green Note | | | | | |
|---|---|---|---|---|---|---|
| Type | Name | Molecular Weight | Volatility (μg/l air) | Log P (n-octanol/water) | Odor Threshold (μg/l air) | Odor Value |
| Top | ETHYL BUTANOATE | 116 | 142519.74 | 2.03 | 3.68E−04 | 3.87E+08 |
| Top | (+−)-ethyl 2-methylbutanoate | 130 | 83769.16 | 2.58 | 1.26E−04 | 6.67E+08 |
| Top | hexanal | 100 | 68294.85 | 2.00 | 1.76E−03 | 3.88E+07 |
| Top | 3-METHYLBUTYL ACETATE (A) + (+−)-2-METHYLBUTYL ACETATE (B) | 130 | 51307.81 | 2.65 | 5.92E−02 | 8.67E+05 |
| Top | (+−)-ETHYL 2-METHYLPENTANOATE | 144 | 35090.18 | 3.05 | 3.84E−05 | 9.14E+08 |
| Top | (−)-(1S)-2,6,6-TRIMETHYL-BICYCLO[3.1.1]HEPT-2-ENE | 136 | 33722.60 | 5.43 | 1.02E−01 | 3.31E+05 |
| Top | beta-PINENE 89% (A) + alpha-PINENE 11% (B) | 136 | 33722.60 | 5.43 | 1.02E−01 | 3.31E+05 |
| Top | (2E)-2-HEXENAL | 98 | 33708.26 | 1.62 | 2.53E−03 | 1.33E+07 |
| Top | (+−)-3-HYDROXY-2-BUTANONE | 88 | 33382.87 | −1.03 | 1.46E−02 | 2.28E+06 |
| Top | 3-methyl-2-buten-1-yl acetate | 128 | 27705.98 | 2.19 | 5.58E−02 | 4.97E+05 |
| Top | METHYL HEXANOATE | 130 | 23345.90 | 2.65 | 8.43E−02 | 2.77E+05 |
| Top | (+−)-2-ethenyl-2,6,6-trimethyltetrahydro-2H-pyran | 154 | 23116.66 | 3.59 | 1.64E−01 | 1.41E+05 |
| Top | HEPTANAL | 114 | 22184.00 | 2.15 | 2.03E−03 | 1.09E+07 |
| Top | 1-BUTANOL | 74 | 17700.00 | 0.88 | 8.70E−02 | 2.03E+05 |
| Top | 1,1-DIETHOXY-3,7-DIMETHYL-2,6-OCTADIENE | 226 | 16590.69 | 4.59 | 3.57E−03 | 4.65E+06 |
| Top | (+−)-3,5,5-TRIMETHYLHEXANAL | 142 | 12045.92 | 3.02 | 9.37E−03 | 1.29E+06 |
| Top | (Z)-3-HEXENYL FORMATE | 128 | 9873.53 | 2.17 | 2.11E−03 | 4.68E+06 |
| Top | ETHYL HEXANOATE | 145 | 9675.10 | 3.12 | 9.11E−04 | 1.06E+07 |

TABLE 5-continued

Perfuming Compounds Having a Green Note

| Type | Name | Molecular Weight | Volatility (µg/l air) | Log P (n-octanol/water) | Odor Threshold (µg/l air) | Odor Value |
|---|---|---|---|---|---|---|
| Top | BENZALDEHYDE | 106 | 8207.00 | 1.33 | 4.26E−02 | 1.93E+05 |
| Top | (1R,5R)-4,7,7-trimethyl-6-thiabicyclo[3.2.1]oct-3-ene (A) + (1R,4R,5R)-4,7,7-trimethyl-6-thiabicyclo[3.2.1]octane (B) | 168 | 6351.47 | 4.48 | 7.99E−05 | 7.95E+07 |
| Top | (E)-2-HEXENYL ACETATE | 142 | 6062.68 | 2.59 | 2.08E−01 | 2.92E+04 |
| Top | (Z)-3-HEXEN-1-OL | 100 | 5986.62 | 1.65 | 1.13E−02 | 5.30E+05 |
| Top | 6-METHYL-5-HEPTEN-2-ONE | 126 | 5775.94 | 2.05 | 1.06E−01 | 5.45E+04 |
| Top | 1-ISOBUTYL-3-METHYLBUTYL ACETATE | 186 | 5265.61 | 4.19 | 1.62E+00 | 3.24E+03 |
| Top | OCTANAL | 128 | 4147.61 | 2.94 | 2.77E−04 | 1.50E+07 |
| Top | (2Z)-3-methyl-2-hexen-1-yl acetate (A) + (2E)-3-methyl-2-hexen-1-yl acetate (B) | 156 | 4131.05 | 3.11 | 2.73E−02 | 1.51E+05 |
| Top | (1RS,6RS)-3,6-dimethyl-3-cyclohexene-1-carbaldehyde (A) + (1RS,6RS)-4,6-dimethyl-3-cyclohexene-1-carbaldehyde (B) + (1RS,6SR)-4,6-dimethyl-3-cyclohexene-1-carbaldehyde (C) | 138 | 3770.43 | 2.24 | 2.69E−04 | 1.40E+07 |
| Top | (E)-2-HEXEN-1-OL | 100 | 3752.17 | 1.73 | 1.29E−01 | 2.92E+04 |
| Top | 3,7-DIMETHYL-1,3,6-OCTATRIENE | 136 | 3480.57 | 4.91 | 2.57E−02 | 1.35E+05 |
| Top | (Z)-3-HEXENYL ACETATE | 142 | 3398.34 | 2.62 | 1.00E−02 | 3.40E+05 |
| Top | (+−)-1-octen-3-ol | 128 | 3030.11 | 2.33 | 1.77E−03 | 1.71E+06 |
| Top | ETHYL 3-OXOBUTANOATE (A) <=> (2Z)-ETHYL 3-HYDROXY-2-BUTENOATE (B) | 130 | 2885.67 | 0.35 | 5.83E−02 | 4.95E+04 |
| Top | nonanal | 142 | 2777.63 | 3.42 | 8.14E−03 | 3.41E+05 |
| Top | DIBUTYL SULFIDE | 146 | 2766.10 | 4.86 | 2.34E−02 | 1.18E+05 |
| Top | (3Z)-1-[(2E)-2-buten-1-yloxy]-3-hexene (A) + (3Z)-1-[(2Z)-2-buten-1-yloxy]-3-hexene (B) | 154 | 2673.47 | 3.77 | 2.05E−02 | 1.31E+05 |
| Top | (+−)-1-METHOXY-3-HEXANETHIOL | 148 | 2534.77 | 3.06 | 1.92E−07 | 1.32E+10 |
| Top | TETRAHYDRO-4-METHYL-2-(2-METHYL-1-PROPENYL)-2H-PYRAN | 154 | 2483.93 | 3.49 | 8.77E−04 | 2.83E+06 |

TABLE 5-continued

Perfuming Compounds Having a Green Note

| Type | Name | Molecular Weight | Volatility (µg/l air) | Log P (n-octanol/water) | Odor Threshold (µg/l air) | Odor Value |
|---|---|---|---|---|---|---|
| Top | (+−)-TETRAHYDRO-4-METHYL-2-(2-METHYL-1-PROPENYL)-2H-PYRAN (A) + 3,6-DIHYDRO-4-METHYL-2-(2-METH-.(B) | 154 | 2483.93 | 3.49 | 8.77E−04 | 2.83E+06 |
| Top | (Z)-6-NONENAL | 140 | 2431.73 | 2.88 | 2.91E−05 | 8.36E+07 |
| Top | HEXYL ACETATE | 144 | 2316.04 | 3.09 | 1.32E−01 | 1.75E+04 |
| Top | (+−)-ETHYL 3-METHYL-2-OXOPENTANOATE | 158 | 2276.17 | 1.96 | 5.06E−04 | 4.50E+06 |
| Top | 1-hexanol | 102 | 2070.00 | 2.20 | 1.17E−01 | 1.77E+04 |
| Top | (+−)-METHYL 2,6,6-TRIMETHYL-2-CYCLOHEXENE-1-CARBOXYLATE | 182 | 2010.91 | 3.16 | 1.06E−02 | 1.90E+05 |
| Top | 3,5,6-TRIMETHYL-3-CYCLOHEXENE-1-CARBALDEHYDE (A) + 2,4,6-TRIMETHYL-3-CYCLOHEXENE-1-CARBALDEHYDE (B) | 152 | 1951.74 | 3.23 | 6.17E−03 | 3.16E+05 |
| Top | (2-ISOPROPOXYETHYL)BENZENE | 164 | 1714.82 | 3.15 | 1.65E−03 | 1.04E+06 |
| Top | (3Z)-3-hexen-1-yl butyrate | 170 | 1674.15 | 3.59 | 7.85E−02 | 2.13E+04 |
| Top | hexyl 2-methylpropanoate | 172 | 1661.18 | 4.31 | 7.15E−01 | 2.32E+03 |
| Top | PYRAZOBUTYLE | 166 | 1617.21 | 2.88 | 7.20E−07 | 2.25E+09 |
| Top | (3Z)-hex-3-en-1-yl methyl carbonate | 158 | 1506.33 | 2.97 | 4.58E−02 | 3.29E+04 |
| Top | BENZYL FORMATE | 136 | 1339.53 | 1.76 | 3.23E−01 | 4.15E+03 |
| Top | (3E,5Z)-1,3,5-UNDECATRIENE | 150 | 1247.28 | 5.68 | 3.76E−05 | 3.32E+07 |
| Top | (2-METHOXYETHYL)BENZENE | 136 | 1239.07 | 2.33 | 6.32E−04 | 1.96E+06 |
| Top | ALLYL HEPTANOATE | 170 | 1235.24 | 4.16 | 1.75E−02 | 7.06E+04 |
| Top | (+−)-1-(3,3-dimethylcyclohexyl)ethanone (A) + (+−)-2,6,6-trimethylcycloheptanone (B) | 154 | 1214.93 | 2.99 | 1.44E−02 | 8.44E+04 |
| Top | (2RS,4SR)-2-methyl-4-propyl-1,3-oxathiane (A) + (2RS,4RS)-2-methyl-4-propyl-1,3-oxathiane (B) | 160 | 1113.06 | 3.11 | 1.47E−03 | 7.57E+05 |
| Top | (Z)-3-HEXENYL ISOBUTYRATE | 170 | 1073.97 | 3.57 | 4.54E−02 | 2.36E+04 |
| Top | (+)-(R)-4-(2-methoxypropan-2-yl)-1-methylcyclohex-1-ene | 168 | 993.39 | 4.59 | 1.99E−01 | 5.00E+03 |

TABLE 5-continued

Perfuming Compounds Having a Green Note

| Type | Name | Molecular Weight | Volatility (µg/l air) | Log P (n-octanol/water) | Odor Threshold (µg/l air) | Odor Value |
|---|---|---|---|---|---|---|
| Top | (3Z)-1,3-undecadien-5-yne (A) + (3E)-1,3-undecadien-5-yne (B) | 148 | 990.87 | 5.11 | 3.32E−03 | 2.98E+05 |
| Top | (+−)-(Z)-3-HEXENYL 2-METHYLBUTANOATE | 184 | 833.05 | 3.84 | 1.96E−02 | 4.24E+04 |
| Top | ethyl octanoate | 172 | 800.05 | 4.20 | 5.30E−03 | 1.51E+05 |
| Top | 2-METHYL-3-HEXANONE OXIME | 129 | 687.75 | 2.08 | 4.81E−04 | 1.43E+06 |
| Top | (2E,6Z)-2,6-NONADIENAL | 138 | 632.43 | 2.56 | 1.46E−04 | 4.34E+06 |
| Top | (Z)-4-DECENAL | 154 | 629.54 | 1.11 | 3.78E−05 | 1.67E+07 |
| Top | (+−)-(3-methoxy-2-methylpropyl)benzene | 164 | 587.76 | 3.57 | 1.51E−02 | 3.89E+04 |
| Top | 2-PHENYLETHYL FORMATE | 150 | 567.67 | 1.90 | 8.34E−04 | 6.81E+05 |
| Top | ETHYL 2-METHYL-1,3-DIOXOLANE-2-ACETATE | 174 | 479.20 | 1.12 | 1.62E−03 | 2.95E+05 |
| Top | METHYL 2-OCTYNOATE | 154 | 472.01 | 2.90 | 8.31E−04 | 5.68E+05 |
| Top | (2,2-DIMETHOXYETHYL)BENZENE | 166 | 456.97 | 2.10 | 4.55E−02 | 1.00E+04 |
| Top | 2-METHYLPENTYL 2-METHYLPENTANOATE | 200 | 450.33 | 5.13 | 2.41E−01 | 1.87E+03 |
| Top | (+−)-3,7-DIMETHYL-3-OCTANOL | 158 | 421.15 | 3.78 | 3.45E−03 | 1.22E+05 |
| Top | (+−)-3-mercaptohexyl acetate | 176 | 421.09 | 2.64 | 2.72E−06 | 1.55E+08 |
| Top | 3-(4,4-dimethyl-1-cyclohexen-1-yl)propanal | 166 | 417.92 | 3.30 | 2.06E−03 | 2.03E+05 |
| Top | (1RS,2RS)-2-(2-methyl-2-propanyl)cyclohexyl acetate (A) + (1RS,2SR)-2-(2-methyl-2-propanyl)cyclohexyl acetate (B) | 198 | 402.03 | 4.40 | 2.12E−02 | 1.90E+04 |
| Top | 1,1-DIMETHOXY-2-PHENYLPROPANE | 180 | 376.94 | 2.50 | 1.42E−02 | 2.65E+04 |
| Top | (+−)-1,5-DIMETHYL-1-VINYL-4-HEXENYL ACETATE | 196 | 339.21 | 4.04 | 7.40E−02 | 4.58E+03 |
| Top | (+−)-1,5-DIMETHYL-1-VINYL-4-HEXENYL ACETATE (A) + 1-P-MENTHEN-8-YL ACETATE (B) | 196 | 339.21 | 4.04 | 7.40E−02 | 4.58E+03 |
| Top | (+−)-PERHYDRO-4alpha,8Abeta-DIMETHYL-4A-NAPHTHALENOL | 182 | 330.48 | 3.92 | 5.32E−06 | 6.21E+07 |

TABLE 5-continued

| | | | | Log P (n-octanol/ water) | Odor Threshold (µg/l air) | Odor Value |
|---|---|---|---|---|---|---|
| Type | Name | Molecular Weight | Volatility (µg/l air) | | | |
| Top | (+−)-3,7-dimethyl-6-octen-1-yl formate (A) + (2E)-3,7-dimethyl-2,6-octadien-1-yl formate (B) | 184 | 322.28 | 3.79 | 5.28E−04 | 6.10E+05 |
| Top | (+−)-ethyl 2-acetyl-4-methyl-4-pentenoate | 184 | 295.22 | 2.15 | 3.64E−03 | 8.10E+04 |
| Top | (+−)-(4Z)-4-cycloocten-1-yl methyl carbonate | 184 | 278.83 | 3.02 | 3.69E−04 | 7.56E+05 |
| Top | methyl (2E)-2-nonenoate | 170 | 264.84 | 4.05 | 5.84E−02 | 4.53E+03 |
| Top | (+−)-2,4-dimethyl-4-phenyltetrahydrofuran | 176 | 263.73 | 3.02 | 5.04E−04 | 5.23E+05 |
| Top | (+−)-3,7-DIMETHYL-6-OCTENYL FORMATE | 184 | 262.84 | 4.16 | 1.72E−03 | 1.53E+05 |
| Top | ALLYL (3-METHYLBUTOXY)ACETATE (A) + (+−)-ALLYL (2-METHYLBUTOXY)ACETATE (B) | 186 | 261.90 | 2.79 | 9.89E−05 | 2.65E+06 |
| Top | hexyl (2E)-2-methyl-2-butenoate | 184 | 256.81 | 4.80 | 1.16E−02 | 2.22E+04 |
| Top | (2RS,5SR)-6-ethyl-2,10,10-trimethyl-1-oxaspiro[4.5]deca-3,6-diene (A) + (2RS,5RS)-6-ethyl-2,10,10-trimethyl-1-oxaspiro[4.5]deca-3,6-diene (B) | 206 | 252.44 | 5.07 | 7.71E−03 | 3.27E+04 |
| Top | (+−)-3-PHENYLBUTANAL | 148 | 227.83 | 2.34 | 3.89E−04 | 5.86E+05 |
| Top | (3Z)-3-hexen-1-yl (3Z)-3-hexenoate | 196 | 210.68 | 4.22 | 5.17E−02 | 4.08E+03 |
| Top | (Z)-3,7-DIMETHYL-2,6-OCTADIENAL (A) + (E)-3,7-DIMETHYL-2,6-OCTADIENAL (B) | 152 | 202.66 | 2.68 | 4.12E−03 | 4.92E+04 |
| Top | HEXANOIC ACID | 116 | 197.90 | 1.92 | 1.82E−02 | 1.09E+04 |
| Top | 2-METHOXY-3-(4-METHYLPENTYL)PYRAZINE | 194 | 195.24 | 4.27 | 1.18E−07 | 1.65E+09 |
| Top | 2-METHOXY-4-PROPYL-1-CYCLOHEXANOL | 172 | 189.74 | 2.60 | 2.85E−02 | 6.66E+03 |

TABLE 5-continued

Perfuming Compounds Having a Green Note

| Type | Name | Molecular Weight | Volatility (µg/l air) | Log P (n-octanol/water) | Odor Threshold (µg/l air) | Odor Value |
|---|---|---|---|---|---|---|
| Top | (+−)-CIS-TETRAHYDRO-METHYL-4-METHYLENE-6-PHENYL-2H-PYRAN (A) + (+−)-CIS-3,6-DIHYDRO-4,6-DIMETHYL-2-PHENYL-2H-PYRAN (B) + (+−)-CIS-3,6-DIHYDRO-2,4-DIMETHYL-6-PHENYL-2H-PYRAN (C) | 188 | 189.16 | 3.95 | 1.73E−05 | 1.09E+07 |
| Top | 4-PHENYL-2-BUTANONE | 148 | 176.55 | 1.79 | 2.22E−04 | 7.95E+05 |
| Top | (3Z)-3-hexen-1-yl (2E)-2-methyl-2-butenoate | 182 | 168.78 | 3.96 | 9.92E−03 | 1.70E+04 |
| Top | 10-undecenal (A) + 9-undecenal (B) | 168 | 167.56 | 4.20 | 3.56E−04 | 4.71E+05 |
| Top | (1R,4R)-8-MERCAPTO-3-P-MENTHANONE | 186 | 155.12 | 2.99 | 3.43E−05 | 4.52E+06 |
| Top | (+−)-2-phenyl-1-propanol | 136 | 142.19 | 1.74 | 3.62E−02 | 3.93E+03 |
| Top | (+)-(3S)-3-[(1R)-4-methyl-3-cyclohexen-1-yl]butanal (A) + (+)-(3R)-3-[(1R)-4-methyl-3-cyclohexen-1-yl]butanal | 166 | 134.08 | 3.51 | 1.11E−03 | 1.21E+05 |
| Top | 8-ISOPROPYL-6-METHYL-BICYCLO[2.2.2]OCT-5-ENE-2-CARBALDEHYDE | 192 | 131.02 | 3.81 | 7.11E−05 | 1.84E+06 |
| Top | 5-METHYL-3-HEPTANONE OXIME | 143 | 128.04 | 2.45 | 8.80E−03 | 1.45E+04 |
| Top | BENZYL PROPANOATE | 164 | 113.60 | 2.35 | 2.81E−02 | 4.04E+03 |
| Top | ETHYL TRICYCLO[5.2.1.0.(2,6)]DECANE-2-CARBOXYLATE | 208 | 111.67 | 4.32 | 6.87E−05 | 1.63E+06 |
| Top | (+−)-(2E)-1-(2,6,6-trimethyl-2-cyclohexen-1-yl)-2-buten-1-one | 192 | 110.53 | 3.65 | 1.04E−04 | 1.06E+06 |
| Middle | (1RS,2RS,7SR,8SR)-tricyclo[6.2.1.0~2,7~]undec-9-en-3-one (A) + (1RS,2SR,7RS,8SR)-tricyclo[6.2.1.0~2,7~]undec-9-en-3-one (B) | 162 | 99.95 | 2.53 | 1.23E−02 | 8.13E+03 |
| Middle | (2E,6Z)-2,6-NONADIEN-1-OL | 140 | 98.76 | 2.68 | 3.22E−06 | 3.07E+07 |
| Middle | 4-METHOXYBENZALDEHYDE | 135 | 98.47 | 1.56 | 1.81E−05 | 5.44E+06 |
| Middle | 4-METHOXYBENZALDEHYDE | 136 | 98.47 | 1.56 | 1.81E−05 | 5.44E+06 |
| Middle | METHYL 2-NONYNOATE | 168 | 91.76 | 3.51 | 1.60E−03 | 5.74E+04 |

TABLE 5-continued

Perfuming Compounds Having a Green Note

| Type | Name | Molecular Weight | Volatility (μg/l air) | Log P (n-octanol/water) | Odor Threshold (μg/l air) | Odor Value |
|---|---|---|---|---|---|---|
| Middle | (4-METHYLPHENOXY)ACETALDEHYDE | 150 | 89.41 | 1.99 | 6.46E−05 | 1.38E+06 |
| Middle | 7-methyl-2H-1,5-benzodioxepin-3(4H)-one | 142 | 89.26 | 3.40 | 5.05E−04 | 1.77E+05 |
| Middle | (E)-3,7-DIMETHYL-2,6-OCTADIENYL ACETATE (A) + 3,7-DIMETHYL-6-OCTENYL ACETATE (B) | 196 | 85.23 | 3.99 | 3.57E−02 | 2.39E+03 |
| Middle | GERANYL ACETATE (A) + NERYL ACETATE (B) | 196 | 85.23 | 3.99 | 3.57E−02 | 2.39E+03 |
| Middle | (E)-3,7-DIMETHYL-2,6-OCTADIENYL ACETATE | 196 | 79.23 | 3.99 | 3.57E−02 | 2.22E+03 |
| Middle | 3,7-DIMETHYL-2,6-NONADIENENITRILE (A) + 3,7-DIMETHYL-3,6-NONADIENENITRILE (B) | 163 | 78.89 | 3.17 | 3.10E−04 | 2.55E+05 |
| Middle | ALLYL 3-CYCLOHEXYLPROPANOATE | 196 | 75.80 | 4.51 | 7.96E−03 | 9.53E+03 |
| Middle | (+−)-4-methylene-2-phenyltetrahydro-2H-pyran (A) + (+−)-4-methyl-6-phenyl-3,6-dihydro-2H-pyran (B) + (+−)-4-methyl-2-phenyl-3,6-dihydro-2H-pyran (C) | 174 | 70.50 | 3.33 | 6.64E−06 | 1.06E+07 |
| Middle | (+−)-(3E)-4-(2,6,6-trimethyl-2-cyclohexen-1-yl)-3-buten-2-one | 192 | 68.11 | 4.06 | 5.30E−04 | 1.29E+05 |
| Middle | (+−)-(E)-4-METHYL-3-DECEN-5-OL | 170 | 64.15 | 3.63 | 6.78E−04 | 9.46E+04 |
| Middle | 6(8)-ISOPROPYLQUINOLINE | 171 | 60.10 | 3.44 | 1.24E−04 | 4.84E+05 |
| Middle | 1-PHENYL-2-(1-PROPOXYETHOXY)ETHANE | 208 | 59.63 | 3.58 | 1.52E−03 | 3.93E+04 |
| Middle | (+−)-1,3-DIMETHYL-3-PHENYLBUTYL ACETATE | 220 | 50.65 | 3.02 | 1.06E−02 | 4.77E+03 |
| Middle | 1-(4-METHOXYPHENYL)-1-ETHANONE" | 150 | 50.21 | 1.76 | 1.41E−04 | 3.57E+05 |
| Bottom | (+−)-(1S,4aR,8S,8aR)-2,2,6,8-tetramethyl-1,2,3,4,4a,5,8,8a-octahydro-1-naphthalenol | 208 | 48.90 | 5.24 | 8.15E−04 | 6.00E+04 |

TABLE 5-continued

Perfuming Compounds Having a Green Note

| Type | Name | Molecular Weight | Volatility (μg/l air) | Log P (n-octanol/water) | Odor Threshold (μg/l air) | Odor Value |
|---|---|---|---|---|---|---|
| Bottom | 1-(3,3-dimethyl-1-cyclohexen-1-yl)-4-penten-1-one (A) + 1-(5,5-dimethyl-1-cyclohexen-1-yl)-4-penten-1-one (B) | 192 | 47.01 | 3.89 | 1.64E−06 | 2.87E+07 |
| Bottom | ALLYL (CYCLOHEXYLOXY)ACETATE | 198 | 47.01 | 2.62 | 4.66E−05 | 1.01E+06 |
| Bottom | 1-(5,5-dimethyl-1-cyclohexen-1-yl)-4-penten-1-one | 192 | 38.43 | 3.89 | 1.64E−06 | 2.34E+07 |
| Bottom | ethyl (2E,4Z)-2,4-decadienoate | 196 | 36.76 | 4.69 | 3.07E−04 | 1.20E+05 |
| Bottom | (+−)-3,4'-dimethylspiro[oxirane-2,9'-tricyclo[6.2.1.0~2,7~]undec[4]ene | 204 | 36.76 | 4.58 | 9.93E−04 | 3.70E+04 |
| Bottom | (−)-(S)-1,8-P-MENTHADIEN-7-OL | 152 | 33.78 | 2.68 | 2.07E−02 | 1.63E+03 |
| Bottom | 7-methyl-2H-1,5-benzodioxepin-3(4H)-one | 190 | 32.27 | 3.53 | 6.05E−05 | 5.33E+05 |
| Bottom | 1-DECANOL | 158 | 31.90 | 4.10 | 1.13E−02 | 2.83E+03 |
| Bottom | 2-BENZYL-4,4,6-TRIMETHYL-1,3-DIOXANE | 220 | 29.99 | 3.39 | 5.26E−02 | 5.70E+02 |
| Bottom | ETHYL (2E)-2,4,7-DECATRIENOATE | 194 | 25.34 | 4.25 | 1.49E−02 | 1.70E+03 |
| Bottom | (2S,5R)-5-methyl-2-(2-propanyl)cyclohexanone oxime | 169 | 22.29 | 2.81 | 5.52E−05 | 4.04E+05 |
| Bottom | (+−)-3-(4-methoxyphenyl)-2-methylpropanal | 178 | 18.99 | 2.80 | 9.79E−03 | 1.94E+03 |
| Bottom | (+−)-3-(3-ISOPROPYL-1-PHENYL)BUTANAL | 194 | 14.74 | 2.01 | 7.71E−04 | 1.91E+04 |
| Bottom | (1RS,2SR,8RS)-2-(8-ISOPROPYL-6-METHYL-BICYCLO[2.2.2]OCT-5-EN-2-YL)-1,3-DIOXOLANE | 236 | 11.75 | 5.51 | 1.51E−01 | 7.78E+01 |
| Bottom | (3Z)-3-hexen-1-yl benzoate | 204 | 11.05 | 4.21 | 4.37E−02 | 2.53E+02 |
| Bottom | 2-phenoxyethyl 2-methylpropanoate | 208 | 10.05 | 2.82 | 3.01E−02 | 3.34E+02 |
| Bottom | ALLYL PHENOXYACETATE | 192 | 9.94 | 2.04 | 1.22E−03 | 8.13E+03 |
| Bottom | (+−)-8-sec-butylquinoline (A) + (+−)-6-sec-butylquinoline (B) | 185 | 8.73 | 4.06 | 1.93E−04 | 4.53E+04 |
| Bottom | diethyl cis-1,4-cyclohexanedicarboxylate (A) + diethyl trans-1,4-cyclohexanedicarboxylate (B) | 228 | 8.51 | 2.65 | 2.87E−03 | 2.97E+03 |
| Bottom | (Z)-6-NONEN-1-OL | 202 | 6.91 | 3.44 | 6.10E−04 | 1.13E+04 |

TABLE 5-continued

Perfuming Compounds Having a Green Note

| Type | Name | Molecular Weight | Volatility (µg/l air) | Log P (n-octanol/water) | Odor Threshold (µg/l air) | Odor Value |
|---|---|---|---|---|---|---|
| Bottom | 7-PROPYL-2H,4H-1,5-BENZODIOXEPIN-3-ONE | 206 | 4.85 | 2.79 | 6.43E−05 | 7.54E+04 |
| Bottom | 7-(2-methyl-2-propanyl)-2H-1,5-benzodioxepin-3(4H)-one | 220 | 4.37 | 2.97 | 1.53E−04 | 2.85E+04 |
| Bottom | (3Z)-3-hexen-1-yl salicylate | 220 | 4.34 | 4.83 | 3.23E−04 | 1.34E+04 |
| Bottom | 2-(3-PHENYLPROPYL)PYRIDINE | 197 | 3.83 | 2.87 | 1.29E−06 | 2.98E+06 |
| Bottom | HEXYL 2-HYDROXYBENZOATE | 222 | 3.82 | 5.55 | 5.50E−03 | 6.95E+02 |
| Bottom | (+−)-(1E)-1-(2,6,6-trimethyl-2-cyclohexen-1-yl)-1,6-heptadien-3-one (A) + (1E)-1-(2,6,6-trimethyl-1-cyclohexen-1-yl)-1,6-heptadien-3-one (B) | 232 | 3.01 | 4.86 | 7.14E−03 | 4.22E+02 |
| Bottom | (2E)-2-benzylideneoctanal | 216 | 1.15 | 4.86 | 1.91E−03 | 6.01E+02 |
| Bottom | CYCLOHEXYLIDENE(PHENYL)ACETONITRILE | 197 | 0.96 | 3.24 | 3.31E−04 | 2.88E+03 |

TABLE 6

Perfuming Compounds Having a Fruity Note

| Type | Name | Molecular Weight | Volatility (µg/l air) | Log P (n-octanol/water) | Odor Threshold (µg/l air) | Odor Value |
|---|---|---|---|---|---|---|
| TOP | ETHYL ACETATE | 88 | 404705.61 | 0.80 | 7.26E−01 | 5.58E+05 |
| TOP | ETHYL BUTANOATE | 116 | 142519.74 | 2.03 | 3.68E−04 | 3.87E+08 |
| TOP | ETHYL ISOBUTYRATE | 116 | 132964.09 | 2.03 | 1.14E−04 | 1.17E+09 |
| TOP | BUTYL ACETATE | 116 | 117207.52 | 2.11 | 4.18E−01 | 2.80E+05 |
| TOP | (+−)-ethyl 2-methylbutanoate | 130 | 83769.16 | 2.58 | 1.26E−04 | 6.67E+08 |
| TOP | (+−)-ISOPROPYL 2-METHYLBUTANOATE | 144 | 51367.63 | 2.85 | 8.42E−03 | 6.10E+06 |
| TOP | 3-METHYLBUTYL ACETATE (A) + (+−)-2-METHYLBUTYL ACETATE (B) | 130 | 51307.81 | 2.65 | 5.92E−02 | 8.67E+05 |
| TOP | (+−)-ETHYL 2-METHYLPENTANOATE | 144 | 35090.18 | 3.05 | 3.84E−05 | 9.14E+08 |
| TOP | (2E)-2-HEXENAL | 98 | 33708.26 | 1.62 | 2.53E−03 | 1.33E+07 |
| TOP | 3-methyl-2-buten-1-yl acetate | 128 | 27705.98 | 2.19 | 5.58E−02 | 4.97E+05 |
| TOP | 2-HEPTANONE | 114 | 26409.73 | 2.09 | 5.85E−02 | 4.52E+05 |
| TOP | METHYL HEXANOATE | 130 | 23345.90 | 2.65 | 8.43E−02 | 2.77E+05 |
| TOP | 7-METHYL-3-METHYLENE-1,6-OCTADIENE | 136 | 15094.56 | 5.33 | 4.12E−02 | 3.66E+05 |

TABLE 6-continued

Perfuming Compounds Having a Fruity Note

| Type | Name | Molecular Weight | Volatility (μg/l air) | Log P (n-octanol/water) | Odor Threshold (μg/l air) | Odor Value |
|---|---|---|---|---|---|---|
| TOP | 5-METHYL-3-HEPTANONE | 128 | 14141.42 | 2.43 | 9.87E−02 | 1.43E+05 |
| TOP | (+)-LIMONENE | 136 | 10216.93 | 5.40 | 1.29E−01 | 7.92E+04 |
| TOP | (+−)-4-methyl-4-penten-2-yl 2-methylpropanoate | 170 | 9902.98 | 3.57 | 2.26E−01 | 4.39E+04 |
| TOP | (Z)-3-HEXENYL FORMATE | 128 | 9873.53 | 2.17 | 2.11E−03 | 4.68E+06 |
| TOP | ETHYL HEXANOATE | 144 | 9675.10 | 3.12 | 9.11E−04 | 1.06E+07 |
| TOP | ETHYL HEXANOATE | 145 | 9675.10 | 3.12 | 9.11E−04 | 1.06E+07 |
| TOP | 3-OCTANONE | 128 | 6787.60 | 2.56 | 4.53E−02 | 1.50E+05 |
| TOP | (+−)-methyl 2-ethylhexanoate | 158 | 6677.64 | 3.37 | 1.74E−01 | 3.84E+04 |
| TOP | 2-OCTANONE | 128 | 6639.71 | 2.60 | 5.37E−02 | 1.24E+05 |
| TOP | (1R,5R)-4,7,7-trimethyl-6-thiabicyclo[3.2.1]oct-3-ene (A) + (1R,4R,5R)-4,7,7-trimethyl-6-thiabicyclo[3.2.1]octane (B) | 168 | 6351.47 | 4.48 | 7.99E−05 | 7.95E+07 |
| TOP | (1R,5R)-4,7,7-trimethyl-6-thiabicyclo[3.2.1]oct-3-ene (A) + (1R,4R,5R)-4,7,7-trimethyl-6-thiabicyclo[3.2.1]octane (B) | 167 | 6351.47 | 4.48 | 7.99E−05 | 7.95E+07 |
| TOP | (1R,5R)-4,7,7-trimethyl-6-thiabicyclo[3.2.1]oct-3-ene (A) + (1R,4R,5R)-4,7,7-trimethyl-6-thiabicyclo[3.2.1]octane (B) | 168 | 6351.47 | 4.48 | 7.99E−05 | 7.95E+07 |
| TOP | (E)-2-HEXENYL ACETATE | 142 | 6062.68 | 2.59 | 2.08E−01 | 2.92E+04 |
| TOP | 6-METHYL-5-HEPTEN-2-ONE | 126 | 5775.94 | 2.05 | 1.06E−01 | 5.45E+04 |
| TOP | 1-ISOBUTYL-3-METHYLBUTYL ACETATE | 186 | 5265.61 | 4.19 | 1.62E+00 | 3.24E+03 |
| TOP | (+−)-2,6-DIMETHYL-7-OCTEN-4-ONE | 154 | 4203.89 | 3.12 | 2.78E−01 | 1.51E+04 |
| TOP | (2Z)-3-methyl-2-hexen-1-yl acetate (A) + (2E)-3-methyl-2-hexen-1-yl acetate (B) | 156 | 4131.05 | 3.11 | 2.73E−02 | 1.51E+05 |
| TOP | 3,7-DIMETHYL-1,3,6-OCTATRIENE | 136 | 3480.57 | 4.91 | 2.57E−02 | 1.35E+05 |
| TOP | ethyl heptanoate | 158 | 3052.89 | 3.58 | 7.17E−03 | 4.26E+05 |
| TOP | ETHYL 3-OXOBUTANOATE (A) <=> (2Z)-ETHYL 3-HYDROXY-2-BUTENOATE (B) | 130 | 2885.67 | 0.35 | 5.83E−02 | 4.95E+04 |

TABLE 6-continued

Perfuming Compounds Having a Fruity Note

| Type | Name | Molecular Weight | Volatility (μg/l air) | Log P (n-octanol/water) | Odor Threshold (μg/l air) | Odor Value |
|---|---|---|---|---|---|---|
| TOP | heptyl acetate | 158 | 2814.34 | 3.69 | 1.32E−01 | 2.14E+04 |
| TOP | 3-METHYLBUTYL BUTANOATE (A) + 2-METHYLBUTYL BUTANOATE (B) | 158 | 2611.71 | 3.52 | 2.08E−01 | 1.26E+04 |
| TOP | PENTYL BUTANOATE (A) + 2-METHYLBUTYL BUTANOATE (B) | 158 | 2611.71 | 3.52 | 2.08E−01 | 1.26E+04 |
| TOP | PENTYL BUTANOATE (A) + 2-METHYLBUTYL BUTANOATE (B) | 159 | 2611.71 | 3.52 | 2.08E−01 | 1.26E+04 |
| TOP | (+−)-4-PENTANOLIDE | 100 | 2355.15 | −0.12 | 6.62E−01 | 3.56E+03 |
| TOP | HEXYL ACETATE | 144 | 2316.04 | 3.09 | 1.32E−01 | 1.75E+04 |
| TOP | (+−)-2,6-DIMETHYL-5-HEPTENAL | 140 | 1889.68 | 3.15 | 2.11E−04 | 8.96E+06 |
| TOP | methyl (1RS,2SR)-2,6,6-trimethyl-3-cyclohexene-1-carboxylate (A) + methyl (1RS,2RS)-2,6,6-trimethyl-3-cyclohexene-1-carboxylate (B) | 182 | 1879.01 | 3.63 | 9.00E−03 | 2.09E+05 |
| TOP | (3Z)-3-hexen-1-yl butyrate | 170 | 1674.15 | 3.59 | 7.85E−02 | 2.13E+04 |
| TOP | hexyl 2-methylpropanoate | 172 | 1661.18 | 4.31 | 7.15E−01 | 2.32E+03 |
| TOP | ethyl (2E)-2,4-dimethyl-2-pentenoate | 156 | 1618.37 | 3.35 | 9.55E−03 | 1.69E+05 |
| TOP | 3-METHYLBUTANOIC ACID | 102 | 1530.76 | 1.49 | 2.23E−04 | 6.87E+06 |
| TOP | (+−)-1-PENTYL-2-PROPENYL ACETATE | 170 | 1506.95 | 3.79 | 4.84E−02 | 3.12E+04 |
| TOP | (3Z)-hex-3-en-1-yl methyl carbonate | 158 | 1506.33 | 2.97 | 4.58E−02 | 3.29E+04 |
| TOP | 3,5,5-TRIMETHYLHEXYL ACETATE | 186 | 1461.80 | 4.17 | 1.28E+00 | 1.14E+03 |
| TOP | ETHYL BENZOATE | 150 | 1285.12 | 2.51 | 1.54E−02 | 8.34E+04 |
| TOP | ALLYL HEPTANOATE | 170 | 1235.24 | 4.16 | 1.75E−02 | 7.06E+04 |
| TOP | 1-(3,3-DIMETHYL-1-CYCLOHEXYL)ETHYL FORMATE | 184 | 1129.46 | 4.01 | 2.05E−01 | 5.50E+03 |
| TOP | (2RS,4SR)-2-methyl-4-propyl-1,3-oxathiane (A) + (2RS,4RS)-2-methyl-4-propyl-1,3-oxathiane (B) | 160 | 1113.06 | 3.11 | 1.47E−03 | 7.57E+05 |

TABLE 6-continued

Perfuming Compounds Having a Fruity Note

| Type | Name | Molecular Weight | Volatility (µg/l air) | Log P (n-octanol/water) | Odor Threshold (µg/l air) | Odor Value |
|---|---|---|---|---|---|---|
| TOP | methyl cyclopentylideneacetate | 140 | 1091.46 | 2.02 | 2.80E−02 | 3.90E+04 |
| TOP | (+−)-methyl 2,2-dimethyl-6-methylidenecyclohexanecarboxylate | 182 | 1089.25 | 3.93 | 5.78E−04 | 1.88E+06 |
| TOP | (Z)-3-HEXENYL ISOBUTYRATE | 170 | 1073.97 | 3.57 | 4.54E−02 | 2.36E+04 |
| TOP | (−)-PROPYL (S)-2-(1,1-DIMETHYLPROPOXY)PROPANOATE | 202 | 995.16 | 3.17 | 4.98E−01 | 2.00E+03 |
| TOP | ALLYL HEXANOATE | 156 | 941.49 | 3.62 | 4.58E−02 | 2.06E+04 |
| TOP | (+−)-3,7-dimethyl-1,6-octadien-3-ol | 154 | 896.72 | 2.94 | 8.89E−05 | 1.01E+07 |
| TOP | (+−)-(Z)-3-HEXENYL 2-METHYLBUTANOATE | 184 | 833.05 | 3.84 | 1.96E−02 | 4.24E+04 |
| TOP | octyl acetate | 172 | 666.51 | 4.29 | 1.76E−01 | 3.78E+03 |
| TOP | (A) + (+−)-3,5,6,6-tetramethyl-4-methylidene-2-heptanone (B) + (+−)-(4E)-3,4,5,6,6-pentamethyl-4-hepten-2-one (C) + (+−)-(3Z)-3,4,5,6,6-pentamethyl-3-hepten-2-one (D) + (+−)-(3E)-3,4,5,6,6-pentamethyl-3-hepten-2-one (E) | 182 | 659.22 | 3.71 | 7.24E−02 | 9.11E+03 |
| TOP | 1-METHOXY-4-PROPYLBENZENE | 150 | 629.29 | 4.02 | 5.37E−04 | 1.17E+06 |
| TOP | (+−)-(3-methoxy-2-methylpropyl)benzene | 164 | 587.76 | 3.57 | 1.51E−02 | 3.89E+04 |
| TOP | 2-PHENYLETHYL FORMATE | 150 | 567.67 | 1.90 | 8.34E−04 | 6.81E+05 |
| TOP | (+−)-2-pentylcyclopentanone | 154 | 560.22 | 3.62 | 1.28E−03 | 4.38E+05 |
| TOP | METHYL PHENYLACETATE | 150 | 555.30 | 1.98 | 3.21E−04 | 1.73E+06 |
| TOP | (+)-(1R)-1,7,7-TRIMETHYL-BICYCLO[2.2.1]HEPTAN-2-ONE | 153 | 555.04 | 2.50 | 1.72E−01 | 3.23E+03 |
| TOP | 3-(2,2-DIMETHYLPROPYL)PYRIDINE | 149 | 516.21 | 3.17 | 2.82E−03 | 1.83E+05 |
| TOP | benzyl acetate | 150 | 507.38 | 2.04 | 5.24E−03 | 9.68E+04 |
| TOP | 2-CYCLOHEXYL ETHYL ACETATE | 170 | 489.45 | 4.25 | 4.49E−02 | 1.09E+04 |
| TOP | ETHYL 2-METHYL-1,3-DIOXOLANE-2-ACETATE | 174 | 479.20 | 1.12 | 1.62E−03 | 2.95E+05 |
| TOP | 1-PHENYL-1-ETHANOL | 122 | 470.00 | 1.42 | 2.98E−01 | 1.58E+03 |
| TOP | 2-METHYLPENTYL 2-METHYLPENTANOATE | 200 | 450.33 | 5.13 | 2.41E−01 | 1.87E+03 |
| TOP | (+−)-2-propylheptanenitrile | 153 | 439.00 | 3.67 | 7.83E−02 | 5.61E+03 |

TABLE 6-continued

Perfuming Compounds Having a Fruity Note

| Type | Name | Molecular Weight | Volatility (μg/l air) | Log P (n-octanol/water) | Odor Threshold (μg/l air) | Odor Value |
|---|---|---|---|---|---|---|
| TOP | (+−)-3-mercaptohexyl acetate | 175 | 421.09 | 2.64 | 2.72E−06 | 1.55E+08 |
| TOP | (+−)-3-mercaptohexyl acetate | 176 | 421.09 | 2.64 | 2.72E−06 | 1.55E+08 |
| TOP | (+−)-1,5-DIMETHYL-1-VINYL-4-HEXENYL ACETATE | 196 | 409.40 | 4.04 | 7.40E−02 | 5.53E+03 |
| TOP | (1RS,2RS)-2-(2-methyl-2-propanyl)cyclohexyl acetate (A) + (1RS,2SR)-2-(2-methyl-2-propanyl)cyclohexyl acetate (B) | 198 | 402.03 | 4.40 | 2.12E−02 | 1.90E+04 |
| TOP | (+−)-1-PHENYLETHYL ACETATE | 164 | 387.96 | 2.22 | 4.43E−02 | 8.75E+03 |
| TOP | (2RS,5SR,9RS,10SR)-2,6,9,10-tetramethyl-1-oxaspiro[4.5]deca-3,6-diene (A) + (2RS,5RS,9SR,10RS)-2,6,9,10-tetramethyl-1-oxaspiro[4.5]deca-3,6-diene (B) + (2RS,5RS,9RS,10SR)-2,6,9,10-tetramethyl-1-oxaspiro[4.5]deca-3,6-diene (C) + (2RS,5SR,9SR,10RS)-2,6,9,10-tetramethyl-1-oxaspiro[4.5]deca-3,6-diene (D) | 192 | 379.51 | 4.29 | 2.79E−02 | 1.36E+04 |
| TOP | ETHYL 2,6,6-TRIMETHYL-1,3-CYCLOHEXADIENE-1-CARBOXYLATE | 195 | 368.81 | 3.16 | 4.40E−03 | 8.38E+04 |
| TOP | (+−)-1,5-DIMETHYL-1-VINYL-4-HEXENYL ACETATE | 196 | 339.21 | 4.04 | 7.40E−02 | 4.58E+03 |
| TOP | (+−)-3,7-dimethyl-6-octen-1-yl formate (A) + (2E)-3,7-dimethyl-2,6-octadien-1-yl formate (B) | 184 | 322.28 | 3.79 | 5.28E−04 | 6.10E+05 |
| TOP | (+−)-ethyl 2-acetyl-4-methyl-4-pentenoate | 184 | 295.22 | 2.15 | 3.64E−03 | 8.10E+04 |
| TOP | cis-4-(2-methyl-2-propanyl)cyclohexyl acetate (A) + trans-4-(2-methyl-2-propanyl)cyclohexyl acetate (B) | 198 | 291.85 | 4.47 | 5.43E−02 | 5.37E+03 |
| TOP | ETHYL PHENYLACETATE | 164 | 269.77 | 2.10 | 4.19E−04 | 6.44E+05 |

TABLE 6-continued

Perfuming Compounds Having a Fruity Note

| Type | Name | Molecular Weight | Volatility (µg/l air) | Log P (n-octanol/water) | Odor Threshold (µg/l air) | Odor Value |
|---|---|---|---|---|---|---|
| TOP | (+−)-2,2,5-trimethyl-5-pentylcyclopentanone | 196 | 265.42 | 4.63 | 3.25E−02 | 8.16E+03 |
| TOP | methyl (2E)-2-nonenoate | 170 | 264.84 | 4.05 | 5.84E−02 | 4.53E+03 |
| TOP | (+−)-2,4-dimethyl-4-phenyltetrahydrofuran | 176 | 263.73 | 3.02 | 5.04E−04 | 5.23E+05 |
| TOP | (+−)-3,7-DIMETHYL-6-OCTENYL FORMATE | 184 | 262.84 | 4.16 | 1.72E−03 | 1.53E+05 |
| TOP | ALLYL (3-METHYLBUTOXY)ACETATE (A) + (+−)-ALLYL (2-METHYLBUTOXY)ACETATE (B) | 186 | 261.90 | 2.79 | 9.89E−05 | 2.65E+06 |
| TOP | hexyl (2E)-2-methyl-2-butenoate | 184 | 256.81 | 4.80 | 1.16E−02 | 2.22E+04 |
| TOP | (2RS,5SR)-6-ethyl-2,10,10-trimethyl-1-oxaspiro[4.5]deca-3,6-diene (A) + (2RS,5RS)-6-ethyl-2,10,10-trimethyl-1-oxaspiro[4.5]deca-3,6-diene (B) | 206 | 252.44 | 5.07 | 7.71E−03 | 3.27E+04 |
| TOP | cis-4-(2-methyl-2-propanyl)cyclohexyl acetate (A) + trans-4-(2-methyl-2-propanyl)cyclohexyl acetate (B) | 198 | 229.76 | 4.18 | 2.33E−02 | 9.87E+03 |
| TOP | (3Z)-3-hexen-1-yl (3Z)-3-hexenoate | 196 | 210.68 | 4.22 | 5.17E−02 | 4.08E+03 |
| TOP | (Z)-3,7-DIMETHYL-2,6-OCTADIENAL (A) + (E)-3,7-DIMETHYL-2,6-OCTADIENAL (B) | 152 | 202.66 | 2.68 | 4.12E−03 | 4.92E+04 |
| TOP | 2-PHENYLETHYL ACETATE | 164 | 201.26 | 2.49 | 2.14E−03 | 9.38E+04 |
| TOP | 1,1-DIMETHYL-2-PHENYLETHYL ACETATE | 192 | 198.02 | 3.45 | 5.16E−02 | 3.84E+03 |
| TOP | 1-methoxy-4-[(1E)-1-propen-1-yl]benzene | 148 | 184.60 | 3.58 | 1.23E−03 | 1.51E+05 |
| TOP | 4-PHENYL-2-BUTANONE | 148 | 176.55 | 1.79 | 2.22E−04 | 7.95E+05 |
| TOP | 4-METHYLPHENYL ISOBUTYRATE | 178 | 167.81 | 3.03 | 1.66E−05 | 1.01E+07 |
| TOP | 2-PHENYLETHANOL | 122 | 159.75 | 1.41 | 1.02E−04 | 1.56E+06 |
| TOP | (1R,4R)-8-MERCAPTO-3-P-MENTHANONE | 186 | 155.12 | 2.99 | 3.43E−05 | 4.52E+06 |

TABLE 6-continued

Perfuming Compounds Having a Fruity Note

| Type | Name | Molecular Weight | Volatility (µg/l air) | Log P (n-octanol/water) | Odor Threshold (µg/l air) | Odor Value |
|---|---|---|---|---|---|---|
| TOP | (+−)-(E)-1-(2,2-DIMETHYL-6-METHYLENE-1-CYCLOHEXYL)-2-BUTEN-1-ONE | 192 | 152.99 | 4.11 | 3.73E−03 | 4.10E+04 |
| TOP | (2E)-1-[(1RS,2SR)-2,6,6-trimethyl-3-cyclohexen-1-yl]-2-buten-1-one | 192 | 143.53 | 4.13 | 1.70E−05 | 8.44E+06 |
| TOP | [2-(1-ETHOXYETHOXY)ETHYL]BENZENE (A) + 1,1-BIS(2-PHENYLETHOXY)ETHANE (B) | 270 | 136.67 | 2.96 | 1.59E−03 | 8.59E+04 |
| TOP | 3,7-DIMETHYL-6-OCTENYL ACETATE | 198 | 128.72 | 4.22 | 2.75E−02 | 4.68E+03 |
| TOP | 5-METHYL-3-HEPTANONE OXIME | 143 | 128.04 | 2.45 | 8.80E−03 | 1.45E+04 |
| TOP | (2Z)-3,7-dimethyl-2,6-octadien-1-yl acetate | 196 | 123.21 | 3.81 | 6.02E−02 | 2.05E+03 |
| TOP | (2E)-1-(2,6,6-trimethyl-1,3-cyclohexadien-1-yl)-2-buten-1-one | 190 | 119.10 | 3.27 | 1.68E−05 | 7.09E+06 |
| TOP | 2,4,6-TRIMETHYL-4-PHENYL-1,3-DIOXANE | 206 | 113.83 | 2.90 | 7.82E−03 | 1.46E+04 |
| TOP | BENZYL PROPANOATE | 164 | 113.60 | 2.35 | 2.81E−02 | 4.04E+03 |
| TOP | (+−)-(2E)-1-(2,6,6-trimethyl-2-cyclohexen-1-yl)-2-buten-1-one | 192 | 113.31 | 3.65 | 1.04E−04 | 1.09E+06 |
| TOP | ETHYL TRICYCLO[5.2.1.0.(2,6)]DECANE-2-CARBOXYLATE | 208 | 111.67 | 4.32 | 6.87E−05 | 1.63E+06 |
| TOP | (+−)-(2E)-1-(2,6,6-trimethyl-2-cyclohexen-1-yl)-2-buten-1-one | 192 | 110.53 | 3.65 | 1.04E−04 | 1.06E+06 |
| TOP | 3-METHYLBUTYL 2-PHENYLETHYL ETHER | 192 | 110.11 | 4.31 | 1.38E−02 | 7.96E+03 |
| TOP | (+−)-4-OCTANOLIDE | 142 | 108.41 | 1.80 | 2.32E−05 | 4.67E+06 |
| TOP | HEXYL HEXANOATE | 200 | 105.52 | 5.56 | 9.98E−02 | 1.06E+03 |
| Middle | (2RS,4SR)-4-methyl-2-phenyltetrahydro-2H-pyran (A) + (2RS,4RS)-4-methyl-2-phenyltetrahydro-2H-pyran (B) | 176 | 99.84 | 3.47 | 1.04E−03 | 9.61E+04 |
| Middle | tricyclo[5.2.1.0~2,6~]dec-3-en-8-yl acetate (A) + tricyclo[5.2.1.0~2,6~]dec-4-en-8-yl acetate (B) | 192 | 96.53 | 3.73 | 7.19E−04 | 1.34E+05 |

TABLE 6-continued

| | Perfuming Compounds Having a Fruity Note | | | | | |
|---|---|---|---|---|---|---|
| Type | Name | Molecular Weight | Volatility (µg/l air) | Log P (n-octanol/water) | Odor Threshold (µg/l air) | Odor Value |
| Middle | 3-HYDROXY-2-METHYL-4(4H)-PYRANONE | 126 | 92.42 | 0.11 | 4.17E−04 | 2.22E+05 |
| Middle | (2E)-1-(2,6,6-trimethyl-1,3-cyclohexadien-1-yl)-2-buten-1-one | 190 | 91.38 | 3.33 | 3.00E−06 | 3.04E+07 |
| Middle | (E)-3,7-DIMETHYL-2,6-OCTADIENYL ACETATE (A) + 3,7-DIMETHYL-6-OCTENYL ACETATE (B) | 196 | 85.23 | 3.99 | 3.57E−02 | 2.39E+03 |
| Middle | GERANYL ACETATE (A) + NERYL ACETATE (B) | 196 | 85.23 | 3.99 | 3.57E−02 | 2.39E+03 |
| Middle | (E)-3,7-DIMETHYL-2,6-OCTADIENYL ACETATE | 196 | 85.23 | 3.99 | 3.57E−02 | 2.39E+03 |
| Middle | (2E)-1-(2,6,6-trimethyl-1-cyclohexen-1-yl)-2-buten-1-one | 192 | 81.66 | 3.63 | 2.18E−04 | 3.75E+05 |
| Middle | 4-CYCLOHEXYL-2-METHYL-2-BUTANOL | 170 | 79.34 | 3.93 | 2.83E−02 | 2.81E+03 |
| Middle | (E)-3,7-DIMETHYL-2,6-OCTADIENYL ACETATE | 196 | 79.23 | 3.99 | 3.57E−02 | 2.22E+03 |
| Middle | ALLYL 3-CYCLOHEXYLPROPANOATE | 196 | 75.80 | 4.51 | 7.96E−03 | 9.53E+03 |
| Middle | 2-PHENYLETHYL PIVALATE | 206 | 71.44 | 3.69 | 3.85E−02 | 1.86E+03 |
| Middle | 2-PHENYLETHYL ISOBUTYRATE | 192 | 67.38 | 3.16 | 6.70E−03 | 1.01E+04 |
| Middle | (+−)-(E)-4-METHYL-3-DECEN-5-OL | 170 | 64.15 | 3.63 | 6.78E−04 | 9.46E+04 |
| Middle | (+−)-(3E)-4-(2,6,6-trimethyl-2-cyclohexen-1-yl)-3-buten-2-one (A) + (3E)-4-(2,6,6-trimethyl-1-cyclohexen-1-yl)-3-buten-2-one (B); | 192 | 64.00 | 4.22 | 5.08E−04 | 1.26E+05 |
| Middle | BENZYL 3-METHYLBUTANOATE | 192 | 63.56 | 3.45 | 7.31E−03 | 8.70E+03 |
| Middle | METHYL (E)-3-PHENYL-2-PROPENOATE | 162 | 61.65 | 2.56 | 3.13E−03 | 1.97E+04 |
| Middle | (+−)-6-propyltetrahydro-2H-pyran-2-one | 142 | 57.43 | 1.47 | 2.17E−04 | 2.65E+05 |
| Middle | (+−)-1,3-DIMETHYL-3-PHENYLBUTYL ACETATE | 220 | 50.65 | 3.02 | 1.06E−02 | 4.77E+03 |
| Bottom | (+−)-(1S,4aR,8S,8aR)-2,2,6,8-tetramethyl-1,2,3,4,4a,5,8,8a-octahydro-1-naphthalenol | 208 | 48.90 | 5.24 | 8.15E−04 | 6.00E+04 |

TABLE 6-continued

Perfuming Compounds Having a Fruity Note

| Type | Name | Molecular Weight | Volatility (μg/l air) | Log P (n-octanol/water) | Odor Threshold (μg/l air) | Odor Value |
|---|---|---|---|---|---|---|
| Bottom | 2-ETHYL-3-HYDROXY-4(4H)-PYRANONE | 141 | 48.86 | 0.76 | 6.45E−05 | 7.57E+05 |
| Bottom | ALLYL (CYCLOHEXYLOXY)ACETATE | 198 | 47.01 | 2.62 | 4.66E−05 | 1.01E+06 |
| Bottom | 1-(3,3-dimethyl-1-cyclohexen-1-yl)-4-penten-1-one (A) + 1-(5,5-dimethyl-1-cyclohexen-1-yl)-4-penten-1-one (B) | 192 | 47.01 | 3.89 | 1.64E−06 | 2.87E+07 |
| Bottom | 1-(5,5-dimethyl-1-cyclohexen-1-yl)-4-penten-1-one | 192 | 38.43 | 3.89 | 1.64E−06 | 2.34E+07 |
| Bottom | (+−)-2-PHENYLETHYL 2-METHYLBUTANOATE | 206 | 37.73 | 3.64 | 8.56E−03 | 4.41E+03 |
| Bottom | ethyl (2E,4Z)-2,4-decadienoate | 196 | 36.76 | 4.69 | 3.07E−04 | 1.20E+05 |
| Bottom | (+−)-3,4'-dimethylspiro[oxirane-2,9'-tricyclo[6.2.1.0~2,7~]undec[4]ene | 204 | 36.76 | 4.58 | 9.93E−04 | 3.70E+04 |
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 36.33 | 4.83 | 1.92E−04 | 1.89E+05 |
| Bottom | (+−)-(E)-3-METHYL-4-(2,6,6-TRIMETHYL-2-CYCLOHEXEN-1-YL)-3-BUTEN-2-ONE | 206 | 36.33 | 4.83 | 1.92E−04 | 1.89E+05 |
| Bottom | TRICYCLO[5.2.1.0(2,6)]DEC-3-EN-8-YL PROPANOATE (A) + TRICYCLO[5.2.1.0(2,6)]DEC-4-EN-8-YL PROPANOATE (B) | 206 | 35.82 | 4.38 | 2.44E−04 | 1.47E+05 |
| Bottom | 1,1-DIMETHYL-2-PHENYLETHYL BUTANOATE | 220 | 34.65 | 4.42 | 2.68E−02 | 1.29E+03 |
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 34.44 | 4.28 | 1.70E−04 | 2.03E+05 |

TABLE 6-continued

Perfuming Compounds Having a Fruity Note

| Type | Name | Molecular Weight | Volatility (μg/l air) | Log P (n-octanol/water) | Odor Threshold (μg/l air) | Odor Value |
|---|---|---|---|---|---|---|
| Bottom | BENZYL (E)-2-METHYL-2-BUTENOATE | 190 | 33.88 | 3.32 | 3.07E−04 | 1.11E+05 |
| Bottom | (+−)-4-NONANOLIDE | 156 | 27.42 | 2.45 | 1.45E−04 | 1.89E+05 |
| Bottom | (1RS,2RS,6RS,7RS,8SR)-tricyclo[5.2.1.0~2,6~]dec-4-en-8-yl 2-methylpropanoate (A) + (1RS,2SR,6RS,7RS,8SR)-tricyclo[5.2.1.0~2,6~]dec-3-en-8-yl 2-methylpropanoate (B) | 220 | 26.90 | 4.79 | 2.26E−03 | 1.19E+04 |
| Bottom | 9-DECEN-1-OL | 156 | 26.88 | 3.70 | 8.92E−03 | 3.01E+03 |
| Bottom | ETHYL (2E)-2,4,7-DECATRIENOATE | 194 | 25.34 | 4.25 | 1.49E−02 | 1.70E+03 |
| Bottom | 5-NONANOLIDE | 156 | 23.87 | 1.82 | 1.16E−05 | 2.06E+06 |
| Bottom | (+−)-(E)-TRANS-alpha-IRONE (A) + (+−)-(E)-CIS-alpha-IRONE (B) + (+−)-(E)-beta-IRONE (C) | 206 | 22.11 | 4.05 | 9.26E−04 | 2.39E+04 |
| Bottom | (+−)-TRANS-3-METHYL-4-NONANOLIDE | 170 | 21.05 | 2.59 | 8.33E−04 | 2.53E+04 |
| Bottom | ETHYL (E)-3-PHENYL-2-PROPENOATE | 176 | 20.55 | 3.00 | 2.38E−05 | 8.62E+05 |
| Bottom | (E)-3-PHENYL-2-PROPENYL ACETATE | 176 | 20.47 | 2.52 | 1.87E−04 | 1.10E+05 |
| Bottom | 4-METHOXYBENZYL ACETATE | 180 | 17.59 | 2.18 | 9.24E−05 | 1.90E+05 |
| Bottom | 1,5,9-TRIMETHYL-4,8-DECADIENYL ACETATE | 238 | 14.74 | 5.28 | 3.28E−04 | 4.49E+04 |
| Bottom | ETHYL 2,3-EPDXY-3-PHENYLBUTANOATE | 206 | 12.97 | 2.30 | 2.28E−05 | 5.68E+05 |
| Bottom | (+−)-2,2,2-TRICHLORO-1-PHENYLETHYL ACETATE | 268 | 11.96 | 3.20 | 1.15E−03 | 1.04E+04 |
| Bottom | (3Z)-3-hexen-1-yl benzoate | 204 | 11.05 | 4.21 | 4.37E−02 | 2.53E+02 |
| Bottom | (+−)-4-DECANOLIDE | 170 | 10.49 | 3.02 | 1.61E−04 | 6.51E+04 |
| Bottom | 2-phenoxyethyl 2-methylpropanoate | 208 | 10.05 | 2.82 | 3.01E−02 | 3.34E+02 |
| Bottom | ALLYL PHENOXYACETATE | 192 | 9.94 | 2.04 | 1.22E−03 | 8.13E+03 |
| Bottom | (+−)-6-pentyltetrahydro-2H-pyran-2-one | 170 | 9.61 | 2.22 | 3.72E−05 | 2.58E+05 |
| Bottom | diethyl cis-1,4-cyclohexanedicarboxylate (A) + diethyl trans-1,4-cyclohexanedicarboxylate (B) | 228 | 8.51 | 2.65 | 2.87E−03 | 2.97E+03 |

TABLE 6-continued

Perfuming Compounds Having a Fruity Note

| Type | Name | Molecular Weight | Volatility (µg/l air) | Log P (n-octanol/water) | Odor Threshold (µg/l air) | Odor Value |
|---|---|---|---|---|---|---|
| Bottom | (E)-3-PHENYL-2-PROPENYL PROPANOATE | 190 | 8.14 | 3.09 | 1.28E−04 | 6.35E+04 |
| Bottom | (+−)-(E)-8-DECEN-5-OLIDE (A) + (+−)-(Z)-8-DECEN-5-OLIDE (B) | 168 | 6.89 | 2.70 | 5.14E−04 | 1.34E+04 |
| Bottom | 8(9)-METHOXY-TRICYCLO[5.2.1.0(2,6)]DECANE-3(4)-CARBALDEHYDE | 193 | 5.87 | 5.00 | 4.02E−05 | 1.46E+05 |
| Bottom | 4-(4-METHOXYPHENYL)-2-BUTANONE | 178 | 5.58 | 2.06 | 5.88E−06 | 9.49E+05 |
| Bottom | 6-hexyltetrahydro-2H-pyran-2-one | 184 | 4.64 | 3.00 | 5.85E−05 | 7.93E+04 |
| Bottom | (+)-(1S,1'R)-2-[1-(3',3'-DIMETHYL-1'-CYCLOHEXYL)ETHOXY]-2-METHYLPROPYL PROPANOATE | 284 | 4.39 | 5.46 | 3.69E−04 | 1.19E+04 |
| Bottom | (+)-(1S,2S,3S,5R)-2,6,6-trimethylspiro[bicyclo[3.1.1]heptane-3,1'-cyclohexane]-2'-en-4'-one | 218 | 4.14 | 4.39 | 6.32E−04 | 6.54E+03 |
| Bottom | HEXYL 2-HYDROXYBENZOATE | 222 | 3.82 | 5.55 | 5.50E−03 | 6.95E+02 |
| Bottom | (+−)-5-heptyldihydro-2(3H)-furanone | 184 | 3.67 | 3.32 | 3.16E−05 | 1.16E+05 |
| Bottom | (+−)-(1E)-1-(2,6,6-trimethyl-2-cyclohexen-1-yl)-1,6-heptadien-3-one (A) + (1E)-1-(2,6,6-trimethyl-1-cyclohexen-1-yl)-1,6-heptadien-3-one (B) | 232 | 3.01 | 4.86 | 7.14E−03 | 4.22E+02 |
| Bottom | 9-ETHYLIDENE-3-OXATRICYCLO[6.2.1.0(2,7)]UNDECAN-4-ONE (A) + 10-ETHYLIDENE-3-OXATRICYCLO[6.2.1.0(2,7)]...(B) | 192 | 2.10 | 2.29 | 1.42E−04 | 1.48E+04 |
| Bottom | (1'R)-2-[2-(4'-METHYL-3'-CYCLOHEXEN-1'-YL)PROPYL]CYCLOPENTANONE | 220 | 2.05 | 5.19 | 1.66E−04 | 1.24E+04 |
| Bottom | (E)-2-METHOXY-4-(1-PROPENYL)PHENYL ACETATE | 206 | 1.85 | 2.56 | 4.08E−07 | 4.54E+06 |
| Bottom | (+−)-4,6,6,7,8,8-hexamethyl-1,3,4,6,7,8-hexahydrocyclopenta[g]isochromene | 258 | 1.59 | 6.57 | 2.62E−04 | 6.08E+03 |

TABLE 6-continued

Perfuming Compounds Having a Fruity Note

| Type | Name | Molecular Weight | Volatility (µg/l air) | Log P (n-octanol/water) | Odor Threshold (µg/l air) | Odor Value |
|---|---|---|---|---|---|---|
| Bottom | methyl {(1RS,2RS)-3-oxo-2-[(2Z)-2-penten-1-yl]cyclopentyl}acetate | 224 | 1.59 | 2.33 | 5.56E−03 | 2.86E+02 |
| Bottom | (+−)-5-octyldihydro-2(3H)-furanone | 198 | 1.44 | 3.82 | 2.85E−05 | 5.05E+04 |
| Bottom | (2E)-2-benzylideneoctanal | 216 | 1.15 | 4.86 | 1.91E−03 | 6.01E+02 |
| Bottom | 4-formyl-2-methoxyphenyl 2-methylpropanoate | 222 | 1.01 | 1.90 | 7.33E−05 | 1.38E+04 |
| Bottom | (+−)-6-heptyltetrahydro-2H-pyran-2-one | 198 | 0.90 | 3.42 | 1.27E−04 | 7.06E+03 |
| Bottom | BENZYL BENZOATE | 212 | 0.85 | 3.64 | 3.67E−02 | 2.31E+01 |
| Bottom | BENZYL BENZOATE | 213 | 0.85 | 3.64 | 3.67E−02 | 2.31E+01 |
| Bottom | (10E)-oxacycloheptadec-10-en-2-one | 252 | 0.74 | 6.15 | 4.77E−04 | 1.55E+03 |
| Bottom | (E)-2-PENTYL-3-PHENYL-2-PROPENAL | 202 | 0.68 | 4.30 | 3.64E−04 | 1.87E+03 |
| Bottom | 4-(4-HYDROXY-1-PHENYL)-2-BUTANONE | 164 | 0.36 | 0.93 | 2.05E−07 | 1.75E+06 |
| Bottom | 2-PHENYLETHYL PHENYLACETATE | 240 | 0.20 | 3.59 | 9.08E−04 | 2.24E+02 |

TABLE 7

Perfuming Compounds Having a Citrus Note

| Type | Name | Molecular Weight | Volatility (µg/l air) | Log P (n-octanol/water) | Odor Threshold (µg/l air) | Odor Value |
|---|---|---|---|---|---|---|
| Top | hexanal | 100 | 68294.85 | 2.00 | 1.76E−03 | 3.88E+07 |
| Top | (+−)-ISOPROPYL 2-METHYLBUTANOATE | 144 | 51367.63 | 2.85 | 8.42E−03 | 6.10E+06 |
| Top | (2E)-2-HEXENAL | 98 | 33708.26 | 1.62 | 2.53E−03 | 1.33E+07 |
| Top | (+)-LIMONENE | 136 | 10216.93 | 5.40 | 1.29E−01 | 7.92E+04 |
| Top | 1-methyl-4-(2-propanyl)-1,4-cyclohexadiene | 136 | 4298.67 | 5.87 | 1.16E−01 | 3.70E+04 |
| Top | (+−)-2,6-DIMETHYL-7-OCTEN-4-ONE | 154 | 4203.89 | 3.12 | 2.78E−01 | 1.51E+04 |
| Top | heptyl acetate | 158 | 2814.34 | 3.69 | 1.32E−01 | 2.14E+04 |
| Top | nonanal | 142 | 2777.63 | 3.42 | 8.14E−03 | 3.41E+05 |
| Top | (+−)-4-PENTANOLIDE | 100 | 2355.15 | −0.12 | 6.62E−01 | 3.56E+03 |
| Top | 1-(3,3-DIMETHYL-1-CYCLOHEXYL)ETHYL FORMATE | 184 | 1129.46 | 4.01 | 2.05E−01 | 5.50E+03 |
| Top | (−)-PROPYL (S)-2-(1,1-DIMETHYLPROPOXY)PROPANOATE | 202 | 995.16 | 3.17 | 4.98E−01 | 2.00E+03 |
| Top | (3Z)-1,3-undecadien-5-yne (A) + (3E)-1,3-undecadien-5-yne (B) | 148 | 990.87 | 5.11 | 3.32E−03 | 2.98E+05 |

TABLE 7-continued

| | | | | Log P | | |
|---|---|---|---|---|---|---|
| Type | Name | Molecular Weight | Volatility (μg/l air) | (n-octanol/ water) | Odor Threshold (μg/l air) | Odor Value |
| Top | (+−)-3,7-dimethyl-1,6-octadien-3-ol | 154 | 896.72 | 2.94 | 8.89E−05 | 1.01E+07 |
| Top | (+−)-3,7-dimethyl-1,6-octadien-3-ol | 154 | 896.72 | 2.94 | 8.89E−05 | 1.01E+07 |
| Top | (+−)-3,7-dimethyl-1,6-octadien-3-ol | 154 | 896.72 | 2.94 | 8.89E−05 | 1.01E+07 |
| Top | (E)-4-DECENAL | 154 | 691.34 | 3.73 | 7.59E−05 | 9.11E+06 |
| Top | octyl acetate | 172 | 666.51 | 4.29 | 1.76E−01 | 3.78E+03 |
| Top | (A) + (+−)-3,5,6,6-tetramethyl-4-methylidene-2-heptanone (B) + (+−)-(4E)-3,4,5,6,6-pentamethyl-4-hepten-2-one (C) + (+−)-(3Z)-3,4,5,6,6-pentamethyl-3-hepten-2-one (D) + (+−)-(3E)-3,4,5,6,6-pentamethyl-3-hepten-2-one (E) | 182 | 659.22 | 3.71 | 7.24E−02 | 9.11E+03 |
| Top | (+−)-(3-methoxy-2-methylpropyl)benzene | 164 | 587.76 | 3.57 | 1.51E−02 | 3.89E+04 |
| Top | 2-PHENYLETHYL FORMATE | 150 | 567.67 | 1.90 | 8.34E−04 | 6.81E+05 |
| Top | (+−)-2-propylheptanenitrile | 153 | 439.00 | 3.67 | 7.83E−02 | 5.61E+03 |
| Top | (+−)-1,5-DIMETHYL-1-VINYL-4-HEXENYL ACETATE | 196 | 409.40 | 4.04 | 7.40E−02 | 5.53E+03 |
| Top | (+−)-1-PHENYLETHYL ACETATE | 164 | 387.96 | 2.22 | 4.43E−02 | 8.75E+03 |
| Top | (+−)-1,5-DIMETHYL-1-VINYL-4-HEXENYL ACETATE | 196 | 339.21 | 4.04 | 7.40E−02 | 4.58E+03 |
| Top | cis-4-(2-methyl-2-propanyl)cyclohexyl acetate (A) + trans-4-(2-methyl-2-propanyl)cyclohexyl acetate (B) | 198 | 291.85 | 4.47 | 5.43E−02 | 5.37E+03 |
| Top | (Z)-3,7-DIMETHYL-1,6-NONADIEN-3-OL (A) + (E)-3,7-DIMETHYL-1,6-NONADIEN-3-OL (B) | 168 | 283.43 | 3.54 | 1.38E−03 | 2.05E+05 |
| Top | ALLYL (3-METHYLBUTOXY)ACETATE (A) + (+−)-ALLYL (2-METHYLBUTOXY)ACETATE (B) | 186 | 261.90 | 2.79 | 9.89E−05 | 2.65E+06 |

TABLE 7-continued

| | Perfuming Compounds Having a Citrus Note | | | | | |
|---|---|---|---|---|---|---|
| Type | Name | Molecular Weight | Volatility (μg/l air) | Log P (n-octanol/water) | Odor Threshold (μg/l air) | Odor Value |
| Top | (Z)-3,7-DIMETHYL-2,6-OCTADIENAL (A) + (E)-3,7-DIMETHYL-2,6-OCTADIENAL (B) | 152 | 202.66 | 2.68 | 4.12E−03 | 4.92E+04 |
| Middle | (2RS,4SR)-4-methyl-2-phenyltetrahydro-2H-pyran (A) + (2RS,4RS)-4-methyl-2-phenyltetrahydro-2H-pyran (B) | 176 | 99.84 | 3.47 | 1.04E−03 | 9.61E+04 |
| Middle | tricyclo[5.2.1.0~2,6~]dec-3-en-8-yl acetate (A) + tricyclo[5.2.1.0~2,6~]dec-4-en-8-yl acetate (B) | 192 | 96.53 | 3.73 | 7.19E−04 | 1.34E+05 |
| Middle | 3,7-DIMETHYL-2,6-OCTADIEN-1-OL | 154 | 89.88 | 2.97 | 7.69E−04 | 1.17E+05 |
| Middle | (E)-3,7-DIMETHYL-2,6-OCTADIEN-1-OL | 154 | 89.88 | 2.97 | 7.69E−04 | 1.17E+05 |
| Middle | CITRONELLOL (A) + GERANIOL (B) | 154 | 89.88 | 2.97 | 7.69E−04 | 1.17E+05 |
| Middle | (E)-3,7-DIMETHYL-2,6-OCTADIEN-1-OL | 154 | 89.88 | 2.97 | 7.69E−04 | 1.17E+05 |
| Middle | (Z)-3,7-DIMETHYL-2,6-OCTADIEN-1-OL | 154 | 86.02 | 2.91 | 1.56E−02 | 5.51E+03 |
| Middle | 4-CYCLOHEXYL-2-METHYL-2-BUTANOL | 170 | 79.34 | 3.93 | 2.83E−02 | 2.81E+03 |
| Middle | (+−)-3,7-DIMETHYL-1-OCTANOL | 158 | 76.57 | 4.24 | 4.59E−02 | 1.67E+03 |
| Middle | 3,7-DIMETHYL-2,6-OCTADIEN-1-OL | 154 | 67.92 | 2.97 | 7.69E−04 | 8.83E+04 |
| Middle | (+−)-6-propyltetrahydro-2H-pyran-2-one | 142 | 57.43 | 1.47 | 2.17E−04 | 2.65E+05 |
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 36.33 | 4.83 | 1.92E−04 | 1.89E+05 |
| Bottom | TRICYCLO[5.2.1.0(2,6)]DEC-3-EN-8-YL PROPANOATE (A) + TRICYCLO[5.2.1.0(2,6)]DEC-4-EN-8-YL PROPANOATE (B) | 206 | 35.82 | 4.38 | 2.44E−04 | 1.47E+05 |

TABLE 7-continued

Perfuming Compounds Having a Citrus Note

| Type | Name | Molecular Weight | Volatility (µg/l air) | Log P (n-octanol/ water) | Odor Threshold (µg/l air) | Odor Value |
|---|---|---|---|---|---|---|
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 34.44 | 4.28 | 1.70E−04 | 2.03E+05 |
| Bottom | 9-DECEN-1-OL | 156 | 26.88 | 3.70 | 8.92E−03 | 3.01E+03 |
| Bottom | 2-ETHOXYNAPHTHALENE | 172 | 22.67 | 3.82 | 3.57E−03 | 6.35E+03 |
| Bottom | 3-(3,3-dimethyl-2,3-dihydro-1H-inden-5-yl)propanal (A) + 3-(1,1-dimethyl-2,3-dihydro-1H-inden-4-yl)propanal (B) + 3-(1,1-dimethyl-2,3-dihydro-1H-inden-5-yl)propanal (C) | 181 | 13.68 | 4.63 | 4.00E−03 | 3.42E+03 |
| Bottom | (+−)-2,2,2-TRICHLORO-1-PHENYLETHYL ACETATE | 268 | 11.96 | 3.20 | 1.15E−03 | 1.04E+04 |
| Bottom | (3Z)-3-hexen-1-yl benzoate | 204 | 11.05 | 4.21 | 4.37E−02 | 2.53E+02 |
| Bottom | 8(9)-METHOXY-TRICYCLO[5.2.1.0(2,6)]DECANE-3(4)-CARBALDEHYDE | 193 | 5.87 | 5.00 | 4.02E−05 | 1.46E+05 |
| Bottom | (+−)-(3,7-DIMETHYL-6-OCTENYLOXY)ACETALDEHYDE | 198 | 4.70 | 4.33 | 8.95E−04 | 5.26E+03 |
| Bottom | (+−)-(3,7-DIMETHYL-6-OCTENYLOXY)ACETALDEHYDE | 198 | 4.70 | 4.33 | 8.95E−04 | 5.26E+03 |
| Bottom | HEXYL 2-HYDROXYBENZOATE | 222 | 3.82 | 5.55 | 5.50E−03 | 6.95E+02 |
| Bottom | methyl 2-((1RS,2RS)-3-oxo-2-pentylcyclopentyl)acetate | 226 | 2.12 | 2.92 | 5.77E−04 | 3.67E+03 |
| Bottom | 9-ETHYLIDENE-3-OXATRICYCLO[6.2.1.0(2,7)]UNDECAN-4-ONE (A) + 10-ETHYLIDENE-3-OXATRICYCLO[6.2.1.0(2,7)] . . . (B) | 192 | 2.10 | 2.29 | 1.42E−04 | 1.48E+04 |
| Bottom | (E)-2-METHOXY-4-(1-PROPENYL)PHENYL ACETATE | 206 | 1.85 | 2.56 | 4.08E−07 | 4.54E+06 |
| Bottom | BENZYL BENZOATE | 213 | 0.85 | 3.64 | 3.67E−02 | 2.31E+01 |
| Bottom | (10E)-oxacycloheptadec-10-en-2-one | 252 | 0.74 | 6.15 | 4.77E−04 | 1.55E+03 |
| Bottom | (E)-2-PENTYL-3-PHENYL-2-PROPENAL | 202 | 0.68 | 4.30 | 3.64E−04 | 1.87E+03 |

TABLE 7-continued

Perfuming Compounds Having a Citrus Note

| Type | Name | Molecular Weight | Volatility (µg/l air) | Log P (n-octanol/water) | Odor Threshold (µg/l air) | Odor Value |
|---|---|---|---|---|---|---|
| Bottom | 2-PHENYLETHYL PHENYLACETATE | 240 | 0.20 | 3.59 | 9.08E−04 | 2.24E+02 |

TABLE 8

Perfuming Compounds Having a Sweet Note

| Type | Name | Molecular Weight | Volatility (µg/l air) | Log P (n-octanol/water) | Odor Threshold (µg/l air) | Odor Value |
|---|---|---|---|---|---|---|
| Top | ETHYL ACETATE | 88 | 404705.61 | 0.80 | 7.26E−01 | 5.58E+05 |
| Top | BUTYL ACETATE | 116 | 117207.52 | 2.11 | 4.18E−01 | 2.80E+05 |
| Top | 3-METHYLBUTYL ACETATE (A) + (+−)-2-METHYLBUTYL ACETATE (B) | 130 | 51307.81 | 2.65 | 5.92E−02 | 8.67E+05 |
| Top | (+−)-3-HYDROXY-2-BUTANONE | 88 | 33382.87 | −1.03 | 1.46E−02 | 2.28E+06 |
| Top | 2-FURANMETHANETHIOL | 114 | 29677.31 | 1.70 | 1.43E−09 | 2.08E+13 |
| Top | 1-BUTANOL | 74 | 17700.00 | 0.88 | 8.70E−02 | 2.03E+05 |
| Top | (+−)-4-methyl-4-penten-2-yl 2-methylpropanoate | 170 | 9902.98 | 3.57 | 2.26E−01 | 4.39E+04 |
| Top | ETHYL HEXANOATE | 145 | 9675.10 | 3.12 | 9.11E−04 | 1.06E+07 |
| Top | BENZALDEHYDE | 106 | 8207.00 | 1.33 | 4.26E−02 | 1.93E+05 |
| Top | 2,3,5-TRIMETHYLPYRAZINE | 122 | 7897.31 | 1.27 | 2.82E−04 | 2.80E+07 |
| Top | 5-METHYL-2-HEPTEN-4-ONE | 126 | 5525.83 | 1.98 | 7.62E−07 | 7.26E+09 |
| Top | DIALLYL DISULFIDE | 146 | 5487.52 | 3.30 | 3.98E−05 | 1.38E+08 |
| Top | (+−)-ETHYL 3-METHYL-2-OXOPENTANOATE | 158 | 2276.17 | 1.96 | 5.06E−04 | 4.50E+06 |
| Top | 1-phenylethanone | 120 | 1728.98 | 1.59 | 6.61E−03 | 2.62E+05 |
| Top | ALLYL HEPTANOATE | 170 | 1235.24 | 4.16 | 1.75E−02 | 7.06E+04 |
| Top | (+−)-4-HEXANOLIDE | 114 | 841.23 | 0.48 | 2.63E−02 | 3.20E+04 |
| Top | (+−)-2-pentylcyclopentanone | 154 | 560.22 | 3.62 | 1.28E−03 | 4.38E+05 |
| Top | METHYL PHENYLACETATE | 150 | 555.30 | 1.98 | 3.21E−04 | 1.73E+06 |
| Top | 2-CYCLOHEXYL ETHYL ACETATE | 170 | 489.45 | 4.25 | 4.49E−02 | 1.09E+04 |
| Top | ETHYL 2-METHYL-1,3-DIOXOLANE-2-ACETATE | 174 | 479.20 | 1.12 | 1.62E−03 | 2.95E+05 |
| Top | 2-HYDROXY-3-METHYL-2-CYCLOPENTEN-1-ONE | 112 | 396.50 | 0.08 | 3.82E−04 | 1.04E+06 |
| Top | 2-METHOXY-4-METHYLPHENOL | 138 | 306.61 | 1.52 | 6.96E−04 | 4.41E+05 |
| Top | (+−)-4-HEPTANOLIDE | 128 | 295.34 | 1.16 | 5.18E−04 | 5.70E+05 |
| Top | hexyl (2E)-2-methyl-2-butenoate | 184 | 256.81 | 4.80 | 1.16E−02 | 2.22E+04 |

TABLE 8-continued

| | Perfuming Compounds Having a Sweet Note | | | | |
|---|---|---|---|---|---|
| Type | Name | Molecular Weight | Volatility (µg/l air) | Log P (n-octanol/ water) | Odor Threshold (µg/l air) | Odor Value |
| Top | (3Z)-3-hexen-1-yl (3Z)-3-hexenoate | 196 | 210.68 | 4.22 | 5.17E−02 | 4.08E+03 |
| Top | 2-PHENYLETHYL ACETATE | 164 | 201.26 | 2.49 | 2.14E−03 | 9.38E+04 |
| Top | HEXANOIC ACID | 116 | 197.90 | 1.92 | 1.82E−02 | 1.09E+04 |
| Top | 1-methoxy-4-[(1E)-1-propen-1-yl]benzene | 148 | 184.60 | 3.58 | 1.23E−03 | 1.51E+05 |
| Top | 2-PHENYLETHANOL | 122 | 159.75 | 1.41 | 1.02E−04 | 1.56E+06 |
| Top | (+−)-(E)-1-(2,2-DIMETHYL-6-METHYLENE-1-CYCLOHEXYL)-2-BUTEN-1-ONE | 192 | 152.99 | 4.11 | 3.73E−03 | 4.10E+04 |
| Top | (2E)-1-[(1RS,2SR)-2,6,6-trimethyl-3-cyclohexen-1-yl]-2-buten-1-one | 192 | 143.53 | 4.13 | 1.70E−05 | 8.44E+06 |
| Top | [2-(1-ETHOXYETHOXY)ETHYL]BENZENE (A) + 1,1-BIS(2-PHENYLETHOXY)ETHANE (B) | 270 | 136.67 | 2.96 | 1.59E−03 | 8.59E+04 |
| Top | 5-METHYL-3-HEPTANONE OXIME | 143 | 128.04 | 2.45 | 8.80E−03 | 1.45E+04 |
| Top | (+−)-(2E)-1-(2,6,6-trimethyl-2-cyclohexen-1-yl)-2-buten-1-one | 192 | 110.53 | 3.65 | 1.04E−04 | 1.06E+06 |
| Top | 3-METHYLBUTYL 2-PHENYLETHYL ETHER | 192 | 110.11 | 4.31 | 1.38E−02 | 7.96E+03 |
| Middle | (+−)-2-PENTYL-1-CYCLOPENTANOL | 156 | 97.79 | 3.59 | 5.43E−03 | 1.80E+04 |
| Middle | (1RS,2SR)-2-pentylcyclopentanol (A) + (1RS,2RS)-2-pentylcyclopentanol (B) | 156 | 97.79 | 3.59 | 5.43E−03 | 1.80E+04 |
| Middle | 3-HYDROXY-2-METHYL-4(4H)-PYRANONE | 126 | 92.42 | 0.11 | 4.17E−04 | 2.22E+05 |
| Middle | ALLYL 3-CYCLOHEXYLPROPANOATE | 196 | 75.80 | 4.51 | 7.96E−03 | 9.53E+03 |
| Middle | 2-PHENYLETHYL PIVALATE | 206 | 71.44 | 3.69 | 3.85E−02 | 1.86E+03 |
| Middle | 2-PHENYLETHYL ISOBUTYRATE | 192 | 67.38 | 3.16 | 6.70E−03 | 1.01E+04 |
| Middle | 4-(2,6,6-trimethyl-1-cyclohexen-1-yl)-2-butanone | 194 | 63.61 | 3.99 | 8.51E−03 | 7.48E+03 |
| Middle | BENZYL 3-METHYLBUTANOATE | 192 | 63.56 | 3.45 | 7.31E−03 | 8.70E+03 |
| Middle | 3-methyl-2-[(2Z)-2-penten-1-yl]-2-cyclopenten-1-one | 165 | 56.72 | 2.61 | 2.16E−04 | 2.63E+05 |

TABLE 8-continued

Perfuming Compounds Having a Sweet Note

| Type | Name | Molecular Weight | Volatility (µg/l air) | Log P (n-octanol/water) | Odor Threshold (µg/l air) | Odor Value |
|---|---|---|---|---|---|---|
| Middle | (+−)-6-METHYL-7-OXA-1-THIA-4-AZASPIRO[4.4]NONANE | 159 | 52.47 | 1.10 | 2.53E−06 | 2.07E+07 |
| Middle | 2-METHOXYNAPHTHALENE | 158 | 51.04 | 3.29 | 1.02E−05 | 5.00E+06 |
| Bottom | 2-ETHYL-3-HYDROXY-4(4H)-PYRANONE | 141 | 48.86 | 0.76 | 6.45E−05 | 7.57E+05 |
| Bottom | 1,1-DIMETHYL-2-PHENYLETHYL BUTANOATE | 220 | 34.65 | 4.42 | 2.68E−02 | 1.29E+03 |
| Bottom | 5-NONANOLIDE | 156 | 23.87 | 1.82 | 1.16E−05 | 2.06E+06 |
| Bottom | (+−)-TRANS-3-METHYL-4-NONANOLIDE | 170 | 21.05 | 2.59 | 8.33E−04 | 2.53E+04 |
| Bottom | 2,6-DIMETHOXYPHENOL | 154 | 19.23 | 1.02 | 8.01E−06 | 2.40E+06 |
| Bottom | (1E)-1-(2,6,6-trimethyl-1-cyclohexen-1-yl)-1-penten-3-one | 206 | 15.81 | 4.47 | 1.16E−04 | 1.37E+05 |
| Bottom | 3-BUTYLIDENE-1-BENZO[C]FURANONE | 188 | 14.37 | 3.12 | 8.65E−04 | 1.66E+04 |
| Bottom | 2-methoxy-4-[(1E)-1-propen-1-yl]phenol | 164 | 11.28 | 2.15 | 6.63E−06 | 1.70E+06 |
| Bottom | (+−)-4-DECANOLIDE | 170 | 10.49 | 3.02 | 1.61E−04 | 6.51E+04 |
| Bottom | (+−)-6-pentyltetrahydro-2H-pyran-2-one | 170 | 9.61 | 2.22 | 3.72E−05 | 2.58E+05 |
| Bottom | 2-ISOBUTYLQUINOLINE | 185 | 8.73 | 4.06 | 1.93E−04 | 4.53E+04 |
| Bottom | diethyl cis-1,4-cyclohexanedicarboxylate (A) + diethyl trans-1,4-cyclohexanedicarboxylate (B) | 228 | 8.51 | 2.65 | 2.87E−03 | 2.97E+03 |
| Bottom | (+−)-(E)-8-DECEN-5-OLIDE (A) + (+−)-(Z)-8-DECEN-5-OLIDE (B) | 168 | 6.89 | 2.70 | 5.14E−04 | 1.34E+04 |
| Bottom | 4-(4-METHOXYPHENYL)-2-BUTANONE | 178 | 5.58 | 2.06 | 5.88E−06 | 9.49E+05 |
| Bottom | 6-hexyltetrahydro-2H-pyran-2-one | 184 | 4.64 | 3.00 | 5.85E−05 | 7.93E+04 |
| Bottom | 4-hydroxy-3-methoxybenzaldehyde | 152 | 4.24 | 0.72 | 6.75E−06 | 6.28E+05 |
| Bottom | (+−)-5-heptyldihydro-2(3H)-furanone | 184 | 3.67 | 3.32 | 3.16E−05 | 1.16E+05 |
| Bottom | 2-(4-METHYL-1,3-THIAZOL-5-YL)-1-ETHANOL | 143 | 2.36 | 0.22 | 2.43E−04 | 9.71E+03 |
| Bottom | (1'R)-2-[2-(4'-METHYL-3'-CYCLOHEXEN-1'-YL)PROPYL]CYCLOPENTANONE | 220 | 2.05 | 5.19 | 1.66E−04 | 1.24E+04 |
| Bottom | 4-formyl-2-methoxyphenyl 2-methylpropanoate | 222 | 1.01 | 1.90 | 7.33E−05 | 1.38E+04 |

TABLE 8-continued

| Perfuming Compounds Having a Sweet Note | | | | | | |
|---|---|---|---|---|---|---|
| Type | Name | Molecular Weight | Volatility (μg/l air) | Log P (n-octanol/water) | Odor Threshold (μg/l air) | Odor Value |
| Bottom | (+−)-6-heptyltetrahydro-2H-pyran-2-one | 198 | 0.90 | 3.42 | 1.27E−04 | 7.06E+03 |
| Bottom | 2-CHROMENONE | 146 | 0.51 | 1.35 | 1.62E−05 | 3.16E+04 |
| Bottom | 1,4-dioxacyclohexadecane-5,16-dione | 256 | 0.46 | 3.83 | 7.05E−04 | 6.55E+02 |
| Bottom | 2-PHENYLETHYL PHENYLACETATE | 240 | 0.20 | 3.59 | 9.08E−04 | 2.24E+02 |
| Bottom | 3-ethoxy-4-hydroxybenzaldehyde | 166 | 0.11 | 1.27 | 2.10E−05 | 5.25E+03 |

TABLE 9

| Perfuming Compounds Having a Gourmand Note | | | | | | |
|---|---|---|---|---|---|---|
| Type | Name | Molecular Weight | Volatility (μg/l air) | Log P (n-octanol/water) | Odor Threshold (μg/l air) | Odor Value |
| Top | BUTYL ACETATE | 116 | 117207.52 | 2.11 | 4.18E−01 | 2.80E+05 |
| Top | 3-METHYLBUTYL ACETATE (A) + (+−)-2-METHYLBUTYL ACETATE (B) | 130 | 51307.81 | 2.65 | 5.92E−02 | 8.67E+05 |
| Top | (+−)-3-HYDROXY-2-BUTANONE | 88 | 33382.87 | −1.03 | 1.46E−02 | 2.28E+06 |
| Top | 1-BUTANOL | 74 | 17700.00 | 0.88 | 8.70E−02 | 2.03E+05 |
| Top | (+−)-4-methyl-4-penten-2-yl 2-methylpropanoate | 170 | 9902.98 | 3.57 | 2.26E−01 | 4.39E+04 |
| Top | ETHYL HEXANOATE | 145 | 9675.10 | 3.12 | 9.11E−04 | 1.06E+07 |
| Top | DIALLYL DISULFIDE | 146 | 5487.52 | 3.30 | 3.98E−05 | 1.38E+08 |
| Top | ALLYL HEPTANOATE | 170 | 1235.24 | 4.16 | 1.75E−02 | 7.06E+04 |
| Top | (+−)-2-pentylcyclopentanone | 154 | 560.22 | 3.62 | 1.28E−03 | 4.38E+05 |
| Top | METHYL PHENYLACETATE | 150 | 555.30 | 1.98 | 3.21E−04 | 1.73E+06 |
| Top | 2-CYCLOHEXYL ETHYL ACETATE | 170 | 489.45 | 4.25 | 4.49E−02 | 1.09E+04 |
| Top | ETHYL 2-METHYL-1,3-DIOXOLANE-2-ACETATE | 174 | 479.20 | 1.12 | 1.62E−03 | 2.95E+05 |
| Top | (3Z)-3-hexen-1-yl (3Z)-3-hexenoate | 196 | 210.68 | 4.22 | 5.17E−02 | 4.08E+03 |
| Top | 2-PHENYLETHYL ACETATE | 164 | 201.26 | 2.49 | 2.14E−03 | 9.38E+04 |
| Top | HEXANOIC ACID | 116 | 197.90 | 1.92 | 1.82E−02 | 1.09E+04 |
| Top | 1-methoxy-4-[(1E)-1-propen-1-yl]benzene | 148 | 184.60 | 3.58 | 1.23E−03 | 1.51E+05 |
| Top | 2-PHENYLETHANOL | 122 | 159.75 | 1.41 | 1.02E−04 | 1.56E+06 |

TABLE 9-continued

Perfuming Compounds Having a Gourmand Note

| Type | Name | Molecular Weight | Volatility (µg/l air) | Log P (n-octanol/water) | Odor Threshold (µg/l air) | Odor Value |
|---|---|---|---|---|---|---|
| Top | (+−)-(E)-1-(2,2-DIMETHYL-6-METHYLENE-1-CYCLOHEXYL)-2-BUTEN-1-ONE | 192 | 152.99 | 4.11 | 3.73E−03 | 4.10E+04 |
| Top | (2E)-1-[(1RS,2SR)-2,6,6-trimethyl-3-cyclohexen-1-yl]-2-buten-1-one | 192 | 143.53 | 4.13 | 1.70E−05 | 8.44E+06 |
| Top | [2-(1-ETHOXYETHOXY)ETHYL]BENZENE (A) + 1,1-BIS(2-PHENYLETHOXY)ETHANE (B) | 270 | 136.67 | 2.96 | 1.59E−03 | 8.59E+04 |
| Top | 5-METHYL-3-HEPTANONEOXIME | 143 | 128.04 | 2.45 | 8.80E−03 | 1.45E+04 |
| Top | 3-METHYLBUTYL 2-PHENYLETHYL ETHER | 192 | 110.11 | 4.31 | 1.38E−02 | 7.96E+03 |
| Top | (+−)-4-OCTANOLIDE | 142 | 108.41 | 1.80 | 2.32E−05 | 4.67E+06 |
| Middle | (3RS,3ARS,6SR,7ASR)-PERHYDRO-3,6-DIMETHYL-BENZO[B]FURAN-2-ONE (A) + (3SR,3ARS,6SR,7ASR)-PERHYDRO-3,6-DIMETHYL-BENZO[B]FURAN-2-ONE (B) | 168 | 80.76 | 2.14 | 1.84E−06 | 4.39E+07 |
| Middle | ALLYL 3-CYCLOHEXYLPROPANOATE | 196 | 75.80 | 4.51 | 7.96E−03 | 9.53E+03 |
| Middle | (3S,3aS,6R,7aR)-3,6-dimethylhexahydro-1-benzofuran-2(3H)-one | 168 | 74.03 | 2.11 | 3.46E−05 | 2.14E+06 |
| Middle | 2-PHENYLETHYL PIVALATE | 206 | 71.44 | 3.69 | 3.85E−02 | 1.86E+03 |
| Middle | 2-PHENYLETHYL ISOBUTYRATE | 192 | 67.38 | 3.16 | 6.70E−03 | 1.01E+04 |
| Middle | 1-oxaspiro[4.5]decan-2-one | 154 | 62.86 | 1.66 | 2.90E−04 | 2.17E+05 |
| Middle | benzo[d][1,3]dioxole-5-carbaldehyde | 150 | 61.82 | 1.52 | 1.01E−04 | 6.12E+05 |
| Middle | 3-methyl-2-[(2Z)-2-penten-1-yl]-2-cyclopenten-1-one | 165 | 56.72 | 2.61 | 2.16E−04 | 2.63E+05 |
| Middle | 2-METHOXYNAPHTHALENE | 158 | 51.04 | 3.29 | 1.02E−05 | 5.00E+06 |
| Bottom | 1,1-DIMETHYL-2-PHENYLETHYL BUTANOATE | 220 | 34.65 | 4.42 | 2.68E−02 | 1.29E+03 |
| Bottom | (+−)-4-NONANOLIDE | 156 | 27.42 | 2.45 | 1.45E−04 | 1.89E+05 |
| Bottom | 5-NONANOLIDE | 156 | 23.87 | 1.82 | 1.16E−05 | 2.06E+06 |
| Bottom | (+−)-TRANS-3-METHYL-4-NONANOLIDE | 170 | 21.05 | 2.59 | 8.33E−04 | 2.53E+04 |

TABLE 9-continued

Perfuming Compounds Having a Gourmand Note

| Type | Name | Molecular Weight | Volatility (μg/l air) | Log P (n-octanol/water) | Odor Threshold (μg/l air) | Odor Value |
|---|---|---|---|---|---|---|
| Bottom | 2,6-DIMETHOXYPHENOL | 154 | 19.23 | 1.02 | 8.01E−06 | 2.40E+06 |
| Bottom | (1E)-1-(2,6,6-trimethyl-1-cyclohexen-1-yl)-1-penten-3-one | 206 | 15.81 | 4.47 | 1.16E−04 | 1.37E+05 |
| Bottom | 3-BUTYLIDENE-1-BENZO[C]FURANONE | 188 | 14.37 | 3.12 | 8.65E−04 | 1.66E+04 |
| Bottom | 2-methoxy-4-[(1E)-1-propen-1-yl]phenol | 164 | 11.28 | 2.15 | 6.63E−06 | 1.70E+06 |
| Bottom | (+−)-4-DECANOLIDE | 170 | 10.49 | 3.02 | 1.61E−04 | 6.51E+04 |
| Bottom | (+−)-6-pentyltetrahydro-2H-pyran-2-one | 170 | 9.61 | 2.22 | 3.72E−05 | 2.58E+05 |
| Bottom | diethyl cis-1,4-cyclohexanedicarboxylate (A) + diethyl trans-1,4-cyclohexanedicarboxylate (B) | 228 | 8.51 | 2.65 | 2.87E−03 | 2.97E+03 |
| Bottom | (+−)-(E)-8-DECEN-5-OLIDE (A) + (+−)-(Z)-8-DECEN-5-OLIDE (B) | 168 | 6.89 | 2.70 | 5.14E−04 | 1.34E+04 |
| Bottom | 4-(4-METHOXYPHENYL)-2-BUTANONE | 178 | 5.58 | 2.06 | 5.88E−06 | 9.49E+05 |
| Bottom | 6-hexyltetrahydro-2H-pyran-2-one | 184 | 4.64 | 3.00 | 5.85E−05 | 7.93E+04 |
| Bottom | 4-hydroxy-3-methoxybenzaldehyde | 152 | 4.24 | 0.72 | 6.75E−06 | 6.28E+05 |
| Bottom | (+−)-5-heptyldihydro-2(3H)-furanone | 184 | 3.67 | 3.32 | 3.16E−05 | 1.16E+05 |
| Bottom | (1'R)-2-[2-(4'-METHYL-3'-CYCLOHEXEN-1'-YL)PROPYL]CYCLOPENTANONE | 220 | 2.05 | 5.19 | 1.66E−04 | 1.24E+04 |
| Bottom | 4-formyl-2-methoxyphenyl 2-methylpropanoate | 222 | 1.01 | 1.90 | 7.33E−05 | 1.38E+04 |
| Bottom | (+−)-6-heptyltetrahydro-2H-pyran-2-one | 198 | 0.90 | 3.42 | 1.27E−04 | 7.06E+03 |
| Bottom | 2-CHROMENONE | 146 | 0.51 | 1.35 | 1.62E−05 | 3.16E+04 |
| Bottom | 2-PHENYLETHYL PHENYLACETATE | 240 | 0.20 | 3.59 | 9.08E−04 | 2.24E+02 |

TABLE 10

Perfuming Compounds Having a Woody Note

| Type | Name | Molecular Weight | Volatility (μg/l air) | Log P (n-octanol/water) | Odor Threshold (μg/l air) | Odor Value |
|---|---|---|---|---|---|---|
| Top | 1-BUTANOL | 74 | 17700.00 | 0.88 | 8.70E−02 | 2.03E+05 |
| Top | (+−)-methyl 2-ethylhexanoate | 158 | 6677.64 | 3.37 | 1.74E−01 | 3.84E+04 |

TABLE 10-continued

Perfuming Compounds Having a Woody Note

| Type | Name | Molecular Weight | Volatility (µg/l air) | Log P (n-octanol/ water) | Odor Threshold (µg/l air) | Odor Value |
|---|---|---|---|---|---|---|
| Top | 3-METHYLBUTANOIC ACID | 102 | 1530.76 | 1.49 | 2.23E−04 | 6.87E+06 |
| Top | 6,6-DIMETHOXY-2,5,5-TRIMETHYL-2-HEXENE | 186 | 1311.32 | 3.90 | 1.26E−02 | 1.04E+05 |
| Top | 4-(2-methyl-2-propanyl)cyclohexanone | 154 | 755.28 | 2.77 | 1.15E−01 | 6.57E+03 |
| Top | (1R,2R)-1,7,7-TRIMETHYL-BICYCLO[2.2.1]HEPT-2-YL ACETATE | 196 | 735.37 | 4.13 | 4.46E−02 | 1.65E+04 |
| Top | (A) + (+−)-3,5,6,6-tetramethyl-4-methylidene-2-heptanone (B) + (+−)-(4E)-3,4,5,6,6-pentamethyl-4-hepten-2-one (C) + (+−)-(3Z)-3,4,5,6,6-pentamethyl-3-hepten-2-one (D) + (+−)-(3E)-3,4,5,6,6-pentamethyl-3-hepten-2-one (E) | 182 | 659.22 | 3.71 | 7.24E−02 | 9.11E+03 |
| Top | (+−)-(3Z)-3,4,5,6,6-PENTAMETHYL-3-HEPTEN-2-ONE | 182 | 659.22 | 3.71 | 7.24E−02 | 9.11E+03 |
| Top | cis-4-(2-methyl-2-propanyl)cyclohexyl acetate (A) + trans-4-(2-methyl-2-propanyl)cyclohexyl acetate (B) | 198 | 229.76 | 4.18 | 2.33E−02 | 9.87E+03 |
| Top | (1S,2S,4S)-1,7,7-trimethylbicyclo[2.2.1]hept-2-yl propanoate | 210 | 216.42 | 4.66 | 4.55E−02 | 4.76E+03 |
| Top | (+−)-1-(2-TERT-BUTYL-1-CYCLOHEXYLOXY)-2-BUTANOL | 228 | 205.05 | 4.65 | 3.53E−02 | 5.81E+03 |
| Top | (+−)-ALPHA-TERPINEOL | 154 | 172.78 | 2.91 | 1.03E−01 | 1.68E+03 |
| Top | (+−)-2-ETHOXY-2,6,6-TRIMETHYL-9-METHYLENE-BICYCLO[3.3.1]NONANE | 222 | 135.00 | 6.50 | 1.37E−01 | 9.83E+02 |
| Top | (+−)-(2E)-1-(2,6,6-trimethyl-2-cyclohexen-1-yl)-2-buten-1-one | 192 | 110.53 | 3.65 | 1.04E−04 | 1.06E+06 |
| Top | (+−)-(E)-3-METHYL-4-(2,6,6-TRIMETHYL-2-CYCLOHEXEN-1-YL)-3-BUTEN-2-ONE | 206 | 106.28 | 4.09 | 5.03E−05 | 2.11E+06 |

TABLE 10-continued

| | | | | Log P | | |
|---|---|---|---|---|---|---|
| | | Molecular | Volatility | (n-octanol/ | Odor Threshold | Odor |
| Type | Name | Weight | (µg/l air) | water) | (µg/l air) | Value |

Perfuming Compounds Having a Woody Note

| Type | Name | Molecular Weight | Volatility (µg/l air) | Log P (n-octanol/water) | Odor Threshold (µg/l air) | Odor Value |
|---|---|---|---|---|---|---|
| Middle | (2E)-1-(2,6,6-trimethyl-1,3-cyclohexadien-1-yl)-2-buten-1-one | 190 | 91.38 | 3.33 | 3.00E−06 | 3.04E+07 |
| Middle | (5RS,6RS)-2,6,10,10-TETRAMETHYL-1-OXASPIRO[4.5]DECAN-6-OL | 212 | 84.04 | 3.51 | 5.15E−04 | 1.63E+05 |
| Middle | 2-TERT-BUTYL-1,4-DIMETHOXYBENZENE | 194 | 82.95 | 4.00 | 1.65E−02 | 5.02E+03 |
| Middle | (2E)-1-(2,6,6-trimethyl-1-cyclohexen-1-yl)-2-buten-1-one | 192 | 81.66 | 3.63 | 2.18E−04 | 3.75E+05 |
| Middle | (+−)-3ENDO-METHOXY-7,7-DIMETHYL-10-METHYLENE-BICYCLO[4.3.1]DECANE (A) + (+−)-3EXO-METHOXY-7,7-DIMETHYL-10-METHYLENE-BICYCLO[4.3.1]DECANE (B) | 208 | 79.45 | 5.73 | 4.82E−03 | 1.65E+04 |
| Middle | (E)-3-PHENYL-2-PROPENAL | 132 | 70.14 | 1.50 | 1.36E−03 | 5.16E+04 |
| Middle | (Z)-3-PHENYL-2-PROPENAL (A) + (E)-3-PHENYL-2-PROPENAL (B) | 132 | 70.14 | 1.50 | 1.36E−03 | 5.16E+04 |
| Middle | (E)-3-PHENYL-2-PROPENAL | 132 | 70.14 | 1.50 | 1.36E−03 | 5.16E+04 |
| Middle | (E)-3-PHENYL-2-PROPENENITRILE | 129 | 66.00 | 1.98 | 8.97E−05 | 7.36E+05 |
| Middle | 4-(2,6,6-trimethyl-1-cyclohexen-1-yl)-2-butanone | 194 | 63.61 | 3.99 | 8.51E−03 | 7.48E+03 |
| Middle | (2R)-2-methyl-4-[(1R)-2,2,3-trimethyl-3-cyclopenten-1-yl]-4-pentenal (A) + (2S)-2-methyl-4-[(1R)-2,2,3-trimethyl-3-cyclopenten-1-yl]-4-pentenal (B) | 206 | 63.49 | 4.25 | 2.22E−03 | 2.86E+04 |
| Middle | 2-(6,6-DIMETHYL-BICYCLO[3.1.1]HEPT-2-EN-2-YL)ETHYL ACETATE | 208 | 60.02 | 4.41 | 1.10E−01 | 5.45E+02 |
| Middle | 1,2,3,4,5,6,7,8-OCTAHYDRO-8,8-DIMETHYL-2-NAPHTHALENE CARBALDEHYDE (A) + (B,C,D) + OCTAHYDRO-5,5-DIMETHYL-2-NAPHTHALENE CARBALDEHYDE | 192 | 55.09 | 3.65 | 3.91E−03 | 1.41E+04 |

TABLE 10-continued

| | Perfuming Compounds Having a Woody Note | | | | | |
|---|---|---|---|---|---|---|
| Type | Name | Molecular Weight | Volatility (μg/l air) | Log P (n-octanol/ water) | Odor Threshold (μg/l air) | Odor Value |
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 43.62 | 4.22 | 6.30E−05 | 6.92E+05 |
| Bottom | (+−)-8-methoxycedrane | 236 | 42.22 | 7.59 | 2.09E−02 | 2.02E+03 |
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 36.33 | 4.83 | 1.92E−04 | 1.89E+05 |
| Bottom | (+−)-7-METHOXY-3,7-DIMETHYL-2-OCTANOL | 188 | 35.54 | 2.19 | 2.66E−02 | 1.34E+03 |
| Bottom | (3E)-4-(2,6,6-trimethyl-1-cyclohexen-1-yl)-3-buten-2-one | 192 | 35.41 | 3.88 | 3.58E−05 | 9.89E+05 |
| Bottom | (+−)-(E)-3-METHYL-4-(2,6,6-TRIMETHYL-2-CYCLOHEXEN-1-YL)-3-BUTEN-2-ONE (A) + (E)-1-(2,6,6-TRIMETHYL-2-CYCLOHEXEN-1-YL)-1-PENTEN-3-ONE (B) + (+−)-(E)-1-(2,2-DIMETHYL-6-METHYLENE-1-CYCLOHEXYL)-1-PENTEN-3-ONE (C) + (E)-1-(2,6,6-TRIMETHYL-1-CYCLOHEXEN-1-YL)-1-PENTEN-3-ONE (D) | 206 | 34.78 | 4.09 | 2.15E−04 | 1.62E+05 |
| Bottom | (+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B) | 206 | 34.44 | 4.28 | 1.70E−04 | 2.03E+05 |
| Bottom | BENZYL (E)-2-METHYL-2-BUTENOATE | 190 | 33.88 | 3.32 | 3.07E−04 | 1.11E+05 |

TABLE 10-continued

| Perfuming Compounds Having a Woody Note | | | | | | |
|---|---|---|---|---|---|---|
| Type | Name | Molecular Weight | Volatility (μg/l air) | Log P (n-octanol/ water) | Odor Threshold (μg/l air) | Odor Value |
| Bottom | (+−)-2,4-dimethyl-4,4a,5,9b-tetrahydroindeno[1,2-d][1,3]dioxine (ISOMER A) + (+−)-2,4-dimethyl-4,4a,5,9b-tetrahydroindeno[1,2-d][1,3]dioxine (ISOMER B) (A + B) | 204 | 32.53 | 2.44 | 2.43E−04 | 1.34E+05 |
| Bottom | 1,2,3,5,6,7-HEXAHYDRO-1,1,2,3,3-PENTAMETHYL-4-INDENONE | 207 | 29.81 | 3.65 | 4.57E−03 | 6.52E+03 |
| Bottom | (+−)-(6RS,10RS)-2,2,8,10-tetramethylspiro[5.5]undec-8-en-1-one (A) + (+−)-(6RS,10SR)-2,2,8,10-tetramethylspiro[5.5]undec-8-en-1-one (B) + (6RS,7RS)-2,2,7,9-tetramethylspiro[5.5]undec-8-en-1-one (C) + (6RS,7SR)-2,2,7,9-tetramethylspiro[5.5]undec-8-en-1-one (D) | 220 | 22.40 | 5.40 | 5.59E−03 | 4.01E+03 |
| Bottom | (+−)-(E)-4-(2,2,C-3,T-6-TETRAMETHYL-R-1-CYCLOHEXYL)-3-BUTEN-2-ONE | 208 | 20.50 | 4.62 | 5.14E−04 | 3.99E+04 |
| Bottom | (+−)-(E)-4-(2,2,C-3,T-6-TETRAMETHYL-R-1-CYCLOHEXYL)-3-BUTEN-2-ONE (A) + (+−)-(E)-4-(2,2,T-3,T-6-TETRAMETHYL-R-1-CYCLOHEXYL)-3-BUTEN-2-ONE (B) | 208 | 20.50 | 4.62 | 5.14E−04 | 3.99E+04 |
| Bottom | (E)-3-METHYL-5-(2,2,3-TRIMETHYL-3-CYCLOPENTEN-1-YL)-4-PENTEN-2-OL | 208 | 20.41 | 4.33 | 9.56E−05 | 2.13E+05 |

TABLE 10-continued

Perfuming Compounds Having a Woody Note

| Type | Name | Molecular Weight | Volatility (μg/l air) | Log P (n-octanol/ water) | Odor Threshold (μg/l air) | Odor Value |
|---|---|---|---|---|---|---|
| Bottom | (2R,4E)-3,3-dimethyl-5-[(1R)-2,2,3-trimethyl-3-cyclopenten-1-yl]-4-penten-2-ol (A) + (2S,4E)-3,3-dimethyl-5-[(1R)-2,2,3-trimethyl-3-cyclopenten-1-yl]-4-penten-2-ol (B) | 222 | 16.31 | 4.77 | 7.11E−05 | 2.29E+05 |
| Bottom | 5,5,8a-trimethyldecahydro-2-naphthalenyl acetate | 238 | 14.41 | 5.50 | 4.19E−04 | 3.44E+04 |
| Bottom | (2RS,4aRS,8aSR)-5,5,8a-trimethyldecahydro-2-naphthalenyl acetate | 238 | 14.41 | 5.50 | 4.19E−04 | 3.44E+04 |
| Bottom | (+−)-3,6,8,8-tetramethyloctahydro-1H-3a,7-methanoazulen-6-ol | 222 | 11.83 | 5.39 | 3.38E−02 | 3.51E+02 |
| Bottom | (+−)-1-(OCTAHYDRO-2,3,8,8-TETRAME-2-NAPHTHALEN YL)-1-ETHANONE (DOUBLE BOND: 4A,5 (A) + 4,4A (B) + 4A,8A (C) | 234 | 10.59 | 5.55 | 2.59E−04 | 4.09E+04 |
| Bottom | 3aRS,5aSR,9aSR,9bSR)-3a,6,6,9a-tetramethyldodecahydronaphtho[2,1-b]furan | 236 | 9.23 | 6.93 | 2.16E−03 | 4.28E+03 |
| Bottom | (1RS,6RS,11RS)-2,2,9,11-tetramethylspiro[5.5]undec-8-en-1-yl acetate | 264 | 8.25 | 6.44 | 3.79E−03 | 2.18E+03 |
| Bottom | (−)-(3aR,5aS,9aS,9bR)-3a,6,6,9a-tetramethyldodecahydronaphtho[2,1-b]furan | 236 | 8.02 | 6.87 | 1.08E−05 | 7.45E+05 |
| Bottom | (+−)-1-(OCTAHYDRO-2,3,8,8-TETRAME-2-NAPHTHALENYL)-1-ETHANONE (DOUBLE BOND: 4A,5 (A) + 4,4A (B) + 4A,8A (C) | 234 | 7.59 | 5.24 | 4.24E−04 | 1.79E+04 |
| Bottom | (+−)-(4Z,8E)-1,5,8-trimethyl-13-oxabicyclo[10.1.0]trideca-4,8-diene (A) + (+−)-(4Z,8E)-1,4,8-trimethyl-13-oxabicyclo[10.1.0]trideca-4,8-diene (B) | 220 | 7.11 | 4.88 | 7.14E−03 | 9.96E+02 |

TABLE 10-continued

| Perfuming Compounds Having a Woody Note | | | | | | |
|---|---|---|---|---|---|---|
| Type | Name | Molecular Weight | Volatility (µg/l air) | Log P (n-octanol/ water) | Odor Threshold (µg/l air) | Odor Value |
| Bottom | (1S,4S,9S,10R,13R)-5,5,9,13-tetramethyl-14,16-dioxatetracyclo[11.2.1.0~1,10~.0~4,9~]hexadecane (A) + (1R,4S,9S,10R,13S)-5,5,9,13-tetramethyl-14,16-dioxatetracyclo[11.2.1.0~1,10~.0~4,9~]hexadecane (B) | 278 | 6.77 | 4.59 | 4.36E−04 | 1.55E+04 |
| Bottom | (ETHOXYMETHOXY)CYCLODODECANE | 242 | 6.63 | 6.59 | 8.90E−02 | 7.45E+01 |
| Bottom | (+−)-3-methyl-5-(2,2,3-trimethyl-3-cyclopenten-1-yl)-2-pentanol | 210 | 5.22 | 4.68 | 1.52E−03 | 3.43E+03 |
| Bottom | (2S)-2-methyl-4-[(1R)-2,2,3-trimethyl-3-cyclopenten-1-yl]-4-penten-1-ol (A) + (2R)-2-methyl-4-[(1R)-2,2,3-trimethyl-3-cyclopenten-1-yl]-4-penten-1-ol (B) | 208 | 5.04 | 4.43 | 1.70E−05 | 2.97E+05 |
| Bottom | (+−)-(1-ethoxyethoxy)cyclododecane | 256 | 5.04 | 6.68 | 2.51E−02 | 2.01E+02 |
| Bottom | (+)-(1R,7R)-10,10-DIMETHYL-TRICYCLO[7.1.1.0(2,7)]UNDEC-2-EN-4-ONE | 190 | 4.86 | 3.00 | 2.86E−05 | 1.70E+05 |
| Bottom | (+)-(1S,2S,3S,5R)-2,6,6-trimethylspiro[bicyclo[3.1.1]heptane-3,1'-cyclohexane]-2'-en-4'-one | 218 | 4.14 | 4.39 | 6.32E−04 | 6.54E+03 |
| Bottom | 2-(2,4-DIMETHYL-3-CYCLOHEXEN-1-YL)-5-METHYL-5-(1-METHYLPROPYL)-1,3-DIOXANE | 266 | 3.82 | 6.50 | 1.67E−03 | 2.28E+03 |
| Bottom | (+−)-2-ETHYL-4-(2,2,3-TRIMETHYL-3-CYCLOPENTEN-1-YL)-2-BUTEN-1-OL | 208 | 3.69 | 4.39 | 7.80E−05 | 4.73E+04 |
| Bottom | (+−)-1-(2,2,3,6-TETRAMETHYL-CYCLOHEXYL)-3-HEXANOL | 240 | 3.42 | 5.96 | 4.05E−04 | 8.44E+03 |
| Bottom | 9-ACETYL-8-CEDRENE + CEDARWOOD SESQUITERPENES | 246 | 3.21 | 5.84 | 1.43E−03 | 2.25E+03 |

TABLE 10-continued

| | Perfuming Compounds Having a Woody Note | | | | | |
|---|---|---|---|---|---|---|
| Type | Name | Molecular Weight | Volatility (μg/l air) | Log P (n-octanol/ water) | Odor Threshold (μg/l air) | Odor Value |
| Bottom | (+−)-(1E)-1-(2,6,6-trimethyl-2-cyclohexen-1-yl)-1,6-heptadien-3-one (A) + (1E)-1-(2,6,6-trimethyl-1-cyclohexen-1-yl)-1,6-heptadien-3-one (B) | 232 | 3.01 | 4.86 | 7.14E−03 | 4.22E+02 |
| Bottom | (−)-(2E)-2-ethyl-4-[(1R)-2,2,3-trimethyl-3-cyclopenten-1-yl]-2-buten-1-ol | 208 | 2.75 | 4.44 | 2.41E−05 | 1.14E+05 |
| Bottom | 1-[(1RS,6SR)-2,2,6-trimethylcyclohexyl]-3-hexanol | 226 | 2.34 | 5.42 | 5.92E−04 | 3.95E+03 |
| Bottom | (3R)-1-[(1R,6S)-2,2,6-trimethylcyclohexyl]-3-hexanol (A) + (3S)-1-[(1R,6S)-2,2,6-trimethylcyclohexyl]-3-hexanol (B) + (3R)-1-[(1S,6S)-2,2,6-trimethylcyclohexyl]-3-hexanol (C) | 226 | 2.20 | 5.52 | 4.40E−04 | 5.00E+03 |
| Bottom | (−)-(3aR,5aS,9aS,9bR)-3a,6,6,9a-tetramethyldodecahydronaphtho[2,1-b]furan | 236 | 2.19 | 6.88 | 1.31E−05 | 1.68E+05 |
| Bottom | (3aRS,5aSR,9aSR,9bRS)-3a,6,6,9a-tetramethyldodecahydronaphtho[2,1-b]furan (A) + (3aRS,5aSR,9aSR,9bSR)-3a,6,6,9a-tetramethyldodecahydronaphtho[2,1-b]furan (B) | 236 | 2.19 | 5.95 | 6.49E−05 | 3.37E+04 |
| Bottom | (−)-(3aR,5aS,9aS,9bR)-3a,6,6,9a-tetramethyldodecahydronaphtho[2,1-b]furan | 236 | 2.19 | 6.85 | 3.94E−05 | 5.56E+04 |
| Bottom | (+−)-1-(OCTAHYDRO-2,3,8,8-TETRAME-2-NAPHTHALENYL)-1-ETHANONE (DOUBLE BOND: 4A,5 (A) + 4,4A (B) + 4A,8A (C) | 234 | 1.85 | 5.82 | 5.57E−04 | 3.33E+03 |
| Bottom | (1′S,3′R)-{1-METHYL-2-[(1′,2′,2′-TRIMETHYLBICYCLO[3.1.0]HEX-3′-YL)METHYL]CYCLOPROPYL}METHANOL | 222 | 1.74 | 4.82 | 2.18E−06 | 8.01E+05 |
| Bottom | (+)-METHYL (1R)-CIS-3-OXO-2-PENTYL-1-CYCLOPENTANEACETATE | 226 | 1.71 | 2.95 | 2.82E−04 | 6.06E+03 |

TABLE 10-continued

Perfuming Compounds Having a Woody Note

| Type | Name | Molecular Weight | Volatility (μg/l air) | Log P (n-octanol/water) | Odor Threshold (μg/l air) | Odor Value |
|---|---|---|---|---|---|---|
| Bottom | 2/3/4-(5,5,6-TRIMETHYLBICYCLO[2.2.1]HEPT-2-YL)-1-CYCLOHEXANOL (A/B/C) + 2-(1,7,7-TRIMETHYLBICYCLO[2.2.1]HEPT-2-YL)-1-CYCLOHEXANOL (D) | 236 | 1.38 | 5.23 | 7.70E−04 | 1.79E+03 |
| Bottom | 1-(2,6,10-TRIMETHYL-1(2),5,9-CYCLODODECATRIEN-1-YL)-1-ETHANONE + 1-(6,10-DIMETHYL-2-METHYLENE-5,9-...)-1-E... | 246 | 1.24 | 5.94 | 3.88E−04 | 3.19E+03 |
| Bottom | (−)-(1R,3S,7R,8R,10S,13R)-5,5,7,9,9,13-HEXAMETHYL-4,6-DIOXATETRACYCLO[6.5.1.0(1,10).0(3,7)]TETRADECANE | 278 | 0.00 | 4.23 | 3.90E−06 | 6.26E+02 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A perfume composition comprising at least two perfuming accords, wherein a first perfume accord of the at least two perfuming accords comprises perfuming compounds dominated by a first olfactive note selected from the group consisting of:
   floral, water, green, fruity and citrus olfactive notes,
   wherein a second perfume accord of the at least two perfuming accords comprises perfuming compounds dominated by a second olfactive note selected from the group consisting of floral, fruity, citrus, sweet, oriental, and woody olfactive notes,
   wherein the first and second olfactive notes are contrasting notes,
   wherein the contrasting notes are olfactive notes separated by at least one adjacent olfactive note on the fragrance wheel shown in FIG. 1,
   wherein the first perfume accord is present in the perfume composition in an amount sufficient for the first olfactive note to be perceived by a subject at a first time,
   wherein the second perfume accord is present in the perfume composition in an amount sufficient for the second olfactive note to be perceived by a subject at a second time, and
   wherein the perception of the first olfactive note and the second olfactive note is at a level sufficient to reduce, prevent, or suppress a reduced perception of the perfume composition by the subject over time.

2. The perfume composition of claim 1, wherein the second time is after the first time.

3. The perfume composition of claim 1, wherein the first perfume accord comprises perfuming compounds having a volatility ranging from 70,000 to 100 μg/l in air.

4. The perfume composition of claim 1, wherein the second perfume accord comprises perfuming compounds having a volatility ranging from 99 to 50 μg/l in air.

5. The perfume composition of claim 1, wherein the perfume composition further comprises a third perfume accord comprising perfuming compounds dominated by a third olfactive note, wherein the third perfume accord is present in the perfume composition in an amount sufficient for the third olfactive note to be perceived by a subject at a third time;
   wherein the third olfactive note is selected from the group consisting of floral, fruity, citrus, sweet, oriental, and woody olfactive notes.

6. The perfume composition of claim 5, wherein the third time is after the second time.

7. The perfume composition of claim 5, wherein the third perfume accord comprises perfuming compounds having a volatility ranging from 49 to 0.1 μg/l in air.

8. The perfume composition of claim 1, wherein the sufficient amount of the first perfume accord is from 30% to 70% by weight of the perfume composition.

9. The perfume composition of claim 1, wherein the sufficient amount of the second perfume accord is from 30% to 70% by weight of the perfume composition.

10. The perfume composition of claim 5, wherein the sufficient amount of the third perfume accord is from 30% to 70% by weight of the perfume composition.

11. The perfume composition of claim 1, wherein the first perfume accord and the second perfume accord are present in the perfume composition in a weight ratio ranging from 3:1 to 1:3.

12. The perfume composition of claim 1, wherein the first perfume accord and the second perfume accord are present in the perfume composition at a weight ratio of 1:1.

13. The perfume composition of claim 5, wherein the first perfume accord the second perfume accord, and the third perfume accord are present in the perfume composition at a weight ratio of 1:1:1.

14. The perfume composition of claim 1, wherein the perception of the second olfactive note after the first olfactive note is at a level sufficient to reduce, prevent, or suppress a reduced perception of the perfume composition by the subject over time.

15. The perfume composition of claim 5, wherein the perception of the first olfactive note, the second olfactive note, and the third olfactive note is at a level sufficient to reduce, prevent, or suppress a reduced perception of the perfume composition by the subject over time.

\* \* \* \* \*